United States Patent
John et al.

(10) Patent No.: US 8,781,566 B2
(45) Date of Patent: Jul. 15, 2014

(54) SYSTEM AND METHODS FOR SLIDING-SCALE CARDIAC EVENT DETECTION

(75) Inventors: Michael Sasha John, Larchmont, NY (US); David R. Fischell, Fair Haven, NJ (US); Bruce Hopenfeld, Salt Lake City, UT (US)

(73) Assignee: Angel Medical Systems, Inc., Fair Haven, NJ (US)

( * ) Notice: Subject to any disclaimer, the term of this patent is extended or adjusted under 35 U.S.C. 154(b) by 1884 days.

(21) Appl. No.: 12/068,776

(22) Filed: Feb. 12, 2008

(65) Prior Publication Data

US 2008/0188763 A1 Aug. 7, 2008

Related U.S. Application Data

(63) Continuation-in-part of application No. 11/710,902, filed on Sep. 27, 2007.

(60) Provisional application No. 60/767,073, filed on Mar. 1, 2006, provisional application No. 60/830,133, filed on Jul. 12, 2006.

(51) Int. Cl.
*A61B 5/0402* (2006.01)

(52) U.S. Cl.
USPC ........................................ 600/516; 600/509

(58) Field of Classification Search
USPC ................................................ 600/509, 516
See application file for complete search history.

(56) References Cited

U.S. PATENT DOCUMENTS

| | | | |
|---|---|---|---|
| 3,867,950 | A | 2/1975 | Fischell |
| 3,888,260 | A | 6/1975 | Fischell |
| 4,003,379 | A | 1/1977 | Ellinwood, Jr. |
| 4,223,678 | A | 9/1980 | Langer et al. |
| 4,295,474 | A | 10/1981 | Fischell |
| 4,373,527 | A | 2/1983 | Fischell |
| 4,543,955 | A | 10/1985 | Schroeppel |
| 4,658,830 | A | 4/1987 | Sarnoff |
| 4,796,641 | A | 1/1989 | Mills et al. |
| 4,905,707 | A | 3/1990 | Davies et al. |
| 5,042,497 | A | 8/1991 | Shapland |
| 5,113,869 | A | 5/1992 | Nappholz et al. |

(Continued)

OTHER PUBLICATIONS

Warnecke, H., et al., "Clinical Heart Transplantation without Routine Endomyocardial Biopsy", The Journal of Heart and Lung Transplantation, vol. 11, No. 6, Nov./Dec. 1992, pp. 1093-1102.

(Continued)

*Primary Examiner* — Carl H Layno
*Assistant Examiner* — Jennifer Ghand
(74) *Attorney, Agent, or Firm* — Morton J. Rosenberg

(57) ABSTRACT

A system for the detection of cardiac events occurring in a human patient is disclosed to include at least two electrodes for obtaining an electrical signal from a patient's heart. At least two electrodes are included in the system for obtaining an electrical signal from a patient's heart. An electrical signal processor is electrically coupled to the electrodes for processing the electrical signal. The system determines the presence of a cardiovascular condition by applying a sliding scale rule to heart signal feature values. When the cardiovascular condition is ischemia, the ST segment may be analyzed. A sliding scale is applied to ST segment shifts such that when the magnitudes of ST segment shifts are relatively small, a larger number of beats is required to detect ischemia compared to the case when the magnitudes of ST shifts are large.

13 Claims, 19 Drawing Sheets

(56) References Cited

U.S. PATENT DOCUMENTS

| | | |
|---|---|---|
| 5,135,004 A | 8/1992 | Adams et al. |
| 5,139,028 A | 8/1992 | Steinhaus et al. |
| 5,305,745 A | 4/1994 | Zacouto |
| 5,313,953 A | 5/1994 | Yomtov et al. |
| 5,330,505 A | 7/1994 | Cohen |
| 5,402,794 A | 4/1995 | Wahlstrand et al. |
| 5,404,877 A | 4/1995 | Nolan et al. |
| 5,409,009 A | 4/1995 | Olson |
| 5,411,031 A | 5/1995 | Yomtov |
| 5,417,717 A | 5/1995 | Salo et al. |
| 5,496,351 A | 3/1996 | Plicchi et al. |
| 5,497,780 A | 3/1996 | Zehender |
| 5,531,768 A | 7/1996 | Alferness |
| 5,730,125 A | 3/1998 | Prutchi et al. |
| 5,792,066 A | 8/1998 | Kwong |
| 5,800,498 A | 9/1998 | Obino et al. |
| 5,876,353 A | 3/1999 | Riff |
| 6,112,116 A | 8/2000 | Fischell et al. |
| 6,128,526 A | 10/2000 | Stadler et al. |
| 6,230,049 B1 | 5/2001 | Fischell et al. |
| 6,272,379 B1 | 8/2001 | Fischell et al. |
| 6,368,284 B1 | 4/2002 | Bardy |
| 6,468,263 B1 | 10/2002 | Fischell et al. |
| 6,501,983 B1 | 12/2002 | Natarajanl et al. |
| 6,609,023 B1 | 8/2003 | Fischell et al. |
| 6,741,885 B1 | 5/2004 | Park et al. |
| 6,804,555 B2 | 10/2004 | Warkentin |
| 6,980,851 B2 | 12/2005 | Zhu et al. |
| 6,985,771 B2 | 1/2006 | Fischell et al. |
| 7,054,679 B2 | 5/2006 | Hirsh |
| 2003/0045805 A1* | 3/2003 | Sheldon et al. ............... 600/513 |
| 2004/0059238 A1* | 3/2004 | Fischell et al. ............... 600/515 |
| 2004/0088017 A1* | 5/2004 | Sharma et al. ................ 607/25 |
| 2005/0113705 A1 | 5/2005 | Fischell et al. |
| 2005/0177049 A1 | 8/2005 | Hardahl et al. |
| 2006/0009811 A1* | 1/2006 | Sheldon et al. ............... 607/17 |
| 2006/0064136 A1 | 3/2006 | Wang |

OTHER PUBLICATIONS

Knosalla, C., et al., "Intramyocardial Electrogram Recordings (IMEG) for Diagnosis of Cellular and Humoral Mediated Cardiac Allograft Rejection", Annals of Thoracic and Cardiovascular Surgery (ATCS), vol. 6, No. 2, 2000, pp. 89-94.

* cited by examiner

Table #1: Example of a segmentation-based protocol.

| Parameter Class | Parameter | Parameter value |
|---|---|---|
| Sensor | Sensor 1 | 1 (on) |
| Sensor | Sensor 2 | 0 (off) |
| Partitioning | # beats | 10 |
| Partitioning | Duration | 0 |
| Partitioning | # sequential | 3 |
| Partitioning | Inter-partition-time | 2 seconds |
| Partitioning | # partions/5 minutes | 3 |
| Feature extraction 1 | ST-Down (intra) | 1 |
| Feature extraction 2 | ST-Up (intra) | 1 |
| Feature extraction 3 | ST-variance(inter) | 1 |
| Feature extraction 4 | QRS-complexity | 0 |
| Feature extraction 5 | SUM QRS | 0 |
| Cardiac Segment Score 1 | Threshold ST-Dwn (0,1) | > 0.5 mV |
| Cardiac Segment Score 2 | Threshold ST-Down (0,1) | > 1.0 mV |
| Cardiac Segment Score 3 | Threshold ST-Up (0,1) | < 0.5 mV |
| Cardiac Segment Score 4 | Threshold st-variance (0,1) | <2 m.v. |
| Cardiac Segment Score 5 | CSS1 and CSS4 | 2 (both true) |
| Cardiac Segment Score 6 | Not used | -- |
| Diagnostic rule 1 (0,1) | CSS1-duration | 6 segments |
| Diagnostic rule 2 (0,1) | CSS2-duration | 3 segments |
| Diagnostic rule 3 (0,1) | CSS3-duration | 12 segments |

FIG. 13a

Table #2

| Segment score rule | Segment 1 | Segment 2 | Segment 3 | Segment N |
|---|---|---|---|---|
| St-dev (lead1, intra) | 3 | 3 | 5 | ... |
| QRS complexity (lead1, intra) | 0 | 2 | 0 | ... |
| St-dev (lead2, intra) | 4 | 3 | 5 | ... |
| QRS complexity (lead2, intra) | 0 | 1 | 0 | ... |
| Avg. St-dev (lead1, inter) | 1 | 0 | 1 | ... |
| Avg. QRS complexity (lead1, inter) | 0 | 0 | 0 | ... |
| Avg. St-dev (lead2, inter) | 1 | 1 | 1 | ... |
| Avg. QRS complexity (lead2, inter) | 0 | 0 | 0 | ... |
| SSR1 (st-dev, intra, lead1, lead2) | 1 | 1 | 1 | ... |
| SSR2 (intra-total, lead1, lead2) | 3+4 | 5+4 | 5+5 | ... |
| SSR3 (QRS, intra, lead1, lead2) | 0 | 0 | 0 | ... |
| SSR4 (either SSR1,SSR2) | 1 | 1 | 1 | ... |
| SSR5 (both SSR1,SSR2) | 0 | 0 | 0 | ... |

*SSR (summary score rule).

SSR1 can be at least combined 6 or both must be at least 3 (5 and 1) is too localized and isn't a worry.

FIG. 13b

Table #3: Example of considerations which shape a diagnostic rule.

|  | Normal heart rate (e.g. <+/- 2 sta-d) | High heart rate (e.g.,> 2 +/-sta-d) |
|---|---|---|
| ST-Dev. (or shift) Up | Most likely bad | Probably bad |
| ST-Dev. (or shift) Dwn | May or may not be bad | Most likely due to exercise so likely not bad |

FIG. 13c

SYSTEM AND METHODS FOR SLIDING-SCALE CARDIAC EVENT DETECTION

RELATED U.S. APPLICATION DATA

This application is a continuation-in-part of U.S. patent application Ser. No. 11/710,902 entitled "Systems and Methods of Medical Monitoring According to Patient State filed Sep. 27, 2007", which is based upon U.S. Patent Application No. 60/767,073 to John, entitled "Systems and Strategies for Long-Term Monitoring of Cardiac Status" filed on Mar. 1, 2006 and U.S. Patent Application No. 60/830,133, entitled "Systems and Strategies for Long-Term Monitoring of Cardiac Status" filed on Jul. 12, 2006.

DESCRIPTION & BACKGROUND

This invention is in the field of systems, including devices, implanted within or attached to a human patient, for monitoring biological activity. The invention is preferably applied to the monitoring of cardiac status, providing early detection and/or prediction of unwanted medical conditions and alarming the patient in response thereto.

Implantable devices which monitor and store sensed data and provide alarms when pathological conditions occur will both revolutionize medical care in the near future and also greatly increase our understanding of the physiological and metabolic processes and states that occur in healthy and sick individuals. One obvious area where these devices will have a central role is in the treatment of neurological and cardiac disorders. In the case of cardiac disorders, the ability to monitor, detect, and predict cardiac abnormalities related to, for example, ischemic factors will decrease the fatalities related to these disorders by providing patients with sufficient prior warning to allow them to obtain treatment or intervention prior to having a fatal heart attack. Fischell et al in U.S. Pat. Nos. 6,112,116, 6,272,379, 6,468,263, 6,609,023 and 6,985,771 which are incorporated herein by reference, describe such systems for acute detection and warning, however, these do not provide comprehensively for measuring and storing data related to trends of cardiovascular health over extended periods of time. Other relevant prior art are U.S. Pat. Nos. 6,980,851 6,741,885 and US applications 2005/0177049, 2003/0083582 and 2003/0004548, which describe measurement and storage of cardiac data, and also describe providing alarms in response to detection of abnormal events.

While coronary narrowing or blockage (e.g., atherosclerosis, thrombosis, and stenosis) can be treated by angioplasty and the introduction of cardiac stents, subsequent monitoring, after surgical or other type of intervention, would be useful in order to ensure that the effects of an intervention continue to be sufficient. Further, in interventions such as heart replacement, or implantation of a pacing or defibrillation device, follow-up monitoring can provide an ongoing indication that the procedure is having its intended effects. The monitoring system can provide alarm warnings when sensed data indicate that the intervention has become inadequate to deter abnormal cardiac activity. Monitoring of operations of implanted devices (e.g., amount of drug or stimulation delivered over a specified duration), and biological activity which is time-locked to operations of these implanted devices (e.g., post-stimulation activity), and ongoing endogenous biological activity may all be monitored. For example, an increase in the occurrence of responsive therapy, such a pacing therapy, over time may indicate that the heart is getting sicker or that pacing is losing its efficacy.

Fischell et al. in U.S. Pat. No. 6,272,379 discloses an implantable cardiac monitor that can detect ischemia by evaluating the ST segment of a patient's electrogram. Specifically, the ST segment deviation is compared to a threshold, which may be programmed before and/or after the device is implanted within a patient. It may be desirable to improve upon the algorithms disclosed in the '379 patent.

Fischell et al. in US Patent Application 2005/0113705 describes a cardiotracker system which allows for extended recording of cardiac data by transforming the time-series cardiac data into histograms which summarize the cumulative frequency and distribution of various measures of the electrogram. Trending of data and generation of summary results are also described. The '705 application also discloses alerting for predicted future events based on a combination of a recent trend for a parameter (e.g., the rate of change of a parameter over a prior period) and the current level of the parameter. As such greater rates of change may result in an alert being issued at an earlier time than the occurrence of the future event. The absolute level of a parameter is a function of the rate of change of that parameter.

SUMMARY OF THE INVENTION

The invention described herein relates to medical devices for monitoring biological activity. More particularly it describes a system incorporating a device capable of sensing and recording long segments of biological activity, providing early detection and/or prediction of medical conditions and possibly alarming the patient in response thereto. When the invention is preferably applied to the monitoring of cardiac status it is referred to as the "CardioTrend system".

The present invention includes a patient monitor that is operated according to a control program. The control program can cause operations to occur in response to a "monitoring result" provided by a "diagnostic module", in response to a timing signal such as time of day, in response to monitored data, based upon control laws, and/or in other manners as well.

The present invention preferably includes a diagnostic module with methods for detection, control, and classification of cardiac events. These methods can use two or more measures of cardiac activity which are computed by modules embodied within the diagnostic module in the detection of cardiac events. The diagnostic module preferably employs methods that determine if, how, and when to provide one or more types of alarm warning, intervention (e.g. therapy), and/or storage of data.

According to one embodiment, the diagnostic module detects ischemia by analyzing ST segment changes. The diagnostic module computes the ST deviation for each beat in an electrogram. The diagnostic module categorizes the ST deviations by applying thresholding operators to determine the number of beats in the electrogram segment that exceeded first and second thresholds $H_1$ and $H_2$, corresponding to small and large ST shifts, respectively. Thresholds $H_1$ and $H_2$, which are thresholding operator parameters, are preferably programmable. The number of beats that exceeded $H_1$ and $H_2$, respectively, is then computed. The number of supra-threshold beats will be referred to as $M_1$ and $M_2$. $M_1$ and $M_2$, which may be considered cardiac state parameters, are stored within the diagnostic module. While this example uses 2 thresholds, any number are possible.

The diagnostic module analyzes the $M_1$ and $M_2$ data of the current electrogram segment and any number (N, where N is between 0 and 100) of prior electrogram segments to generate an ischemia score that is indicative of whether a patient has ischemia. The ischemia score is based on a sliding scale rule that trades off the magnitude of ST shifts against their duration. Thus, ischemia may be detected with relatively few beats with larger ST shifts exceed a first threshold ($M_2$) or relatively more beats with smaller ST shifts beats exceed a second threshold ($M_1$), or a combination of these two. The speed of onset of the emergence of ST shift, or 'growth curve', may also be used to adjust the detection algorithm.

BRIEF DESCRIPTION OF THE DRAWINGS

For the purpose of illustrating the invention and its advantages, there is provided a detailed description and accompanying drawings of embodiments which are presently preferred. In illustrations of methods, when arrows indicate iteration (a return from later steps to prior steps), this iteration is understood to be a preferred embodiment, and executing the steps a single time may also be an option. In the illustration of methods, steps which occur sequentially may also occur concurrently, in parallel, or may be repeated several times (e.g., in order to obtain an estimation of a measure by computing a statistic such as the mean), prior to the next step occurring. In illustrations of systems, when lines contain arrow heads on both ends, this signifies that information may regularly travel in both directions. It is understood that the invention is not intended to be limited to the precise arrangements and instruments shown, wherein.

DETAILED DESCRIPTION OF THE INVENTION

In the following description, the term "module" refers to electronics, software programs, communication, operations, algorithms, methods and strategies related to accomplishing the task of that module. Although modules are illustrated as isolated, the components of the modules can be distributed, and may operationally rely upon components of other modules.

A "patient state value" pertains to the physiological, emotional, mental, behavioral, periodic (e.g., circadian), or environmental state of a patient. "Patient state values" include, without limitation, a patient's mental state (e.g. angry, confused, etc.), behavioral state (e.g. walking, supine, sleeping etc.), time of day in relation to patient activity, patient input using an external controller, evaluation of sensed data related to body temperature, blood pressure, or other available measures. In a particular embodiment, "patient state values" may also include heart related features such as heart rate, the presence of arrhythmias, as well as acoustic or chemical measures related to cardiac function, which may be obtained.

"Heart signal features" are defined to be any measured or calculated value created during the processing of data for one or more beats, especially as reflected in any type of electromagnetic signal, such as an electrogram (or electrocardiogram), that reflects the electrical activity of a heart. Heart signal features include PQ segment average voltage, ST segment average voltage, R wave peak voltage, ST deviation (e.g., ST segment average voltage minus PQ segment average voltage), ST shift (e.g., ST deviation compared to a baseline average ST deviation taken at some prior time), average signal strength, T wave peak height, T wave average voltage, T wave deviation, QRS complex width, QRS voltage, heart rate and R-R interval. ST segment related heart signal parameters include ST segment average voltage, ST deviation, and ST shift.

Cardiotrend System

Figure 1A:
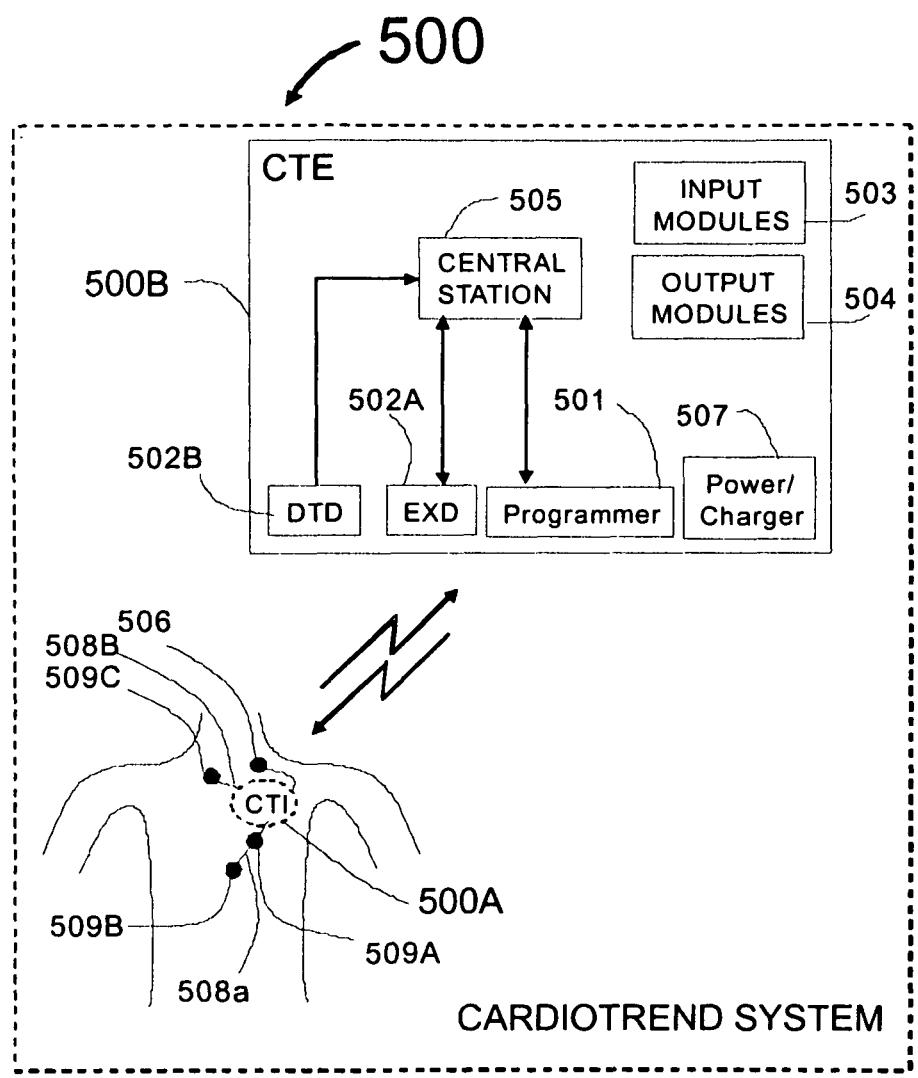
FIG. 1A illustrates a schematic representation of a preferred embodiment of the CardioTrend comprising an implantable system and an external system.

FIG. 1A illustrates one embodiment of the cardiotrend system 500, which contains an implantable system (CTI) 500A and an external system (CTE) 500B, although the system can be realized completely or approximately as either of these. Even when most of the system 500 is located external to the patient, the CTE 500B may communicate with and/or control generic implanted detection and/or stimulation devices. The CTE 500B may include a pager type external device (EXD) 502A, which may be partially attached to the patient's skin, for example, using a patch, and can have intra- or trans-dermal components, for example, electrodes. The EXD 502A may also be worn by the patient and can allow patient input in response to alarms or to modify operation and may also display messages from the CTI 500A. The EXD 502A would typically include patient alerting capabilities (vibratory, acoustic or visual) and could be designed to include cellular or wireless voice and data capabilities. The EXD 502A will typically communicate with the CTI 500A using bidirectional wireless radiofrequency transmission, and may be used to provide the CTI 500A with operator parameters to customize the CTI 500A, as will be further described below.

When most of the system 500 is implanted, the (CTI) 500A may communicate with the CTE 500B as well as with other implanted devices (not shown). For example, the system 500 can communicate with a physician programmer 501, a portable patient external device (EXD) 502A, or a home patient data transmission device (DTD) 502B which may be a limited version of the physician programmer 501. The programmer 501, EXD 502A and DTD 502B may have an input module 503 that may include a keyboard, mice, various control buttons, microphones and communication transceivers (e.g., telemetry circuitry) hardware. The programmer, EXD 502A and DTD 502B may have an output module 504 that may include various displays, alarm transducers, a (wireless) modem, and other communication equipment. The programmer 501, EXD 502A, and DTD 502B can communicate with a central station 505, which may be fully automated or may include a staff of medical personnel who can assist the patient if the system 500 has alerted the patient that medically significant activity has been detected.

Figure 1B:
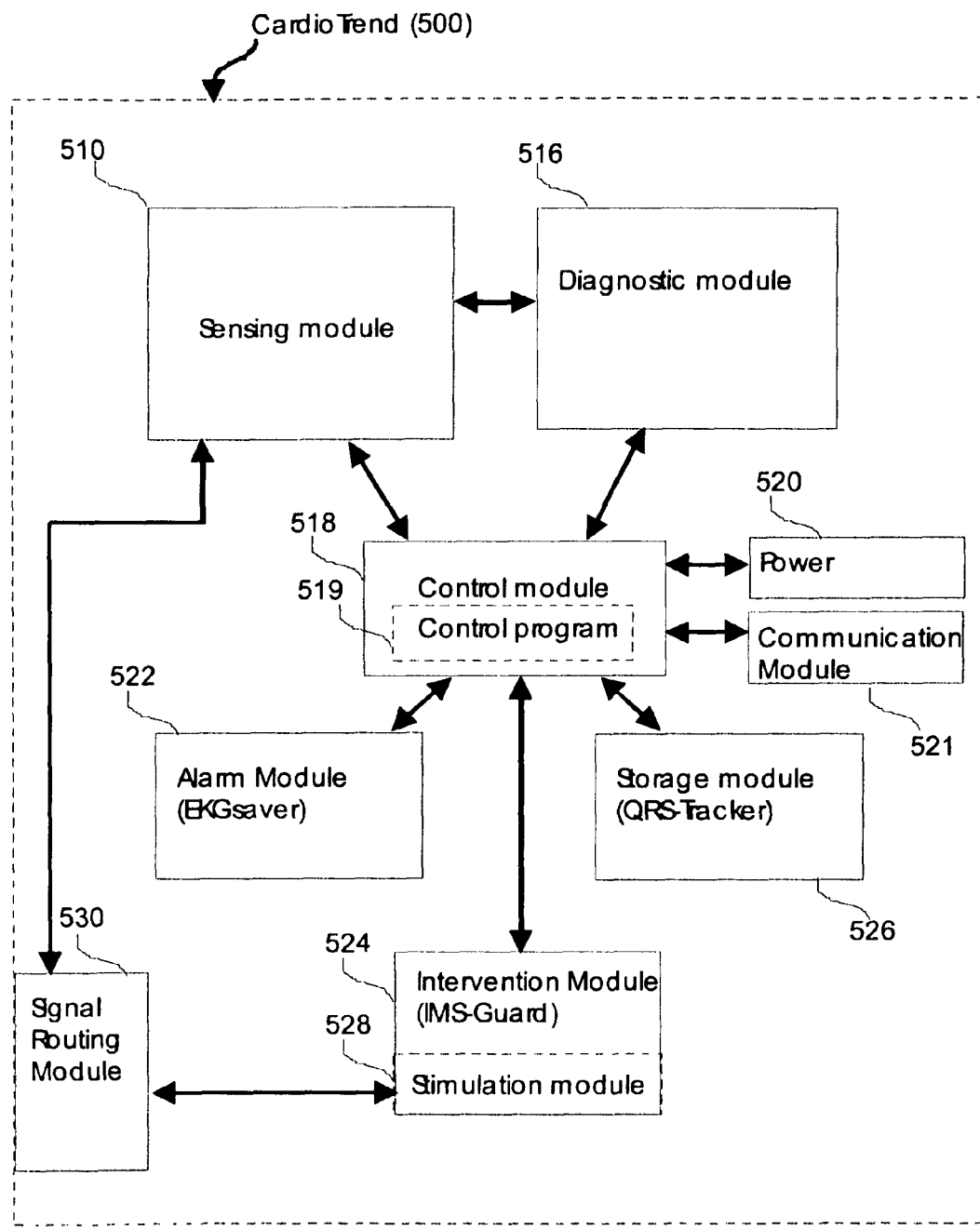
FIG. 1B illustrates a schematic representation of a preferred embodiment of the CardioTrend system and its modules.

Power and charging equipment 507 can charge both the rechargeable power supply 520 of the CTI 500A shown in FIG. 1B and can recharge and/or supply power directly to CTE 500B components. The system can utilize sensors 506 and stimulation conduits 508A. When the sensor and stimulation conduit are both electrical, these can be realized in the same structure. For example, when a stimulation conduit 508A is a lead with contacts 509A, 509B, or 509C of a different lead 508B, then this can be connected to the stimulation module 528 shown in FIG. 1B via the signal routing module 530. When the contacts 509A, 509B and 509C are used to sense data, these can be connected to the sensing module 510 shown in FIG. 1B, via the signal routing module 530.

Other sensors, such as 506, which may sense optical, chemical, or thermal data or acceleration, flow rates, impedance, and other measures can also communicate with the sensing module 510 through the signal routing module 530. The sensed data can come from electrical contacts and sensors located external to the housing of an implanted device, or may be derived from components such as an accelerometer or thermometer which are located either within or outside of the housing, and which provide signals to the sensing module 510 as may occur using the signal routing module 530.

FIG. 1B illustrates in block diagram form an embodiment of the cardiotrend system 500, which includes a sensing module 510, a storage module 526 with an associated random access memory, a diagnostic module 516, a control module 518, an alarm module 522, a signal routing module 530 an intervention module 524, a stimulation module 528, a communication module 521, and a power supply 520. The control module 518, diagnostic module 516, storage module 526 will typically be implemented by a digital processor (or different digital processors) and associated software. The sensing module 510 controls the sensing of signals (including patient state related data) from the human patient and typically includes amplifiers, multiplexers, and other electronic circuitry related to communication with the sensors 506 and contacts 509A, 509B and 509C. The diagnostic module 516 is designed to analyze monitored data including sensed data provided by the sensing module 510, as well as data from the storage module 526 in order to produce "monitoring results" which are used by the control program 519 of the control module 518 to responsively provide alerting or other CardioTrend operations. The control module 518 and the rest of the cardiotrend system 500 is powered by the power supply 520 which may be a rechargeable battery. The system 500 communicates with other implanted devices and the external system (CTE) 500B using its communication module 521.

As mentioned above, the EXD 502A may be used to provide the CTI 500A with operator (function) parameters to customize the CTI 500A. These operator (function) parameters may be stored by the storage module 526.

The Control Module.

The control module 518 is designed to control the operation of the cardiotrend system 500 including the diagnostic module 516, the alarm module 522, intervention module 524, and storage module 526 based upon the control program 519. Operation and control of the various modules of the cardiotrend system 500 are termed cardiotrend operations (CTOs), which are operations involving sensing, alarm, intervention, diagnostics, communication, storage, or other operation carried out by the cardiotrend system 500. CTO's can be accomplished either by the control module 518 controlling the other modules of the system 500 directly or by the other modules acting independently under instructions from the control module 518. The operations accomplished by the control program 519 of the control module 518, can be triggered or modified in response to one or more "monitoring results" provided by a diagnostic module 516, or due to commands sent by the programmer 501, EXD 502A or DTD 502B of FIG. 1A. The CTOs may also be triggered or modified in response to times which may be defined in the control program 519. When the invention is primarily oriented towards treatment of cardiac disorders, as is the case in the cardiotrend system 500, the alarm 522, intervention 524, and storage 526 modules are specifically designed to monitor cardiac activity and exist in preferred embodiments known for the purposes of the present invention as the 'EKGsaver', 'IMS-Guard', and 'QRSTracker' (or 'QRS-Tracker'), respectively. The acronym IMS, stands for implanted medical system.

The control module 518 coordinates the acquisition and use of patient state related data. Under the control of the control module 518, patient state data (e.g. a button press) is stored in the storage module 526 in a patient state array, as will be further described below. Again under the control of the control module 518, patient state data stored in the storage module 526 is utilized by a patient state module (568a in FIG. 3) that is part of the diagnostic module 516, which determines a patient state index, as will be further described below. The patient state index, in turn, modulates the operation of a variety of CTOs through the operation of the control module 518.

The Sensing Module.

Figure 2:
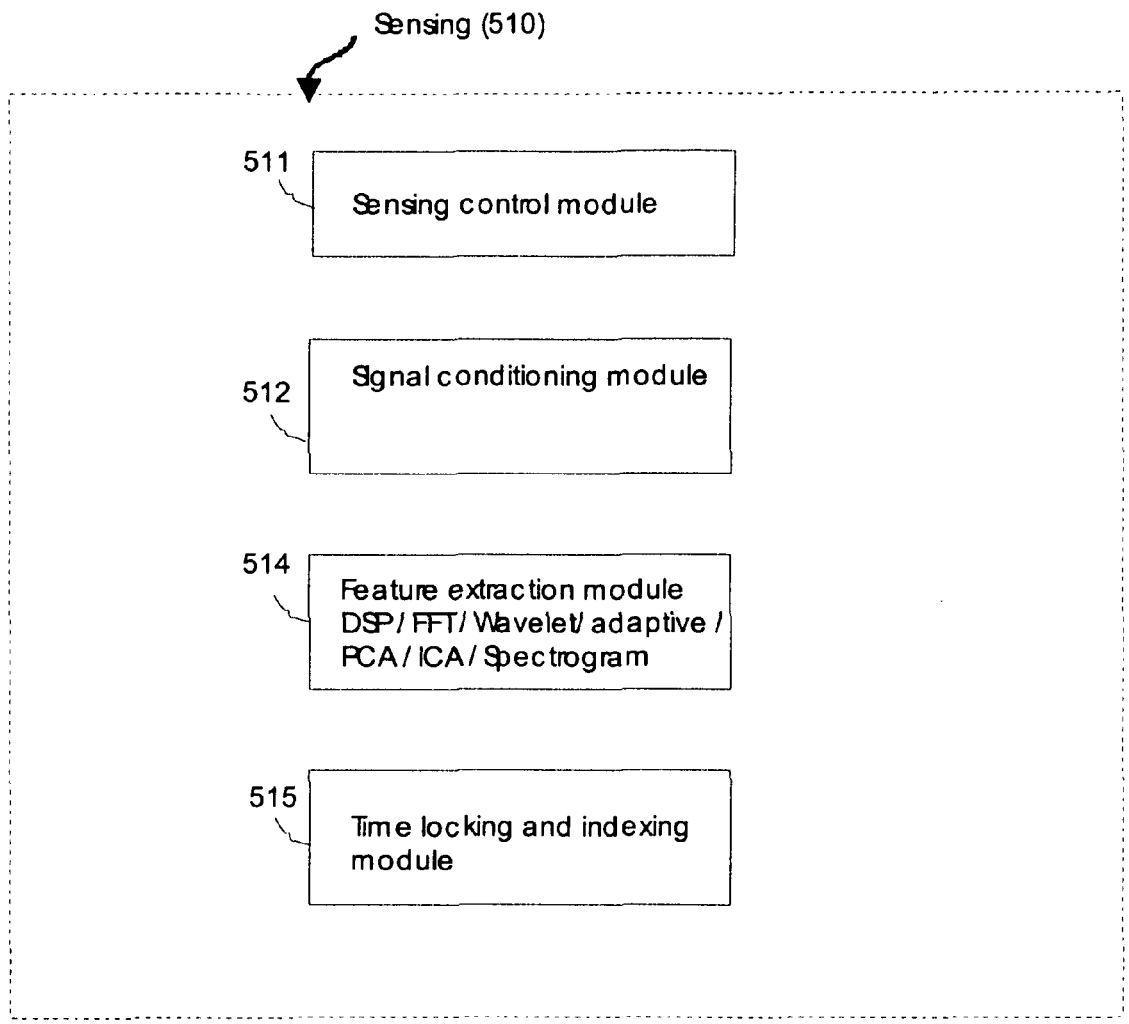
FIG. 2 shows a preferred embodiment of the sensing module.

The sensing module 510, shown in FIG. 2, obtains sensed data and processes it via the signal conditioning module 512. As mentioned, sensed data can include many different types of data, including data related to a patient's state. The signal conditioning module 512 typically includes analog and digital signal processing circuits such as programmable filters. The signal conditioning module 512 can amplify and filter the incoming data as these are sensed. The same data can then be further conditioned in various manners (e.g., submitted to different band-pass filters or signal processing such as averaging, PCA, or ICA) prior to being submitted to different types of feature extraction. For example, R-R interval may be best measured after high pass filtering the incoming data with a cut off frequency of 2 Hz or greater, while ST segment voltage measurements require a high pass filter with cut off frequency below 1 Hz. The module 510 can temporally segment the incoming data, prior to, concurrently with, or after, conditioning it using filtering and amplification schemes. Since filtering may distort the data, for example by smoothing adjacent components according to the time-constants of different filters, conditioning these components separately may decrease this type of distortion. The output of the signal conditioning can be sent to the feature extraction module 514 for detection and measurement of relevant features of the data.

The feature extraction module 514 typically includes time, time-frequency, and frequency measurement algorithms which may be used to measure specific features of the sensed signals from the human patient. When these sensed signals are related to cardiac activity, the features which are measured may include heart signal parameters from an electrogram (e.g., using implanted electrodes), the electrocardiogram (ECG, obtained, for example, using subdermally or skin surface mounted electrodes), or a sonogram. Specifically, the feature extraction module 514 can provide temporal analysis, frequency analysis (e.g., FFT, filtering, or adaptive filtering), and time-frequency analysis (e.g., spectrogram, wavelet analysis) methods for analyzing cardiac activity and providing detection of cardiac abnormalities. Temporal analysis can include automatic peak-picking and template matching algorithms which detect and measure components of the monitored activity such as the p-wave or ST segment.

The feature extraction module 514 can analyze both continuous and time-locked data. A specialized time-locking and indexing module 515, permits time-locking to occur. For example, data windowing can be triggered by stimulation of the heart as may occur in the cardiotrend system or due to pacing of a generic implanted device, e.g. a pacemaker. Data windowing can also be locked to other cardiotrend operations such as delivery of an electrical or drug therapy provided by stimulation module 528. Alternatively, the module 515, can enable continuous cardiac data to be windowed (i.e., aligned), based upon some feature, such as the R-wave peak, in order to provide time locking in relation to this component of the signal. Time-locking techniques can enable more stable quantification of the spectral characteristics of the sensed signals, than when time-locking is not used. Further, appropriate pre-processing and windowing of the data can counter some of the difficulties inherent in measuring a variable R-R interval which may not fit well into selected data segments (e.g., Clifford et al., 2005; Singh et al., 2005). The module 515 also permits for the indexing of data records, for example, according to different states of the sensed data (e.g., normal/abnormal) or the patient (awake/asleep), so that the data may be stored in a manner that permits these to be indexed as belonging to 1 or more categories. For example, if the state-module 568 of the diagnostic module 516 of FIG. 3, determines that the patient is awake or asleep, then the control module 518 can send a command to the time-locking and indexing module 515, so that the incoming sensed data can be "tagged" with an appropriate index value, which can be used to adjust the subsequent storage or analysis of the data.

In addition to time-to-frequency conversion, using for example an FFT, frequency-to-time conversion is also possible (e.g., IFFT) as provided in the feature extraction module 514. These two types of analysis can provide increased detection of abnormal activity using a number of methods. One general method of increasing detection of abnormal events by improving SNR levels of the data, or simply removing spectral content of components which are unrelated to those being measured, may comprise the steps of: performing time-to-frequency transformation; altering the spectral data based upon some type of analysis of the spectral data, performing frequency-to-time transformation; and, measuring components of cardiac activity in the time domain.

One embodiment of this method includes computing the phase variance across a set of cardiac data (e.g., a set of cardiac waveforms, or sub-averages of cardiac waveforms) for individual spectral bins created by the time-to-frequency transformation, sorting the bins with phase variance which is below a specified value into a stable set, performing inverse-FFT on the stable set, and measuring selected features of the signal in the time domain. This type of technique can be useful in improving the signal-to-noise characteristics of stable signal components, and can be useful when electrodes are on the surface of the skin. When the electrodes record the electrogram from implanted electrodes, this type of method can be useful for detecting stability and changes in the data.

The method may also include sorting those bins with phase variance above a specified value into an unstable set. This allows for comparison between the spectral components of the stable and unstable sets. Further, after IFFT, this method may allow for measuring selected features of the signal in the time domain, and comparing the temporal features of the stable set and unstable set. As is well known, many types of analysis are improved by analyses in the spectral domain without transformation back into the time domain. Detection of abnormal events can be greatly improved over that which is possible in the time domain when spectral signatures of these events are more easily measured, such as shifts of power and/or phase measures or the variability of these measures. A simple example is that of a shift in R-R variability which would be represented, in part, as a change in the spectral signature (e.g., width of spectral bins) into which this power would be distributed.

In addition to the utilization of spectral analysis, including coherence analysis, bi-spectral index measures, and time-frequency analysis, the feature extraction module 514 can provide the cardiotrend system with a number of additional benefits not found in prior instrumentation. In addition to providing valuable indices of cardiac status, spectral profiles of cardiac state are, similar to histogram representations of cardiac data, a very efficient method of compressing data. The use of spectral data, such as the average long-term power spectra (with statistical measures of variability such as confidence limits) can be used to efficiently represent, detect, and store normal and abnormal activity. Further, the relevant features of the spectral measurements can be stored as reference data in the storage module 526 and used by a reference value module 552 (FIG. 3), and can be in the form of summary statistics or can be formed into histogram format, using the histogram module 654, for efficient storage.

The sensing module 510 also includes a partitioning module 517 that performs data partitioning, as will be further described below.

The Diagnostic Module.

Figure 3:
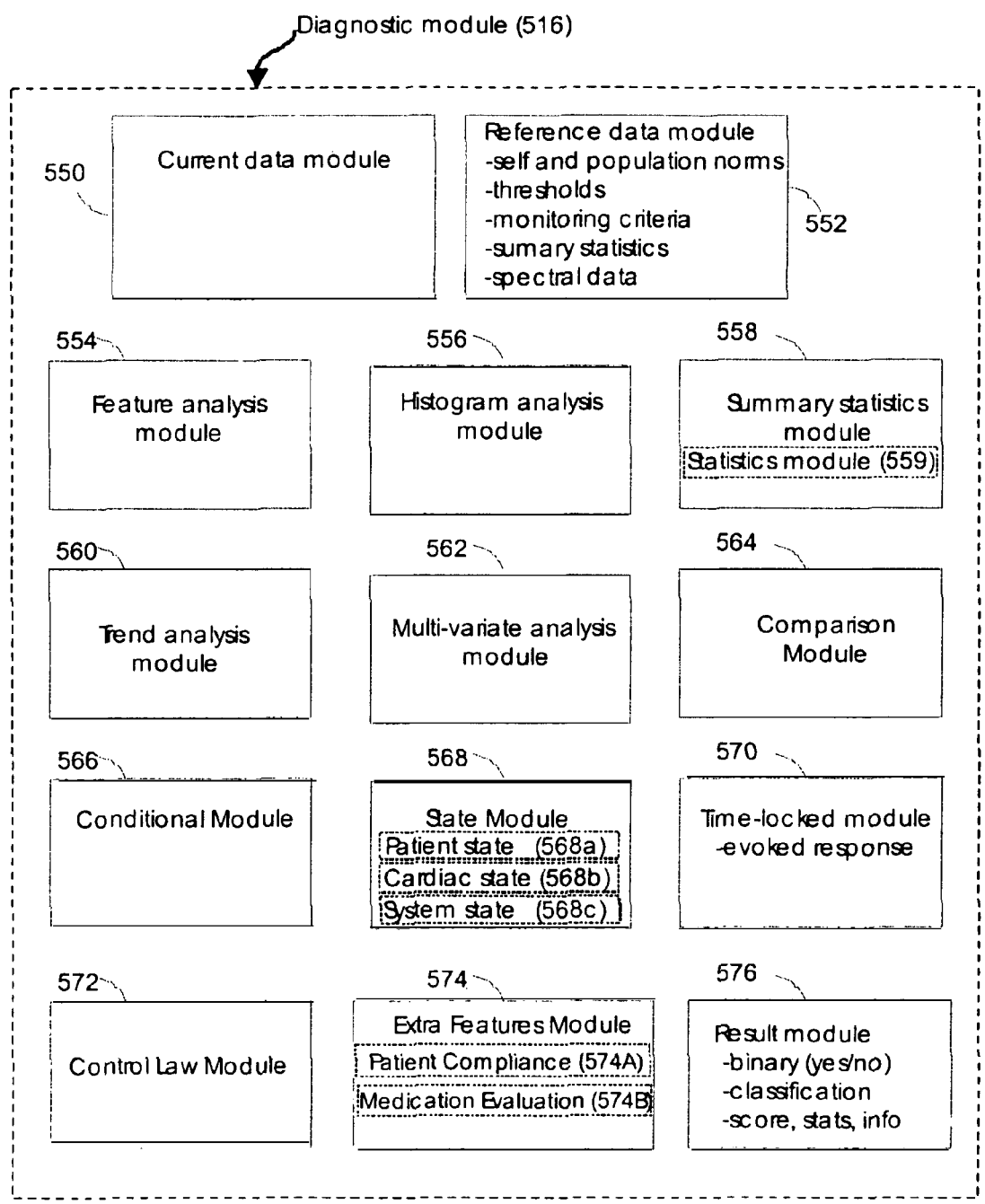
FIG. 3 shows a preferred embodiment of the diagnostic module.

The diagnostic module shown in FIG. 3, is typically used by the cardiotrend system 500 to analyze the data supplied by the sensing module 510 which is managed by the current data module 550, and/or stored data (including operator/function parameters) from the storage module 526. The stored data are processed by the reference value module 552 in order to provide monitoring results via its result module 576. The diagnostic module 516 preferably includes a feature analysis module 554, histogram analysis module 556, summary statistics module 558, trend analysis module 560 can all be used to evaluate data contained within the current data module 550 or reference data module 552.

The comparison module 564 can be used to compare (e.g., using a statistical comparison) current data to a specific reference value or to any reference data in the reference data module 552. Comparisons can be made with respect to a monitoring criterion such as a pre-set threshold value which may be a statistical criterion. The outcome of this comparison provides a monitoring result. If the comparison is statistical, then this can occur using the statistics module 559, which is located in the summary statistics module 558 which is designed to provide statistical computational functionality to any of the other modules of the system 500. For example, the comparison module 564 can compare the current average ST interval voltage of a current segment of data to values computed upon data measured earlier during a baseline data collection period (e.g., a self norm) in order to determine if an ST elevation event has occurred.

The statistics module 559 and/or multivariate module 562 can allow future values to be projected or forecasted values derived from past data using equations derived from associative or regression analysis. This type of analyses would normally have been done previously offline and the derived equations would have been loaded into the multivariate module 562, although some simple adjustments might be made from time to time by the statistics 559 module. Such an example is predicting the size of an ST segment deviation based upon a measurement of the Q wave (e.g. size) that preceded it, measuring the size of an ST segment deviation, and comparing the predicted to measured values, wherein a difference which is greater than a selected amount is indicative of an abnormal event. Another example, where predictive modeling is used to detect cardiac abnormalities would be a method which evaluates the time series data in the latency region of the Q wave based upon the detection of the P wave, in order to see if the observed and expected activity match, or fail to match, with respect to one or more features.

If the comparison is statistical, then the current average ST interval voltage can be transformed to a z-score using the mean and standard deviation of relevant reference data provided by the summary statistics module 558. The current ST interval can also be compared to the bootstrap confidence limits, for a specified statistical level, that were created by re-sampling the amplitudes of ST reference data. The comparison module 564 may compare current data to reference data, using monitoring criteria which result in different CTOs. For example, monitoring criteria can include treatment/intervention criteria, alarm criteria, and storage criteria, and when any of these criteria are not met, then a contingent operation occurs in the respective module. The evaluation of the feature, histogram, or summary statistics data, by their respective modules 554, 556, 558, can occur according to these different types of monitoring criteria as well.

The feature extraction module 514 and feature module 554 can both rely upon calibration coefficients stored in the reference data module 552 in order to adjust for, or scale sensed data by, differences which exist or emerge due to orientation of the sensors, impedance differences in the tissue/sensor coupling, or other factors. The calibration coefficients can be determined by a physician during a calibration procedure, and can be generated semi- or fully-automatically as is provided by the calibration routines of the control program 519 of the control module 518. As well as absolute magnitude, the calibration coefficients can be related to relative magnitude between two channels, phase information, and sign (e.g., +/−) in order to scale or otherwise adjust the monitored data so that these approximate the data expected by the cardiotrend system 500 (i.e. so that the data approximates that which was used during the design of the detection algorithms). The calibration coefficients can be determined, in part, by an algorithm which compares a monitored heartbeat to a prototype heartbeat template, and adjusts, or allows a physician to adjust, the coefficients in order to decrease the difference between the expected and recorded activity. Calibration coefficients can also be applied to the gain/filter settings of the signal conditional module 512.

The use of statistics by the comparison module 564, which can occur in selected embodiments of the diagnostic module 516, may be an advantageous in certain cases compared to schemes that use percentage increase or decrease without consideration of the variance of each measure. For example, an increase of 10% is more meaningful when the distribution of the variance is more tightly distributed around the mean value than when there is a larger distribution. By computing statistics on the reference data in order to determine the central tendency and range, for example, using bootstrap confidence limits (the bootstrap mean and 95% confidence interval can be computed), the comparison that is performed by module 564 can indicate the statistical probability that a change (e.g., increase or decrease) did not occur by chance. If re-sampling is performed upon both present and reference data, then the two histograms can be statistically compared in order to determine if there is a difference between the re-sampled means or distributions of current sensed data and the reference data.

The reference data can be self- or population-normative data. Self-norm data are obtained from the patient during one or more previous periods, and serve as reference data to which sensed data can be compared. Population-normative data are usually data which are collected from members of the population who are appropriately matched to the patient in terms of sex, age, weight, medication, and/or other variables which cause their data to be appropriate for comparison with the data of the patient. The normative data can be collected during a normal patient state, or during an abnormal patient state such as during a balloon-induced occlusion which occurs as part of an angioplasty procedure, or during an occlusion which occurs prior to the surgical or medical intervention. It is understood that if the reference data are collected during an abnormal patient state, then in a general embodiment the cardiotrend system can send warnings when a feature of the current data enters a range defined by this abnormal state, rather than being designed to warn when a feature departs from a range calculated from a normal state. The different types of reference data can also be used in classification procedures described later. Data acquired during different patient states may be stored and tagged with the appropriate patient state value (e.g. normal state or "recent exercise") to enable the comparisons of current data to state appropriate reference data values.

A conditional module 566 can determine if one or more conditional criteria have been met. For example, the module can determine if a certain feature having at least a selected magnitude has lasted at least a specified duration. The conditional module 566 can selectively reduce the number of alerts which might otherwise occur without this module and can enable the physician to put restrictions on what is considered a detectable medical event. For example, if the ST elevation increases 10% above a specified threshold, but only for 2 or 3 beats, then this may be defined as not long enough to cause the alert to occur, whereas if the elevation is 3 times as large, the duration restriction may be less. The conditional module may also prevent the detection of an event from causing an alert to be triggered if an alert has recently been issued, unless 1 or more criteria have been met, such as an increase in the size of this latter event being above a specified level.

A time-locked module 570 can evaluate sensed data which has been collected in relation to the time elapsed from an intervention such as pacing or defibrillation. The time-locked module can window sensed data so that its components are consistent with respect to the analysis window. For example, data can be averaged with respect to a peak component of the signal such as the R-wave maximum. In this case, the R-wave peak of 2 or more heartbeats are found and the time waveforms are windowed from 200 msec before this time-point to 400 msec afterwards. The two waveforms are then each submitted to signal processing such as spectral analysis or averaging. By windowing, aligning, and/or measuring the time waveforms with respect to a specific feature of the waveform many advantages can be obtained. Spectral or spectrogram profiles can be obtained which have similar phase signatures when the components of the heartbeats are similar. This will be true even if there is variability in the inter-beat interval since the analysis can be locked to the components themselves. The use of spectral analysis is of great utility because it is computationally rapid, automatic, and does not require much computational resources due to specialized algorithms or chips. As long as components of the heart activity are time-locked with respect to the analysis window, then phase information, including variability, can be used to automatically detect relevant changes in the heart activity.

A control law module 572 operates according to a set of control laws to create a control signal based upon the sensed data, and this control signal can be used to modify the operation of the alarm 522 or intervention 524 modules. The cardiotrend system 500 may be operated as a control system, in which the issuance of an alarm provides a responsive intervention (e.g., taking of a drug in response to an alarm, or providing data for analysis which will then lead to a specific intervention) which ultimately serves to control the state of the cardiac system (i.e., to maintain the system within specified limits) albeit with a delay which may vary from minutes to much longer. The control law module 572 allows the system 500 to act as a system for providing cardiac monitoring that leads to alerting or direct modulation of activity in the treatment of disease and in order to keep selected activity within a specified range. The system 500 may use a number of modules to realize the control law including: a signal conditioning circuit 510 and a sensor array (e.g. 509) in electronic communication with said signal conditioning circuit 510; a signal processor such as the control module 518 is in electronic communication with said signal conditioning circuit, and the signal processor can perform cardiac state estimation using the control program 519 and either the state module 568 or control law module 572 of the diagnostic module 516. The control module 518 may have a control circuit capable of implementing 1 or more control laws using the software routines of the control law module 572, which is in electronic communication with said signal processor 518. The output stage circuit which is in electronic communication with said control circuit, can include the stimulation module 528 and a stimulation system, having at least one stimulation conduit 508 which is in electronic communication with said output stage circuit, in this case a signal routine module 530. The output stage circuit may also be realized as the alarm module, where the characteristics of the alarm signals are modified based upon the sensed data, such that different features of the data result in the issuance of different alert signals and subsequent intervention on the part of the patient, so that cardiac activity is controlled. The system may be realized using control laws such that one of the following is achieved: cardiac state is controlled to remain within a normal range: cardiac state is controlled to remain within a control range; cardiac state is controlled to remain outside of a borderline range; cardiac state is controlled to remain outside of a critical range; cardiac state is controlled to prevent the occurrence of at least one of abnormal cardiac signs and symptoms; cardiac state is controlled to prevent the occurrence of precursors to at least one of cardiac signs and symptoms related to a disorder; cardiac state is controlled to prevent the occurrence of EKG abnormalities; cardiac chaos is controlled; synchronization of cardiac activity is controlled; cardiac entrainment is controlled; cardiac dis-entrainment is controlled. If the communication module 604 is configured for communicating with an implanted stimulation device (e.g., a pacemaker or drug-pump), or if the cardiotrend system is implemented so as to contain such a device then in addition to, or instead of, alarming the patient cardiac state may be controlled via stimulation.

The result module 576 operates to provide a 'monitoring' or 'diagnostic' result. This result can be binary (i.e., either "yes" or "no"). For example, a yes result can indicate that a pathological symptom (abnormal event) has been detected and an alarm is merited. The result can also be a classification result, which indicates the type of abnormality detected, such as ischemia or tachycardia. The alarm signal can be modified based upon this classification. The result can also be a score or probability. For example, the result can indicate the probability that an abnormal condition has occurred. The result can be comprised of 2 or more values, representing two aspects of the signal, such as providing both a classification of what type of abnormal event has occurred and its severity. The result can lead to different alarms based upon this classification, which can be further modified based upon severity (e.g., the sound pattern of the alarm signal can represent the event types and the speed at which the pattern repeats can indicate the severity).

The alarm warnings can be realized as medical alerts and status messages which generally occur in a fashion that commonly minimizes disturbance of the patient. For example, alerts can use a gentle sonic alarm which increases in volume slowly over time and which can also be a different sound than that used for other types of alarm warnings. Alerts may be triggered by non-critical events, such as the device simply alerting the patient that it is time to take medication. The alerts can include instruction to the patient to take or obtain a selected amount of a specified drug, as may have been prescribed previously by a physician in order to treat that specific abnormality (and programmed into the cardiotrend system by its external physician programmer). The output module 504 of the CTE 500B of FIG. 1A could include a set of pill dispensing containers, one or more of which can be automatically unlocked due to the type of alert warning which occurs. For example, one containment section can be unlocked for an alert which indicates a mild cardiac event, while two can be unlocked if the alarm signal indicates an event is more severe. Different drugs can also be provided for different alert indications as may have been prescribed previously by a physician. In other words, the dispensing of drug by the system in response to alert signals occur as dictated by a doctor's prescription, wherein the physician's programming of the device is equivalent to a prescription. It is also envisioned that the EXD 502A or DTD 502B would contain at least one pill containment section.

The feature analysis module 554 and trend analysis module 560 of the diagnostic module 516 of the cardiotrend system 500 can monitor trends which may occur over time. For example, if over the period of a month there is a slow but steady increase in the number of pacing treatments provided by an implanted device, the trend analysis module 560 can detect this increase in the sensed data and can issue an alert signal. The alert may be triggered, for instance, if a feature of the trend, such as the most current value, or the slope or variability of at least a portion of the trend, exceeds a threshold value. Additionally, just as different cardiac disorders can produce different changes in a subset of features within an individual, or the same disorder can produce different changes in different individuals, the results which occur in response to the type of drug provided to a patient will depend upon the particular drug and amount. Treatment benefit can only be assessed by understanding what type of therapeutic change would occur for a given type of abnormal pattern and according to the type of drug which is given. The physician can therefore program the diagnostic module protocol so that the trend graphs or alarms which are provided are related to drug/patient specific change (e.g., an improvement from an abnormal to normal state is evidenced by a change in particular cardiac features). Unlike the prior art, it is a feature of the present invention to provide the diagnostic module with a medication evaluation module 574B to allow programming of drug response protocols which are oriented towards monitoring the normalization rather than, or in addition to, monitoring for unwanted medical events. In one embodiment, alerts can be triggered when a plateau or worsening, rather than an improvement, is detected in the sensed data.

The detection, quantification, and classification of events in the sensed data can occur by simply measuring features of the sensed data or by further comparing these to reference data. For example, the comparison module 564 can compare the data of the current data module 550 to reference data of the reference value module 552 using statistics to provide a probability of detection or classification of a certain type of abnormal cardiac condition. The reference data of the reference value module 552 can be threshold values, which can be based upon self- or population-norm data. The normative data can be obtained during one or more states such as rest, exercise, awake or sleep, and by classifying the patient state related to the current data 550, using the state module 568. The current data can then be compared to a reference data set obtained in a similar or different patient state, although normally this will be done using a similar state. In one embodiment, the normative data can include data obtained during one or more interventions such as during angioplasty where a balloon can be filled to create an acute ischemic event. This may be done in such a way as to mimic what might occur during a naturally occurring event. Further, the balloon can be filled (interspersed by sufficient recovery periods) to create different levels of ischemia in order to provide a scale of the changes in relation to amount of occlusion induced. An abnormal data template is created for an individual when the balloon is filled, in order to correctly estimate the changes that occur in that patients heart due to ischemia. A normal data template is created for the same individual when the passage is clear and adequate blood flow is occurring. The normal and abnormal data template can then be used in a number of manners, such as:

1. Feature selection: normal and abnormal templates can be used to select features that can be measured for that individual in order to best monitor cardiac status related to a selected symptom. Regression or other appropriate statistical analysis can be used to select, and subsequently evaluate the features that best discriminate between the two templates.
2. Scaling: normal and abnormal templates can be used to scale the selected features in order to understand how changes in these features relate to changes in the cardiac status that is related to a selected symptom.
3. Classification: normal and abnormal templates can be used by a classification algorithm, such as a discriminant/regression algorithm, in order to provide a probability that sensed activity is normal or abnormal. Abnormal events can be classified into one of several abnormal subtypes if more than 1 abnormal template is available.
4. Generation of guardbands: the variance of the data templates can be used to create statistical guardbands in order to provide statistical probabilities related to a detection of an abnormal cardiac event.

Although use of both normal and abnormal templates are preferable in some discrimination algorithms in order to increase specificity and sensitivity only the abnormal templates may be utilized to evaluate the sensed data. Further, collecting data during balloon catheter inflation was given as an example of an abnormal reference data set which would be clinically useful in subsequently detecting ischemic events, other manipulations that change the status of the cardiac activity in manners that are related to the symptoms of a disorder that will be monitored, are also possible. In either case, steps of methods used to obtain different types of baseline datasets can be accomplished semi-automatically by the cardiotrend system, or can rely primarily upon the expertise of a physician who can oversee the collection of reference data sets and then use these to program the cardiotrend system. The parameters can be selected by data analysis, using the modules of the implanted device, on a specialized computer or using modules in the external physician or patient programmer.

For example, during an angioplasty or stent implantation procedure the cardiotrend 500 can monitor ST segment change, identify the maximum change in average ST segment level at normal heart rate (STMAX-N), where an occlusion is used to create an ischemic event, and the statistical module 558 could set a patient threshold for excessive ST shift indicative of a heart attack to a value (e.g. 50% of STMAX-N) thus defining an abnormal template for assessing activity during a normal heart rate range. An alternate method of defining an abnormal template is to define a normal template by having the patient undergo a stress test following the angioplasty. The patient is first defined to be in a normal state, prior to the beginning of the test (ST-N). The maximum ST segment levels at an elevated heart rate can be measured (STMAX-EL) which define what is a normal elevation for the patient. The level of ST shift at elevated heart rate can then be submitted to the statistics module 558 to set a threshold value which defines excessive ST shift (e.g. 120% of STMAX-EL) thus defining a template based upon data obtained during normal cardiac activity. If the mean and standard deviation of the maximum ST segment levels at an elevated heart rate are measured (STMAX-EL), then this can be used to define what is a normal elevation for the patient, and can be utilized by the statistics module 558 to statistically provide guard bands for normal ST elevations (e.g., <2 standard deviations above mean value of STMAX-EL) which can be used to detecting ST deviations that occur during elevated heart rates. Further, both ST-N and STMAX-EL can be used to subsequently detect abnormal ST elevations. In one embodiment the difference between ST-N and STMAX-EL can be used to determine how far above STMAX-EL the average ST elevation must rise before it is evaluated as abnormal.

The present invention cardiotrend 500 provides improved methods of choosing appropriate normative data records and utilizing multivariate and/or classification schemes. In one embodiment, the method entails: computing a clinical state vector as a combination of two or more features related to the heart status of a patient, where each feature is associated with a particular weighting factor; computing a difference score, which may be represented as a vector, between the clinical state vector and a reference state vector; plotting this difference score as trend data, wherein if the magnitude of the vector increases over time then this indicates a worsening of cardiac status; and modifying CTOs according to evaluation of this trend data, for example, modifying CTOs when the trend, or slope of the trend, exceeds a threshold criterion. Further, in the present invention cardiotrend diagnostic module 516 of FIG. 3, the state module 568 may cause the multivariate analysis module 562 to utilize equations such that the clinical state vector is compared to a reference state vector that is selected according to the current patient stat index. Accordingly, instead of using a single disease state vector to detect or quantify cardiac abnormalities, two or more vectors and reference data vector sets can be used so that evaluation of sensed data are adjusted according to the patient state. This can provide great advantage because decreases in the sensitivity/specificity performance of the vector does not result due to an attempt to use a single formula to assess different abnormal event signatures which may be inherent within different patient states. Rather each disease state vectors can serve to assess abnormality within, rather than across, each of several different patient states. For example, cardiac disease state vectors that are specifically designed to detect abnormalities when the patient is awake, asleep, or engaged in exercise can be invoked based upon a detection of a patient state by the state module 568.

Moreover, in addition to assessing cardiac abnormalities solely by relying upon multivariate equations, the same features can be independently evaluated in a univariate fashion, so that if either the multivariate or univariate criterion is met, then a selected CTO can occur. The conditional module 566 can enable the univariate assessment of each variable which enters into the multivariate equation, and can be programmed to provide a CTO if either the univariate or multivariate criterion is met in relation to selected reference data. This is advantageous because when using multivariate equations, the ability of any variable to affect the multivariate composite index is, for example, 1/N, where N is the number of parameters evaluated by the equation (assuming equal weighting). Accordingly, when N is large, for example, over 5 or when a respective weighting factor is small (e.g., 0.1), then a large change in a particular measure may not influence the multivariate measure. By utilizing the conditional module 566 to detect cardiac abnormality if either a first or a second criterion is met (in this case a multivariate or a univariate criterion), a second type of detection can be provided, and may improve the clinical benefit of the cardiotrend device 500. Further, instead of using simple threshold criteria, the current invention uses the summary statistics module 558 in order to provide statistical assessment of the variability of the reference data, and to provide a statistical comparison between the current clinical state vector and a reference state vector in order to provide a statistical probably that a change in disease state has occurred. In the current invention, the clinical state vector and the reference state vector can each be computed based upon histogram data.

The conditional module 566 may not only be used to assess one or more operations using logical operators such as "and" or "<", but can also be used to set additional conditions upon abnormal event detection and alerting or other therapeutic operation. Further, in the case where events are not detected, but rather are classified, the module 566 can be set so that at the classification must suggest that there is at least a selected confidence level, for example, an 80% probability that the current activity is representative of an abnormal event in order for an alarm to be triggered.

The reference data module 552, can include statistical summaries of self- or population-normative data. These can be used to provide statistical probabilities that features of currently monitored data are either normal or abnormal result. These probabilities can be derived using both parametric and non-parametric algorithms, but parametric are preferable. The use of re-sampling analysis is especially well suited to the examination of histogram data, since it can use these empirical distributions, to provide bootstrap confidence intervals and other measures relating to the mean, variance, and skew of the distribution of the histogram data. The reference data of the reference value module 552, can hold data that is represented using a variety of forms such as histograms, meshgrids, tables of measures of features, statistical measures, scores and indices related to the data, and trends. The module 552 can also contain statistical summaries of these forms derived by the summary statistics module 558. Both reference and currently monitored data, can be represented with some redundancy, especially with relation to data being summarized across different time scales (e.g., week histogram data can summarize day histogram data that is concurrently being collected). In addition to storing reference data related to the monitored activity which may be stored in different normative data sets, the reference data module 552 can also store value used by the CardioTrend system such as criteria which are used to detect abnormal activity under different states, and data which are output from the various modules of the system. For example, the module 552 can store scores produced by the multivariate analysis module 562 so that a record of these scores is available for later analysis and downloading. Further, any information related to power consumption, error codes and errors which were reported by the control module 518 can be stored in the reference value module 552 as well as in the storage memory of the control module 518. In addition to sensed features and raw data, the monitoring results of diagnostic module 516 can also be stored. The reference data module 552, can also contain threshold and monitoring criteria. The reference data module can also hold summary statistics and measurements based upon raw features of the reference data and transformations such as spectral and histogram data, or trend data.

The diagnostic module 516 and its related methods provide monitoring results that can cause the cardiotrend system 500 to provide a number of CTO's. The monitoring results can be based upon the joint evaluation of 2 or more measures computed by modules embodied within the diagnostic module 516. In other words, rather than examining two or more measures independently, and comparing each of these to some selected criteria measures may be combined, for example, using the multivariate analysis module 562. Abnormal cardiac activity can be computed from the monitored signals that are being monitored. These can be related to temperature, electrical activity, a reflected optical signal, pressure or other measure and two or more measures, used to detect an anomalous cardiac event, can be obtained which are within or across these sensed signals. It is an important and novel feature of the cardiotrend system 500 that feature, trend and histogram data can all be used to increase the accuracy of the monitoring result provided by the diagnostic module 516. In other words trend data are not merely used for storage, but are also used to provide the monitoring result. This is a valuable feature since histogram data may have a number of characteristics that do not lend themselves to providing certain types of diagnostic information. For example, histogram data do not weight current data more heavily than temporally more remote data as long as these are both within the period covered by the histogram. Additionally, as the amount of data which is incorporated into the histogram increases, the effect each new data value on the histogram's distribution decreases.

The diagnostic module 516 and its related methods can also provide for a result which is based upon 2 or more measures by using the conditional evaluation module and methods 566. The conditional module 566 can impose logical operators (e.g., '>', "and") into the data evaluation processes. For example, if histogram data suggest an ST elevation increase of 10% has occurred, then this may only cause the monitoring result to trigger an alarm if, and only if, the feature analysis data indicate that the current heart rate is less than 90 beats-per-minute. The conditional module 56 allows multiple logical statements can be combined using various operators. The conditional algorithms can jointly evaluate past values, current, and predicted future values in order to determine if an alarm should be triggered.

The result module 576 of the diagnostic module 516 can trigger an alarm and also provide data which are used by the alarm module 522 to select the characteristics of the alarm signal. The monitoring results that are produced by the results module 576 allow the alarm module 522 to determine if an alarm is provided as well as which alarm of one or more choices. The monitoring results may be any of a number of outcomes such as detection of an normal/abnormal cardiac condition or event, classification of current and/or recent data into one or more abnormal categories, or simply the detection or quantification of an abnormal feature (which exceeds some threshold) that is relevant to the cardiac disorder being monitored. The diagnostic module 516 and methods, working in conjunction with the other modules of the system 500 can determine if, which, and when to provide one or more types of CTOs such as an alarm warning, intervention, and/or storage of data.

The histogram analysis module and methods 556 can provide quantification, evaluation, and classification of histogram data, in order to detect and assess cardiac abnormalities. The summary statistics module 558 can provide summary statistics of the histogram data to the comparison module 564 in order to assist in comparison operations carried out between current histogram data and reference histogram data. Analysis of histogram data can include a number of measures such as peak-bin, variance, skewness, or average, and can include algorithms to perform such methods as regression, smoothing, interpolation, and calculation of slope. The bins of the various histograms can be of identical width or can be variable, and can be adaptively defined in relation to a patient's specific disorder based upon, for example, the physician's evaluation of self-norm data. A number of studies related to image compression and evaluation have shown that clustering strategies, adaptive binning and dissimilarity indices produce the best overall performance (in terms of yielding good accuracy, a small number of bins, reduced empty bins, and efficient computation) compared to various types of fixed-bin strategies. Efficient dissimilarity measures have been developed for comparing histograms with different binnings in order to detect shifts or differences. Applying these measures to the heart histogram data might occur when a physician determines that a characteristic of the heart activity will assume some average range, when the patient is in a normal state, and will jump to a specific higher range when it has a type of relevant abnormality. In this case, the bins near the peak bin of the histogram can have wider widths as these define normal activity, and the bins near the positive tail of the distribution can have more narrow widths so that smaller changes in distribution or occurrence can be detected with greater precision. In the range which is determined to be above the average normal activity and below the minimum of the abnormal activity range, there may be no bins since this type of information is not relevant to detecting the selected abnormality of this patient according to the self-normative data.

The histogram module 556, of the diagnostic module 516, can operate the histogram module 654 of the storage module and can control the histogram storage methods 657 in order to store and analyze histogram data according to the control program 519. The histogram module 556 can operate these modules to carry out analysis technique specifically related to histogram data, such as measuring skewness, the contour of the histogram, or slope of the contour; transforming histogram data via log or other transformation of an axis; interpolation across bins; smoothing; determining a threshold based upon the histogram distribution; distribution analysis methods for determining if a histogram is modal or bimodal; bihistogram analysis; tests of distribution and shift in distribution (e.g., Kolmngorov-Smirnov tests); quantile and percentage analysis; t-tests for shifts in location; F-tests for shifts in variation between a single bin at 2 different times, or to compare a bin to its neighbors; weighted or filtered histogram analysis; routines for adding, subtracting and finding differences and statistical differences between histograms or portions of histograms; algorithms for assessing cumulative frequency and probability density functions; and historical histogram analysis whereby a set of histograms can be aligned in waterfall plot and changes in the distribution, including temporal patterns of change, can be evaluated automatically (using a spatial pattern matching algorithm on the waterfall-plot or 'mesh-grid') as may assist in detecting or assigning scores to patterns that precede, reflect, or predict certain types of abnormal cardiac activity. The histogram analysis/storage strategies are also oriented towards detecting relative differences between different sensors, in order to detect local changes, as well as combining data across sensors to provide increased detection of a global event.

By comparing, or otherwise analyzing, histograms from different sensors, and comparing these data sets, for example, by computing difference between the same component at different electrodes, the cardiotrend system can detect and localize an abnormality. For example, the abnormality can be localized to a particular blood vessel, if the histogram data from the data sensed from that vessel (or the electrophysiological/optical signature related to that vessel) differs from data collected at other vessels, as long as this difference meets a monitoring criterion. This type of detection is especially useful when optical data are obtained and evaluated with respect to SA02 levels which exist in different vessels (and which may be sensed by extra-cardiac optrode sensors) which supply the cardiac tissue of the patient.

The different modules of the diagnostic module 516, including the feature, histogram, summary statistics, state and trend analysis modules and methods can be used in the detection and classification of abnormal cardiac events and conditions, and in the comparison between current data to a least a portion of the reference data. The diagnostic module 516 can work with the other modules of the system 500 to provide cardiotrend operations (alert warnings, detection of cardiac abnormalities, and treatment) to occur in a more sensible manner than that currently available. For example, rather than simply comparing sensed activity to a threshold, the system 500 can operate to provide therapeutic benefit based upon a more thorough picture of the patient. By way of illustration, the system can operate so that in addition to a treatment threshold being exceeded, an alert will not be sent unless the following are also true: the patient has been awake for at least one hour (state module 568); the patient has not exercised within the last 30 minutes (state module 568); an alert warning has not already been sent in the last 10 minutes (alarm module 522); heart-rate has been below a specified range for at least 30 minutes (trend analysis module 560); and, the threshold has been exceeded for at least 2 minutes (conditional module 566). In summary, the provision of therapeutic operations of the system 500, and other cardiac event responses such as patient alerting, can be adjusted according to at least one of the history of patient state values, the history of evaluated sensed data, and the history of operations of the device itself (such as the provision of recent alerts). The improved treatment benefit realized by the methods and systems described here can be applied to therapy directed towards treatment accomplished with other types of implanted devices such as neurostimulators, vagal/cranial nerve stimulators, and drug pumps.

The Alarm Module.

Figure 4:
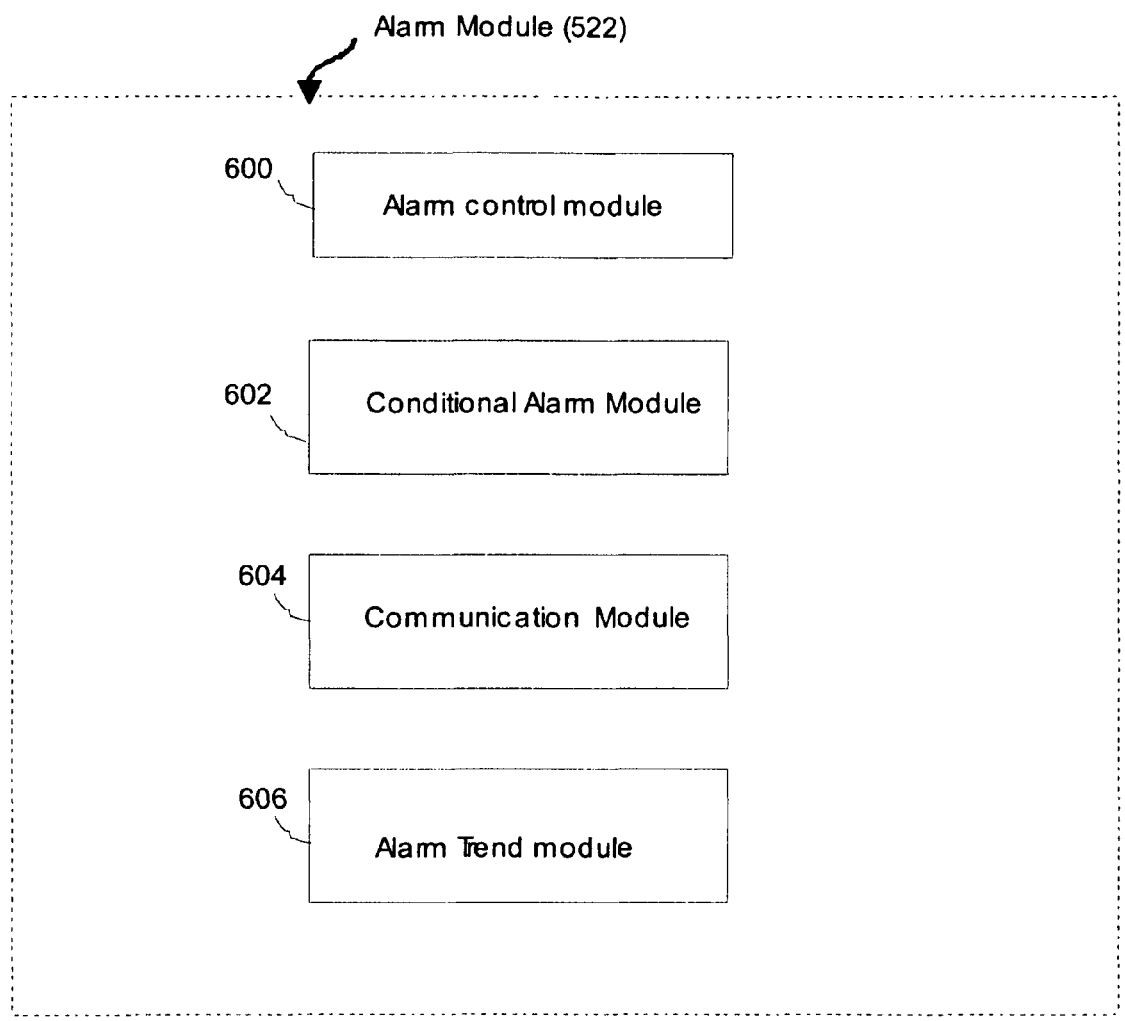
FIG. 4 shows a preferred embodiment of the alarm module.

The methods and components of the alarm module 522 shown in FIG. 4, which provide alarms when the control module 518 of FIG. 1B triggers an alarm, can be referred to under the term "EKGsaver". The alarm can be triggered by the control module 518 in response to monitoring results provided to it by the diagnostic module 516, in response to a control signal which is generated according to control laws 572, or in response to a treatment protocol implemented by in a control program 519 which dictates that alarms should be provided at certain times. Alarms can also be provided after certain durations, if selected events are, or are not (e.g., lack of cardiac response in an interval after taking medication), detected. The alarm control module 600 controls the alarm operations according to an alarm protocol in order to determine if, when, and what alert signals are provided by the system 500. A conditional alarm module 602 contains alarm criteria which must be met in order for an alarm to be triggered. The conditional alarm module 602 and associated methods provide one or more types of alarm warnings (and may also induce changes in the intervention and/or data storage protocols) based upon conditional meta-criteria which are applied to the results derived by the diagnostic module 516. In one example, if the diagnostic module 516 provides a result which indicates that a decrease in QRS amplitude of 8% has occurred, conditional criteria of the conditional alarm module 602 can dictate that this may have to occur for 3 days before a CTO (i.e. in this case an alarm) is triggered, while a decrease of 12% must only last 2 days, and a decrease of 15% or more leads to an immediate CTO. Alternatively, the conditional module 566 of the diagnostic module 516 may use the same conditional criteria prior to allowing the result module 576 of the diagnostic module 516 to produce a certain result, (e.g., a "yes" result), which would cause the control module 518 to perform a CTO such as sending a command to the alarm module 522 to trigger an alarm (or triggering an intervention, or responsive data storage, to occur). The conditional alarm module 602 and the conditional module 566 of the diagnostic module can therefore be used to accomplish the same results. In general, the prior module places conditions on alarms being produced while the latter places conditions on the generation of monitoring results and on the events being considered as abnormal events which are able to trigger alarms. The conditional alarm module 602 is different than the conditional module 566 of the diagnostic module 516 in that the module 602 can be used to place restrictions on the production of alarms such as, if an alarm has been triggered and shut off by the user, do not trigger another alarm until at least 5 minutes have passed, even if additional abnormal events are detected, unless these additional events are of a much increased severity. This type of restriction is important so that the user isn't startled by repeated alarms which are functionally serving to alert the user to a condition which is already known by the user to last several minutes or so. The alarm communication module 604 triggers either internal or external alarms and contains protocols for providing alarms to different implanted or external transducers such as speakers, an ONSTAR-like system, or the external patient programmer. The alarm trend module 606 is a meta-analysis module which keeps track of the history of alarms including the types, frequency of occurrence, and duration of alarms. The alarm trend module 606 can provide different alarms due to trends in the alarm activity. For example, if the number of a certain type of alarm has increased from 4 to 10 alarms per week over a 1 month period, the alarm trend module 606 protocol may cause the alarm module 522 to send an alarm to the central station 505 of FIG. 1A or may provide a visual message to the patient "see doctor soon". The alarm module may also generate an array of alarm events similar to the patient state array, so that a meta-analysis of alarm data can be accomplished.

The Storage Module.

Figure 5A:
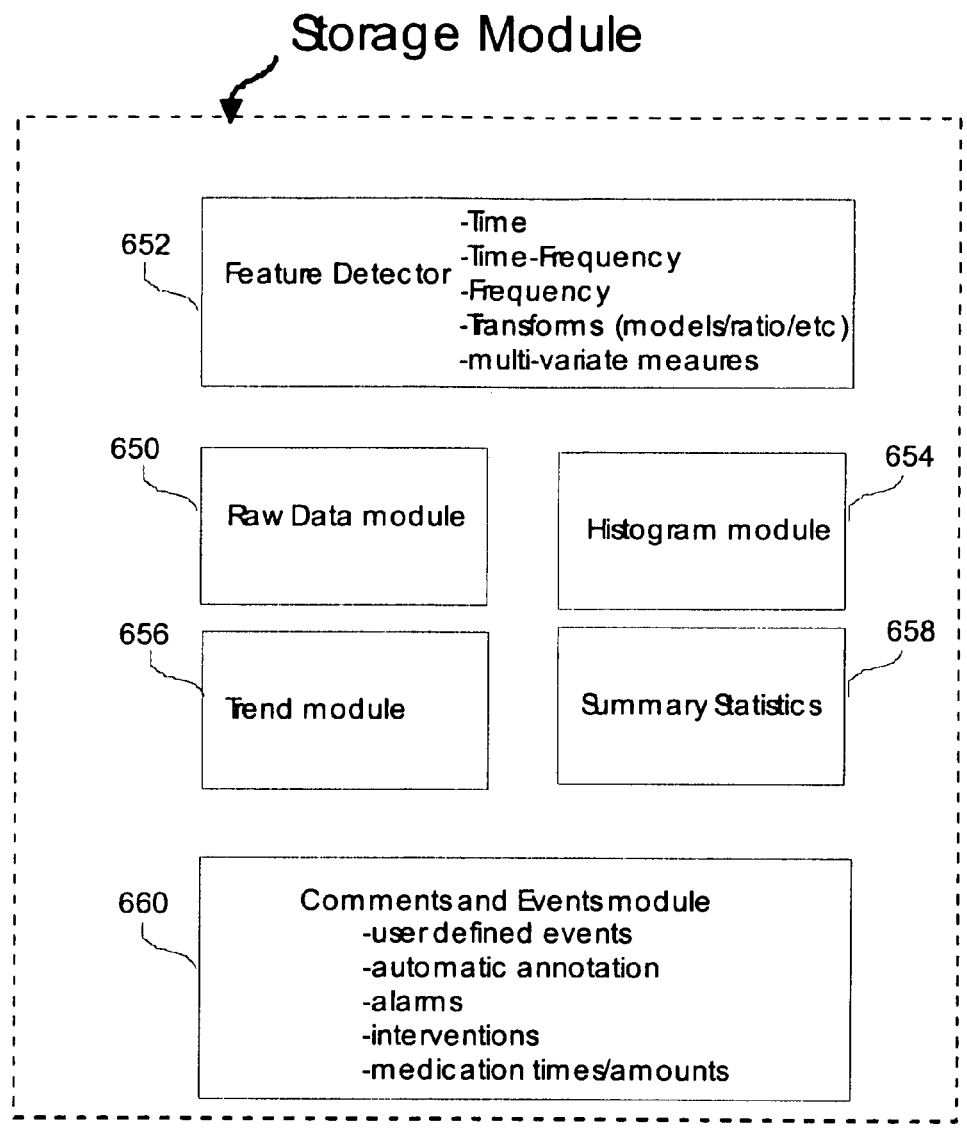
FIG. 5A shows a preferred embodiment of the storage module.

FIG. 5A illustrates the storage module 526. The methods and components of the storage module can be referred to under the term "QRSTracker". The control program 519 of FIG. 1B can cause the control module 518 to store data, using a data storage protocol, by controlling the operation of the modules of the storage module 526. The raw data module 650 stores of raw segments of monitored data.

The feature module 652 stores measurements of features of the sensed data, including both measurement of intra-beat and inter-beat features, such as amplitudes, widths, slopes, curvature, ratios, and times related to components of the beats of the cardiac waveform. The feature module 652 can also store statistical values related to features measurements based in the time, time-frequency, and frequency domains. The feature module 652 can also calculate, store, and access values and statistics related to transforms of the data (e.g., results of principal component analysis such as factor scores), indices which reflect a relation between two measures (e.g., ratios of Q-R/R-S amplitudes) or between two sensors (e.g., a correlation between data sensed from different sensors). The storage module's feature detector 652 can also store a history of multivariate measures (e.g., outputs of regression or discriminant formulas).

The histogram module 654 can create histograms based upon the values derived in the feature 652, trend 656, or summary statistics 658 modules. The histogram module 654 can also create histograms based upon the values in the histogram module 654. For example, the histogram data for days of the week can be used to create a histogram which represents data for weeks of the month.

The trend module 656 can create trends based upon the values in the feature 652, histogram 654, or summary statistics 658 modules. The trend module 656 can also create trends based upon the values in the trends module 656, for example, the trend data for each of the days of the week can be combined into a single trend array which holds, for example, the slopes of the trends for each day of the week, for the weeks of the month.

Likewise, the summary statistics module 658 can compute summary statistics upon data held within the other modules of the storage module, or upon subsets of statistical data also contained in the summary statistics module 658. The summary statistics module 658 can combine or redistribute data to produce new statistical measures reflective of different spans of time.

The comments and events module 660 can store comments entered by the physician or patient, which can be time-stamped, and which can have written or verbal formats (as recorded by a microphone of the EXD 502A). The comments and events module may be realized jointly or wholly within external components such as the EXD 502A. The comments and events module 660 can store a log of information related to alarms, or information created by automatic annotations and summaries resulting from automatic or user requested analysis of the data. Additionally, the comments and events module 660 can record times and durations of interventions such as pacing or defibrillation, the taking of medication by the patient, and can store other information such as error codes or data which relate to internal operations of the cardiotrend system 500, such as those which can be generated by the control program 519 of the control module 518. Information related to pacing or defibrillation stimulation, which is provided by implanted devices which do not directly communicate with the CardioTrend system, can be obtained by the feature module, which can identify features in the sensed data that are indicative of the presence of pacing or defibrillation by a separate device. Since electrical stimulation signals are synthetic, these are normally very easily detected in the monitored data. In one embodiment, the storage module can keep a historical record of all or many Cardiotrend events and operations, including time-stamping or other index reflecting the durations or number of occurrences of different events. When this historical record spans, for example, between 1 and 10 hours then, similar to the patient state array, it can be used in order to constrain current operations based upon historical activity of the patient and the device.

Figure 5B:
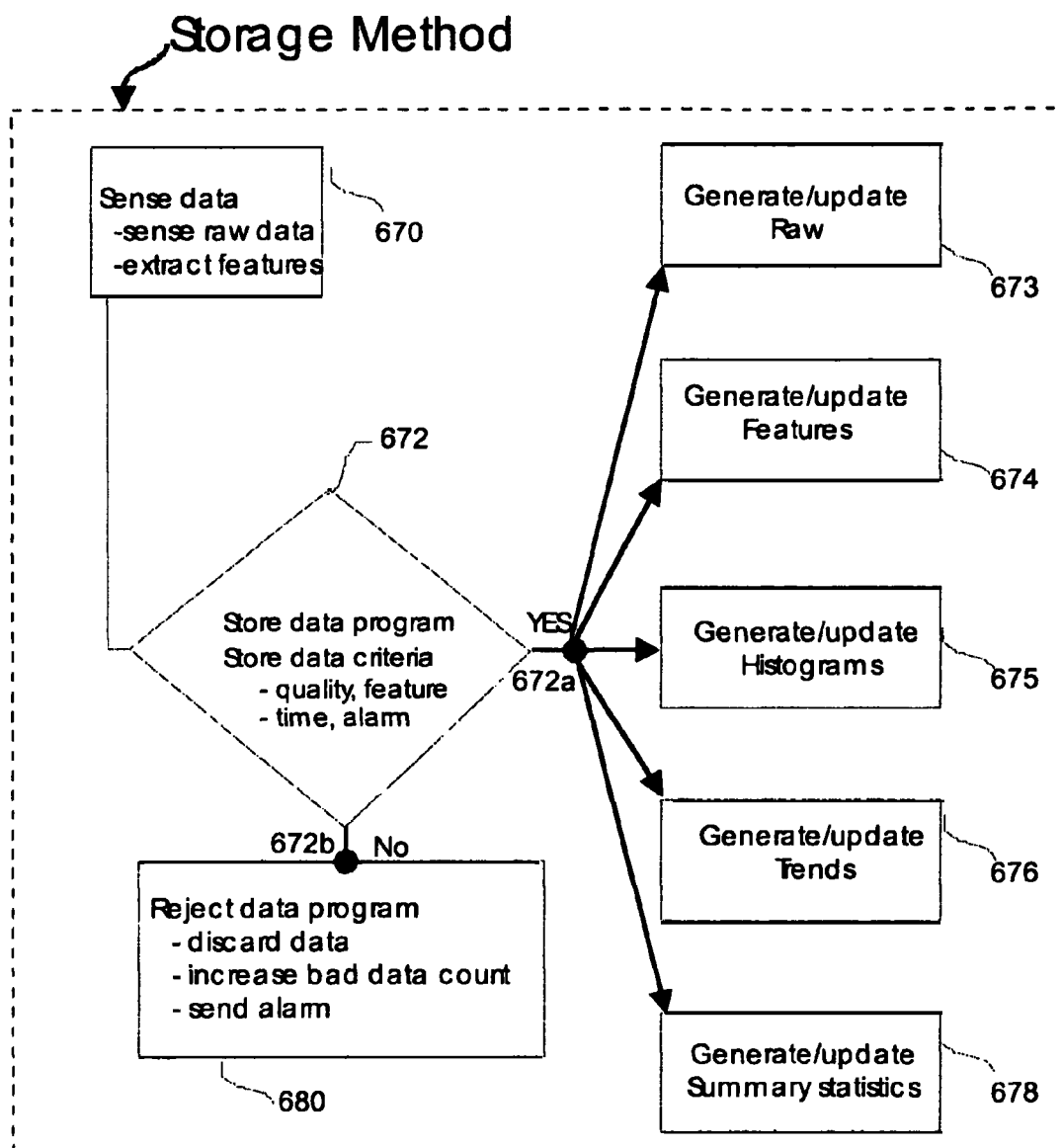
FIG. 5B shows a schematic representation of a method of operating the storage module.

FIG. 5B illustrates an embodiment of a storage method for storing both raw and processed measures of sensed data in the storage module 526. In step 670 monitored data are sensed and selected features are extracted. In step 672, a store data program is run which, based upon one or more "store data criteria", results in either a "yes" or "no" result, 672a and 672b, which cause data storage or data rejection, respectively. For example, a 'quality criteria' can be used where data must have at least a specified signal-to-noise ratio, or be free of selected cardiac features, in order to be stored. A 'feature criteria' can be used where data must manifest a feature, such as a heart rate within a specified range, in order to be stored. A 'time criteria' can be used, for example, in which data are only stored if the time criteria indicate that some amount of time has passed since the last data were stored. An 'alarm criteria' can be used where data are not stored unless an alarm has been recently triggered. In one embodiment, data can be stored continuously in a temporary circular buffer. When an alarm is triggered, a specified section such as only the prior 5 minutes are stored, and the remaining prior-alarm data are cleared from the circular buffer.

Other store data criteria can be utilized as well. If the store data program 672 determines that data should be stored 672a then this may cause an update to occur in the raw, feature, histogram, trend, or summary statistics data storage 673, 674, 675, 676, and 678, respectively. In addition to sensed features and raw data, the monitoring results of diagnostic module 516, or any value computed by modules in the diagnostic module, such as values output from the state module, or multivariate scores output from the multivariate analysis module 562 can also be stored in additional modules and according to a number of different storage subroutines (although these not shown in figure to reduce cluttering of the figure). When the store data program 672 determines that data should not be stored 672b then step 680 occurs in which the 'reject data program' determines what to do with the rejected data. The reject data program 680 may simply discard the rejected data. It may also send an alarm that data are being rejected if, for instance, the reason is that rejection occurred due to bad signal-to-noise quality. It may also send an alarm after increasing the count or tally of bad data which occurred over the last 2 hours, for example, if the count is above a specified value for a given duration. The alarm may notify the patient or central station of "bad data quality" and the user or a physician may then perform a calibration or other diagnostic test to ensure that the cardiotrend system 500 is operating correctly.

Figure 5C:
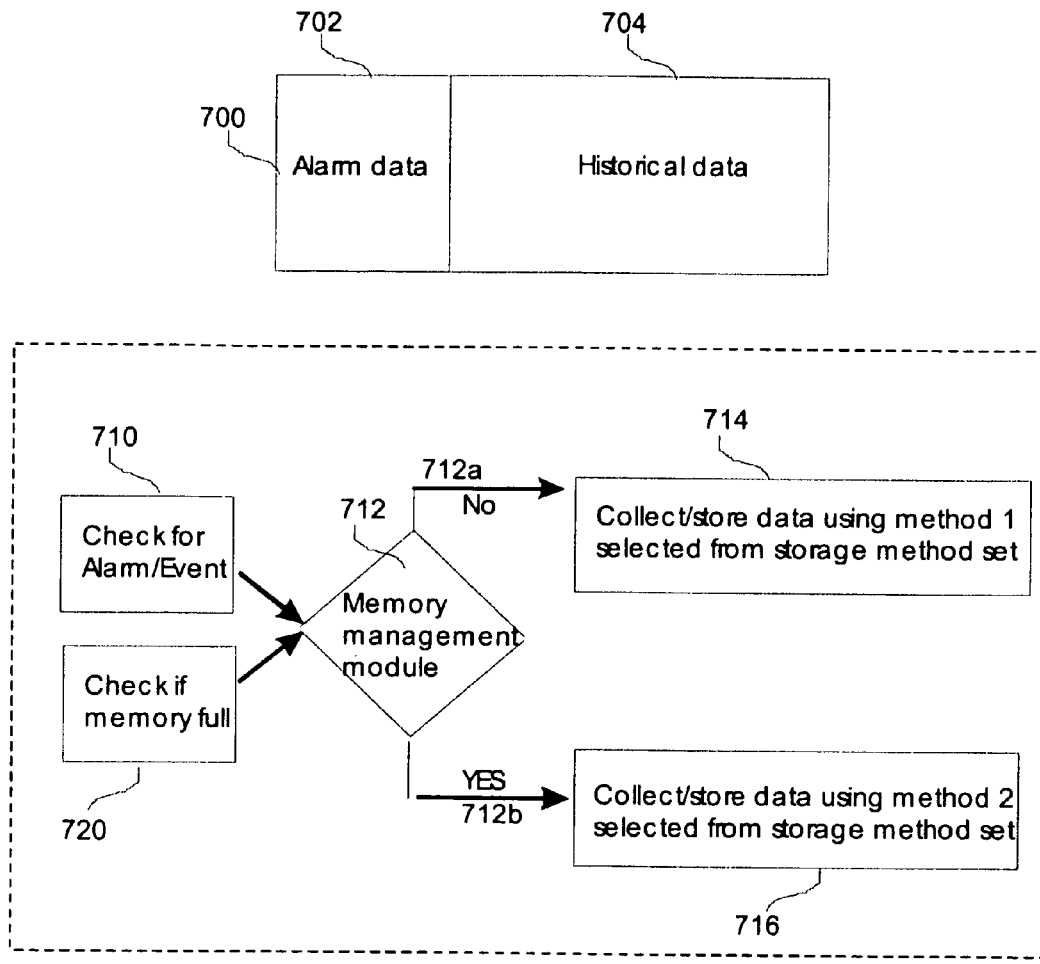
FIG. 5C shows, on the top, an embodiment of a data module including divisions for alarm and storage data, and shows, on the bottom, a method for using such a data module.

FIG. 5C, top, illustrates an embodiment of a data structure for storing data in 2 (or more) different formats. The data can be stored in data memory 700 which is divided into an alarm data memory 702 section, and a historical data memory 704 section. The cardiotrend system 500 provides methods of efficiently storing data wherein much of the data can be represented as histogram data, summary data, and trend data. However, while histogram data may be efficient for summarizing cardiac activity over long segments of time, abnormal cardiac activity can be more accurately detected by storing more recent data in a more detailed manner that allows for more extensive analysis of the monitored signal, and older data in a less detailed manner. In one embodiment, historical data can contain only 1 or 2 channels of data while alarm data can contain a greater number of channels, e.g. 3-6 channels. By dividing data storage into two or more sections, where at least one section provides a more detailed record for more recent data, the cardiotrend system 500 can both accurately detect cardiac abnormalities and also can efficiently store historical data records. The method of data storage, within each section, can be adjusted due to an event or alarm warning, where after the detected event the data are stored in a different manner than prior to the event.

'Memory events' are events which alter the memory storage protocol enacted by the control memory storage program that is implemented by the storage module 526. The control memory storage program, like the control alarm program and control intervention program, can be implemented as a subroutine of the control program 519 of the control module 518. In this embodiment, the memory, intervention, and alarm CTO's occur as defined within the control program 519. In one embodiment, when a memory event such as an alarm occurs the historical data, which normally contains only 1 or 2 channels of data, will subsequently contain a greater number of channels, e.g. 4-6 channels, for a specified post-event period in order to provide more detailed information during that period.

It is an object of the invention to create an alarm dataset which is stored in the alarm data memory 702 which is used for monitoring cardiac status, and a storage dataset stored in a historical data memory section 704 which can be used for both monitoring cardiac status and for efficiently providing storage of monitored data. The manner in which data are stored (e.g., in histogram or average spectral format) in the historical data memory section 704 may be good for providing efficient storage, but may not be optimal for detecting relevant cardiac events. For example, histogram data may not be very sensitive in detecting rapid or acute cardiac changes because old and new values of the histogram are weighted similarly. Additionally, after histogram data or features have been derived from the sensed data, the raw data may be decimated prior to storage of the raw waveforms, since greater resolution may only be needed for deriving certain features from the data. Even decimation by a factor of 2 can substantially decrease the memory needed for storage of the raw data.

On the bottom half of FIG. 5C, an additional method of storing data is shown, whereby data are stored according to a first method 714, which may be selected from a storage method set, prior to the triggering of an alarm or event, and is stored according to a second method 716 which can be selected from the storage method set after the alarm or event is triggered. For example, prior to an alarm, histogram or raw data from only 1 or 2 channels of data are stored, whereas after an alarm, when more information may assist medical personnel in the diagnosis of the cardiac abnormality, 3 or 4 channels of data can be stored. It is also envisioned that the frequency of storing the data could change after an alarm or event. For example, the cardiotrend 500 might save 30 seconds of electrogram data once per hour if abnormal activity has not been detected and change to saving 30 seconds of data every 5 minutes if an event is detected.

In addition, the step 712 can lead to more than results 712a or 712b. The storage method selected may be based upon the type of alarm or event that is detected (which can be more than two types of events although only 2 types of events 710 and 720 are shown in the figure). The method can address the problem of what occurs if the data memory becomes full, as indicated by event 720 being evaluated as true 712b by operation of memory management module 712. For example, if there is enough memory for 7 days of data storage, but the patient does not return to their doctor or does not download information into the external patient programmer, should the cardiotrend system 500 simply stop recording new data, overwrite a portion of the current data to continue to store new data, or perform another type of storage method? By selecting a memory full method, method 2 of the storage method set 716, when the memory is found to be full 720, or almost full, this issue can be addressed. In addition to providing an alarm that the memory is full, the device can continue to choose different memory full storage methods as more time passes from the time that the memory first filled up. If the memory full status is indicated by the module and methods of step 720 then method 2 can be selected from the memory storage set. Memory full storage methods selected by the memory management module 712 can include steps which implement, for example, at least one of the following strategies: Get more data and over-write previous data, in a specified order that may include overwriting the oldest data and then the newest data; Stop collecting new data and wait; Monitor sensed data and only over-write older data with new data if an alarm has been triggered; and, Alert the patient to see their doctor to offload the stored data making room for new data.

The cardiotrend system 500 can index, segregate, and subsequently analyze the stored segregated data, constructed based upon segregation schemes related to, for example, time or patient state (such as awake and asleep). The memory management module 712 can communicate with the diagnostic module 512 in order to classify or index data and determine how these are stored. This allows patient-state-appropriate reference data sets to be accessed. For example, if a patient awakens, the data monitored during the first hour after this change of state, can be compared to stored activity (i.e. a self-norm) which was collected prior to the patient going to bed, or during the same time period on the previous day, rather than using a self-norm computed upon a duration of data sensed in the period prior to the patient awakening. In another example, if the patient is exercising, then the self-norm data to which this current monitored data are compared is based upon a previous patient-state during which the patient was exercising. This data may be more appropriate than using a self-norm computed upon stored data that was related to a period prior to the initiation of exercise when the patient was at rest. The selection of self-norms, to which current data are compared, can be made according to a wide number of possibilities, so that these provide reference data for a similar time or patient state, and increase therapeutic benefit of the monitoring and patient alerting. However, state-appropriate comparisons are only possible when the stored data have been archived in a segregated manner, or has been stored in conjunction with indices which allow for dynamic segregation of stored data according to the monitoring scheme. The CardioTrend system and methods as described herein allow these advantages to be realized, and also allow for multiple data storage formats which are chosen dynamically in various beneficial manners, some of which will now be further described The present invention cardiotrend system 500 can introduce data collection and storage strategies which dynamically change with the amount of archival data which is stored. In prior art techniques, data are often summarized or compressed in a signal manner, and the objective is to be efficient and store as much data as is possible. However, although it may be beneficial to compress a data set efficiently in order to increase the amount of data which is stored, early in the storage process (e.g., at the beginning of a 6 month monitoring period), the memory sections which will be filled up later are not accessed or utilized. In one alternative memory storage scheme, data are stored in a first manner until a portion of the data memory (e.g., ½) is filled up, and then data are stored according to a different strategy. The step of changing the memory storage algorithm can obviously occur several times as the memory data structure is filled further. This strategy can permit, for example, an intensive data collection storage mode in which all memory is utilized by two or more types of memory where one type of memory is the final archived data, and memory is re-allocated as needed, as the size of the final archived data grows towards its final size. In one embodiment, there can be a "core" data set which is always stored and which comprises pre-selected feature, histogram, trend, and summary statistic data, and also a "dynamic" data set, which is dynamically defined, for example, by the types of alarms which are triggered. An "alarm" data set, may also be used, which holds current data related to an alarm and which may be used, by the diagnostic module 512 in conjunction with the core and dynamic data sets in order to generate further alarm warnings.

The methods of the memory management module 712 can also be used to predict, based upon current and past patterns of memory storage, how much more time is available with current memory capacity. For example, if a certain amount of raw data are stored every time there is an alarm, and 1 or 2 alarms have occurred, on average, every week, then the residual memory would be sufficient for a certain amount of time, which would be less than if 4 or 5 alarms occurred each week. The memory management module can make these calculations based upon historical activity and can alarm the patient when memory is predicted to become filled in the near future. Alternatively, the memory management module 712 can provide the storage module 526 with an alarm-based memory strategy, where the format of the data which are stored is altered based upon the type of alarm that is triggered by the data. After an alarm is triggered, a selected amount of raw data or more detailed summary data can be collected in order to provide more information. This permits more data to be collected when this is more important. Similar to an alarm trigger, when the patient utilizes the EXD 502A or DTD 502B of FIG. 1B to indicate that an event has occurred, the format of the data which are stored can be altered based upon the event type that is indicated by a patient. Different events can be selected based upon a button press of two or more buttons provided in the input modules 503 of the cardiotrend system 500.

Figure 6:
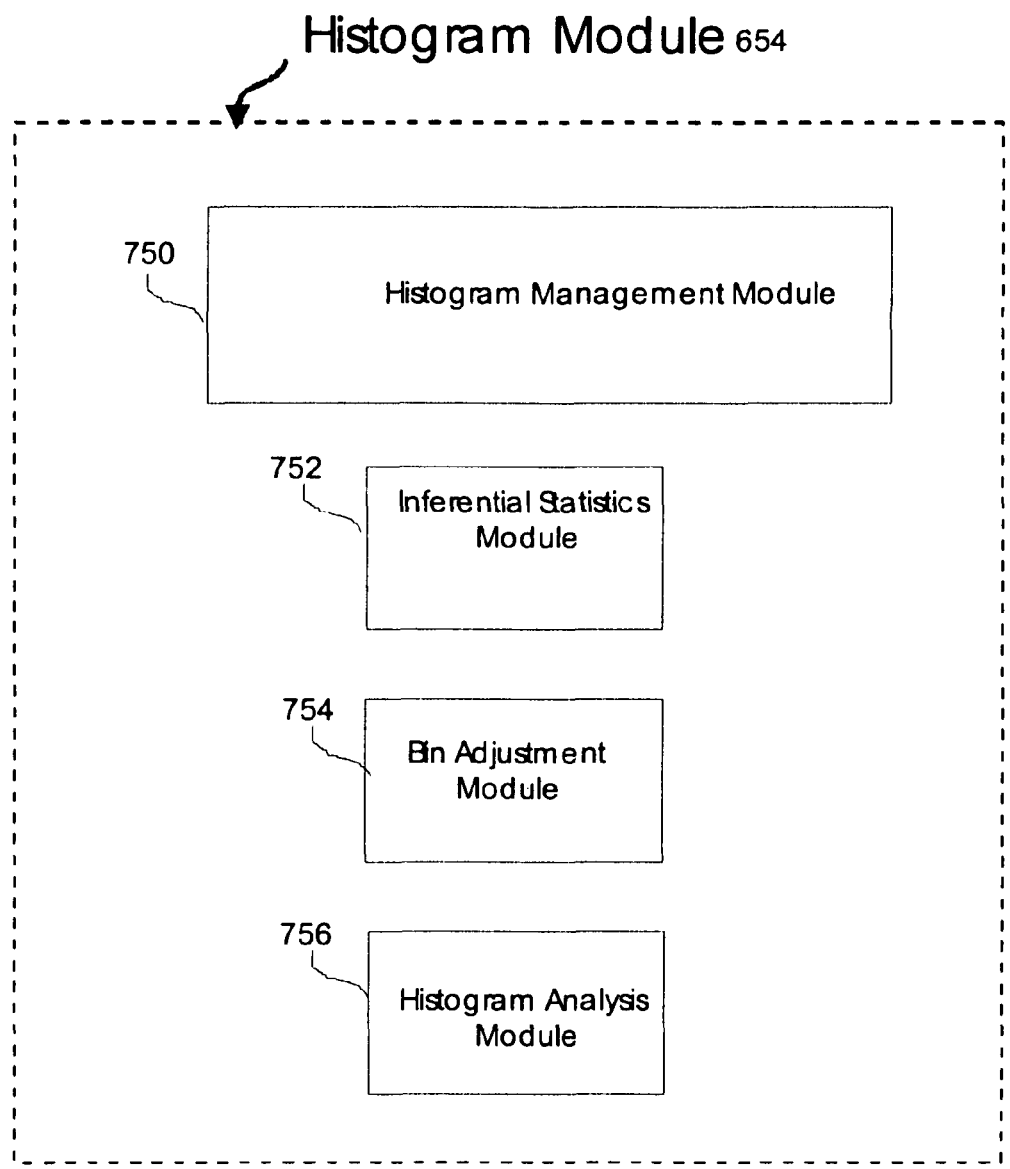
FIG. 6 shows a preferred embodiment of the histogram module.

The storage module 526 of FIG. 5A may include a histogram module 654 which manages the storage of monitored data into histograms, as well as providing subsequent analysis of these histograms. FIG. 6 shows a preferred embodiment of the histogram module 654. The histogram module 654 contains a histogram management module 750, which performs management of the histogram data including storage of different types of data into different histograms. Histogram data can comprise histograms segregated based upon, for example, different states of the patient, across different durations, different measurements related to a feature, such as peak-amplitude and slope, or different sensors at which activity was sensed. The '705 application of Fischell demonstrates a number of advantageous schemes for histogram (and trend graph) segregation such as generating histograms of various features of the cardiac activity according to different rates of heart-beats. For example, QRS voltage deviations, expressed as a percentage of a baseline self-norm reference, are grouped for 3 heart-rate ranges of 50-80, 81-100, and 101-120.

The histogram storage module 654 provides a number of features that are believed to be improvements over prior art. Firstly, rather than, or in addition to segregating data based upon absolute ranges for heartbeat or other measure, ranges can be defined based upon percentages. For example, ranges can be from 1-20% or 20-40% above the mean heart rate. Using percentages, rather than absolute values for the ranges help to normalize monitored data in relation to the patient, and can be less immune to ceiling or floor effects due to individual differences. In addition to relying upon traditional statistical estimations of the data, the histogram module 654 can have a statistics module 752 which contains re-sampling routines for estimating inferential statistics such as bootstrap confidence limits of a particular measure, as well as also containing both parametric and non-parametric statistical testing algorithms. Bootstrap statistics utilize re-sampling methods which are especially well designed to evaluate histogram data. Bootstrap statistics can be computed by re-sampling the data and creating histograms in order to infer the probable distribution of a measure from a sample. The present invention cardiotrend 500 can provide confidence limits based upon a portion of the trend data, and an alarm can be triggered if the trend surpasses these limits. The confidence limits of the trend data can be calculated in a number of manners such as computing the resampled confidence limits or by using simple standard deviations of the data which were used to generate the one or more data trends. Further, the bins of the histogram may have different widths and may be separated by different intervals.

A bin adjustment module 754 can set or adjust the center value, width, and number of bins of the histograms in order to be efficient in both the detection and storage of the data. Accordingly, it is an object of the invention to adaptively select the center value and width of the histogram bins based upon self- or population-norm data with respect to the measure being evaluated The present invention provides for the adaptive setting of the number of bins and bin characteristics based upon selected samples of a patient's data, subsequent evaluation and storage of that data in histogram format.

The Intervention Module

Figure 7:
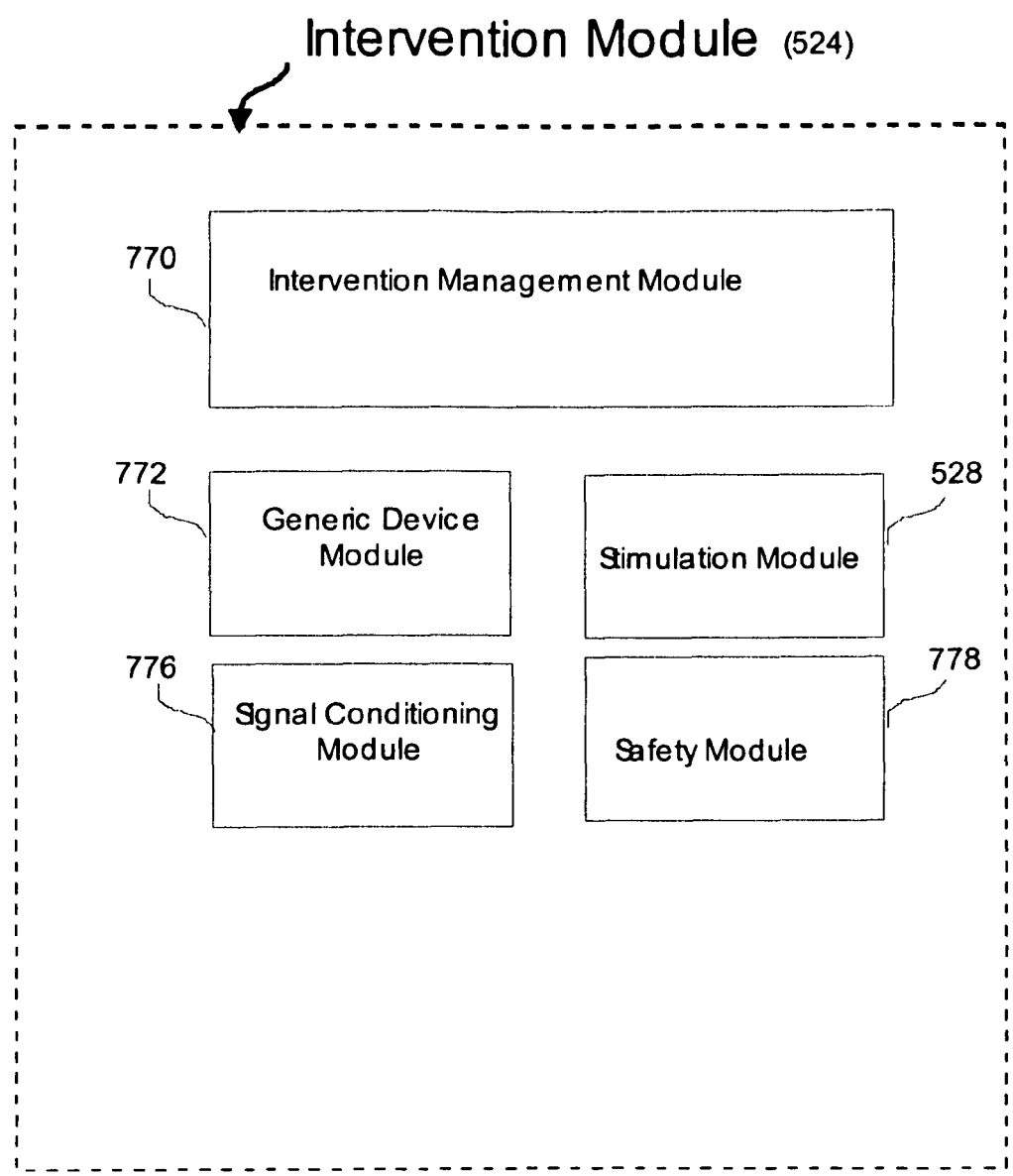
FIG. 7 shows a preferred embodiment of the intervention module.

FIG. 7 illustrates the intervention module 524 which can be used to provide electrical or other types of intervention such as pacing or defibrillation. The intervention module can use the stimulation module 528 to send stimulation signals to the signal routing module 530 which then relay's this signal to a designated stimulation means. Alternatively, the intervention module 524 can use the stimulation module 528 to send stimulation commands to implanted generic devices using the communication module 521 which can communicate with other implanted or external devices via wireless telemetry or a physical wired connection between the cardiotrend 500. The methods and components of the intervention module can be referred to under the term "IMS-Guard". For example, the IMS-guard can communicate with an external automated defibrillator to initiate a defibrillation pulse or an implanted pacemaker to begin cardiac pacing. The intervention module 524 may include an intervention management module 770 which contains intervention instructions, programs and associated parameters related to providing one or more types of intervention. This includes stimulation protocols and their respective parameters. The intervention module 524 can utilize a generic device module 772 for storing information related to identifying and controlling generic implanted devices, including electrical and drug delivery devices, including commands that can be sent by the communication module 521 in order to cause a particular intervention. For example, the generic device module 772 could enable the system 500 to cause a pacing program to be initiated by an implanted generic pacemaker made by a separate company. When the system 500 contains its own stimulation components, the stimulation module 528 can provide therapeutic stimulation signals, such as pacing signals to the signal router and can send commands to the signal router module 530 so that the stimulation signals are routed to their intended stimulation conduits. The stimulation module 528 can provide signal conditioning including filtering, D/A transduction, and amplification with its signal conditioning module 776 when the signal conditioning module 512 of the sensing module 510 is not relied upon, as may occur when sensing is to occur approximately concurrent with stimulation. The intervention module can also contain a safety module 778, which contains routines that ensure that intervention does not occur which exceeds a specified amount, such as providing too much drug or electrical stimulation within a specified amount of time. Further, the size of the stimulation or other stimulation settings can be limited for all patients, or can be adjusted for a particular patient by adjusting the parameters of the safety program of the safety module 778.

Heart Signal Features

Figure 10:
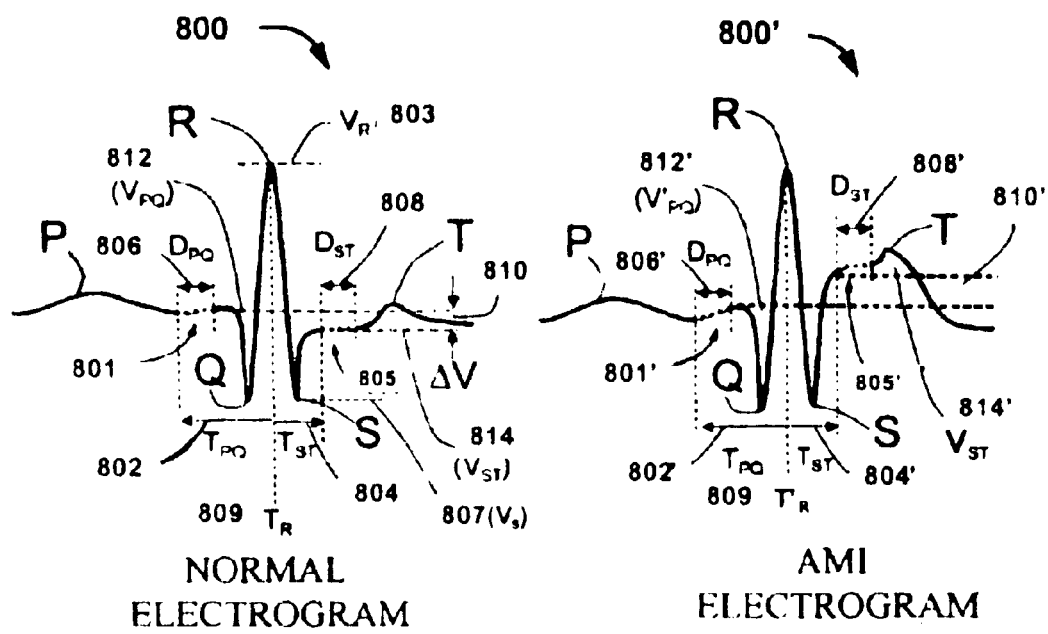
FIG. 10 illustrates an electrogram segment and associated heart signal features.

To provide context for the specific Cardiotrend embodiments discussed below, which involve the acquisition and analysis of cardiac electrical/magnetic activity, certain characteristics of the electrical/magnetic activity will now be described. In particular, FIG. 10 shows electrograms associated with heart beats 800 and 800' and various heart signal features. The peak of the R wave of the beat 800 occurs at the time $T_R$ (809). The PQ segment 801 and ST segment 805 (is this correct?) are sub-segments of the normal beat 800 and are located in time with respect to the time $T_R$ (809) as follows:

a. The PQ segment 801 has a time span $D_{PQ}$ (806) and starts $T_{PQ}$ (802) milliseconds before the time $T_R$ (809).
  b. The ST segment 805 has a time span $D_{ST}$ (808) and starts $T_{ST}$ 804) milliseconds after the time $T_R$ (809).

The PQ segment 801' and ST segment 805' are sub-segments of the abnormal beat 800' and are located in time with respect to the time $T'_R$ (809') as follows:

c. The PQ segment 801' has a time span $D_{PQ}$ (806') and starts $T_{PQ}$ (802') milliseconds before the time $T'_R$ (809').
  d. The ST segment 805' has a time span $D_{ST}$ (808') and starts $T_{ST}$ (802') milliseconds after the time $T'_R$ (809').

The ST segments 805 and 805' and the PQ segments 801 and 801' are examples of sub-segments of the electrical signals from a patient's heart related to a normal and abnormal beat. The R wave and T wave are also sub-segments.

The dashed lines $V_{PQ}$ (812) and $V_{ST}$ (814) illustrate the average voltage amplitudes of the PQ and ST segments 801 and 805 respectively for the normal beat 800. Similarly the dashed lines $V'_{PQ}$ (812') and $V'_{ST}$ (814') illustrate the average amplitudes of the PQ and ST segments 801' and 805' respectively for the beat 800'. The "ST deviation" $\Delta V$ (810) of the normal beat 800 and the ST deviation $\Delta V_{AMI}$ (810') of the AMI electrogram beat 800' are defined as:

$$\Delta V(810) = V_{ST}(814) - V_{PQ}(812)$$

$$\Delta V_{AMI}(810') = V'_{ST}(814') - V_{PQ}(812')$$

Note that the both beats 800 and 800' are analyzed using the same time offsets $T_{PQ}$ and $T_{ST}$ from the peak of the R wave and the same spans $D_{PQ}$ and $D_{ST}$. In this example, the beats 800 and 800' are of the same time span (i.e. the same heart rate). The parameters $T_{PQ}$, $T_{ST}$, $D_{PQ}$ and $D_{ST}$ would typically be set with the programmer 501 of FIG. 1A by the patient's doctor at the time the CTI 500A is implanted so as to best match the morphology of the patient's electrogram signal and normal heart rate. $V_{PQ}$ (812), $V_{ST}$ (814), $V_R$ (803) and $\Delta V$ (810) are examples of per-beat heart signal parameters for the beat 800.

Although it may be effective to fix the values of time offsets $T_{PQ}$ (802) and $T_{ST}$ (804) and the spans $D_{PQ}$ (806) and $D_{ST}$ (808), it is envisioned that the time offsets $T_{PQ}$ and $T_{ST}$ and the spans $D_{PQ}$ and $D_{ST}$ could be automatically adjusted by the CTI 500A to account for changes in the patient's heart rate, as further described in U.S. patent application number 20040059238 to Fischell et al., which is incorporated by reference herein. The 20040059238 application also describes methods for other aspects of electrogram analysis such as R wave detection.

Sliding-Scale Implementation

Figure 8:
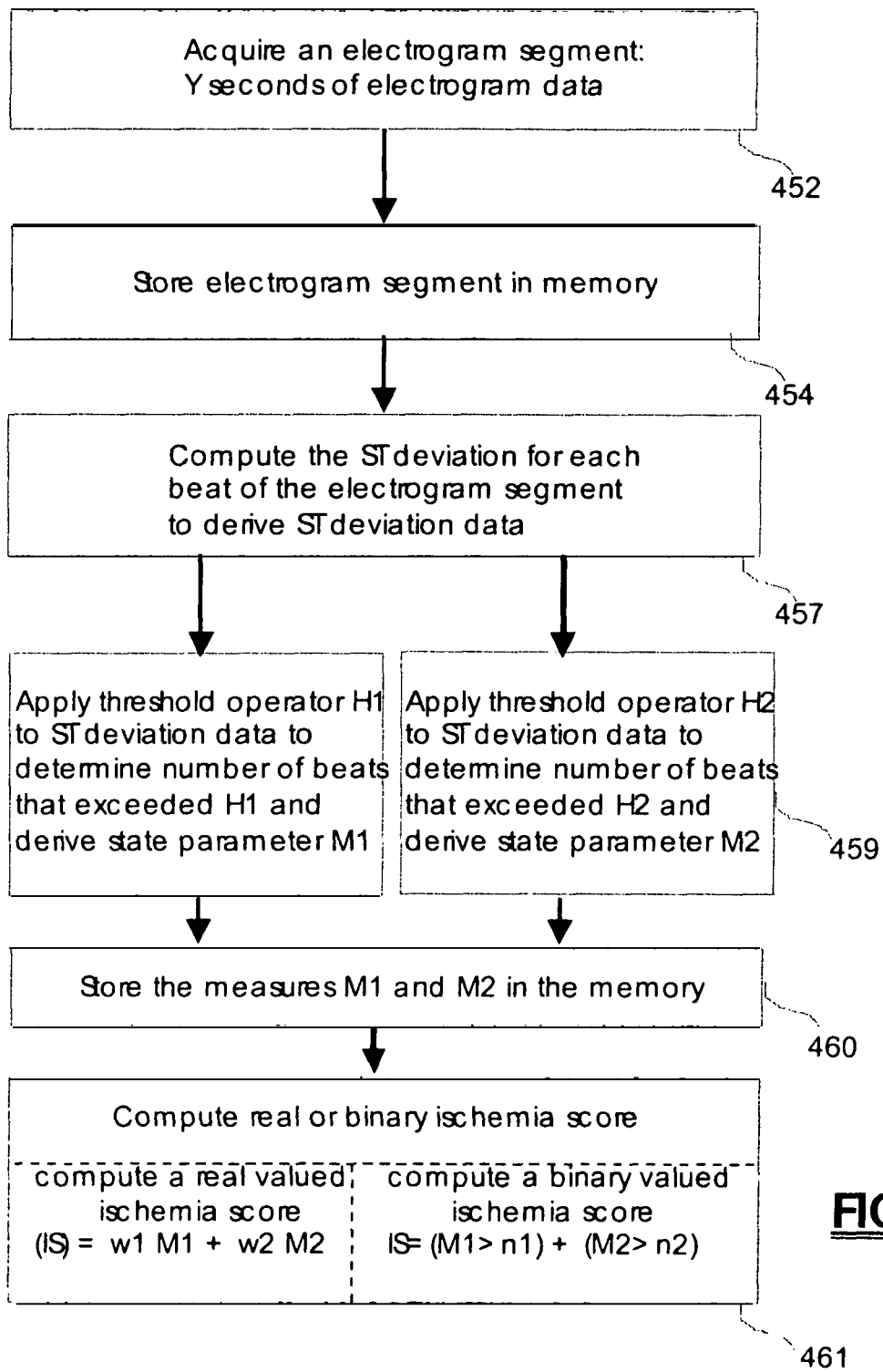
FIG. 8 is a flow chart of a method for detecting ischemia based on ST segment deviations.

FIG. 8 illustrates in the form of a block diagram an implementation of the CTI 500A as may occur using a conditional module 566. Each step of the methods disclosed herein includes the provision of all modules, subroutines, and algorithms needed to achieve that step, and direct references to specific modules of the system 500, are one of various possible enabling embodiments. A heart signal processing program 519a represents a set of subroutines implemented within the control module 518, the sensing module 510, the diagnostic module 516 and the storage module 526. The program 519a begins in step 452 under the control of the control module 518. The control module 518 directs the sensing module 510 to acquire an electrogram segment representing Y seconds of electrogram data. $S_r$ is the data sampling rate in samples per second, thus the total number of samples collected in step 452 is $S_r$ multiplied by Y. It is envisioned that X is a "time out" period which exists between acquiring data segments and would be a time between 5 seconds and 5 minutes with 90 seconds as a preferred value, unless the possibility of a cardiac event is detected, in which case X is preferably 30 seconds. Y would normally be between 3 and 30 seconds with 10 seconds as a preferred value. $S_r$ is typically between 100 and 500 samples per second with 200 samples per second being a preferred value.

Next, in step 454, the program 519a stores the electrogram segment in the memory 550. Next, under the control of the diagnostic module 516 the program 519a moves to step 457, where it computes the ST deviation (as will be further defined below) for each beat in the Y-second long electrogram. The program 519a then moves to step 459, where it categorizes the ST deviations. In particular, the program 519a applies thresholding operators to determine the number of beats in the Y-second segment that exceeded first and second thresholds $H_1$ and $H_2$, corresponding to small and large ST deviations, respectively. Thresholds $H_1$ and $H_2$, which are thresholding operator parameters, are preferably programmable and stored in reference data module 552. The number of beats that exceeded $H_1$ and $H_2$, respectively, is then computed. The number of supra-threshold beats will be referred to as $M_1$ and $M_2$. In step 460, $M_1$ and $M_2$, which may be considered cardiac state parameters, are stored within the diagnostic module 516.

In step 461, the program 850 analyzes the $M_1$ and $M_2$ data of the current electrogram segment and possibly a number (N) of prior electrogram segments to generate an ischemia score that is indicative of whether a patient has ischemia. More generally, the ischemia score may be considered a proxy for the patient's cardiac state. The ischemia score is preferably generated according to a sliding scale that weights the magnitude of ST shifts against the duration of ST shift at a given magnitude. As used here, "duration of ST shift" refers to the length of time over a number of beats or the number of beats for which that the ST shift exceeded a threshold. "Duration" does not refer to the temporal extent of the ST segment of one beat.

Although this example uses 2 thresholds, this technique can be extended to 3 or more thresholds as well. Other cardiac features, in addition to or instead of, ST shifts (or ST deviations) may be measured and compared to their respective thresholding $H_1$ and $H_2$ values. Further, thresholding operator parameters can be adjusted according to current or recent patient state values (e.g., in relation to an event such as the patient pushing a button to indicate that stair-climbing is occurring or medication is being taken). Historical values of $M_1$ and $M_2$, as well as the ST shifts, can be stored in trend data or histograms comprising a specified number (N) of prior electrogram segments. The trend data can be evaluated using sliding scale rules which detect cardiac events after a smaller number of sequential points when these points have larger values for a characteristic such as magnitude (in the case of ST shift). In this case, the ischemic score may be calculated as a function of the area under the curve of the trendline, so that the number of points (duration) required to detect an event is defined to be less when the magnitude of these points is larger. When the trend data for M1 and M2 are stored in two different arrays, these can be combined in the calculation of an ischemia score. Trend data of the cardiac features themselves, such as ST shift values, may be used to calculate the speed of onset of an abnormal cardiac state.

One embodiment of the sliding scale is most easily described with an example. It will be assumed that a single electrogram segment is being analyzed, that the low and high thresholds $H_1$ and $H2$ are equal to 1 mV and 2 mV respectively, and the ST shifts associated with the 5 beats of this example electrogram segment are equal to 1.1 mV, 2.1 mV, 2.1 mV, 1.1 mV, and 2.1 mV respectively.

The $M_1$ value for the segment is 5 and the $M_2$ value is 3. In step 461, an ischemia score (IS) may be computed by application multiplication and summation operators as follows: $IS = w_1 M_1 + w_2 M_2$, where $w_1$ and $w_2$ are the weights corresponding to $M_1$ and $M_2$ (i.e. 5 and 3, respectively, in this case.) The weighting factors $w_1$ and $w_2$ are positively correlated to ST shift magnitude, such that $w_2$ is larger than $w_1$ to give more weight to greater magnitude ST shifts. Thus, the implementation of the above described steps results in a sliding scale test that compares ST shift magnitude to ST shift duration. The "duration" of an ST shift need not be continuous although such a constraint may be imposed. In the above example, the 3 electrogram beats that exceeded $H_2$ may have been interrupted by the segment that did not exceed $H_2$. In addition to testing a weighted sum ($w_1 M_1+w_2 M_2$), it may be desirable to check for ischemia by comparing $w_1 M_1$ and $w_2 M_2$, respectively, to separate thresholds, i.e. performing separate tests for relatively lower and greater ST shift magnitudes, respectively. As an example of both separate and mixed (i.e. weighted sum) sliding scale implementations, a first detection rule may dictate that at least 6 out of 8 heart beats (from a plurality of heart beat waveforms which may be partitioned into a particular segment) must exceed a lower first magnitude threshold, and a second detection rule may dictate that at least 3 out of 8 beats must exceed a higher second magnitude threshold, and a third detection rule may dictate that if at least 2 out of 8 beats exceed the higher second magnitude threshold and at least 5 out of 8 beats also exceed the first lower magnitude threshold that a medical event is detected. The idea illustrated with this example is that, although the sliding scale rule normally requires 6 out of 8 beats to detect a medical event at the lower magnitude threshold, the $3^{rd}$ rule dictates that since the higher magnitude threshold has also been exceeded, then this information can be used to adjust the duration criterion in a manner which is a functional compromise between the criteria delineated in the first 2 detection rules.

Alternatively, the IS may be computed as a binary quantity by evaluating $IS=(M_1>n_1)+(M_2>n_2)$, where $n_1$ and $n_2$ are first and second comparison operands that are inversely correlated to ST deviation magnitude, such that $n_2$ is smaller than $n_1$. Again, this scheme implements a sliding scale that trades off magnitude and duration. In this case, the "+" operator denotes a Boolean "or" operation.

A number of adjustments can be further incorporated into the example just provided. First, the magnitude thresholds can be adjusted based upon the growth rate of the ST-shift as may derived from evaluation of the trend data, so that rapid ST-shift onset is evaluated using lower or higher thresholds. Alternatively, the equation may be adjusted so that a number of tests are provided and each are weighted in the cardiac measure Cardiac_status=$(m>m1)*(dm1>D1)*k1+(m>m2)*(dm2>D2)*k2+q*k3$, wherein the cardiac status score is derived from a first term which requires that dm1, the duration that the ST shift magnitude exceeds M1, is longer than D1, a second term which requires the event to be larger than M2 and dm2 (the duration of M2) longer than D2, and a third term wherein a measure q is scaled according to k3, and where k1, k2, and k3 are coefficients which have preferably been clinically derived. Again, in this equation, the ">" operator may perform a compound operation. Alternatively, a cardiac_status test could be implemented as Cardiac status=$dm1*k1+dm2*k2+q*k3$, with k1, k2, and k3 again being appropriately chosen. As yet another alternative, cardiac_status could be implemented as Cardiac status=$\Sigma[(m_i>M1)*k1+(m_i>M2)*k2]+q*k3$, where m1 is the magnitude of the i'th heart beat (or segment or other indicia of duration).

The thresholds for magnitude, duration, or other characteristics can be derived statistically from normative data, can be derived statistically to detect abnormality at a specified probability level, can be adjusted based upon the number of tests that are performed (and the correlations between these tests) and can be adjusted based upon factors such as heart rate and patient state. The thresholds can also be derived during balloon occlusion, stress tests, or other procedures which may be used to determine the extent of expected changes for each patient. The cardiac measures that are evaluated in the equation may be computed based upon data sensed from an one or more sensors adapted for placement inside a human patient to sense the electrical signal from the patient's heart, the electrical signal being an electrogram which consists of a multiplicity of beats, or may be derived using data from multimodal sensor data including for example, electrogram data, pressure data, sonic data, and chemical data. Further the data be obtained from sensors placed outside of the heart in order to obtain information related to breathing, brain activity, posture, muscular exertion, and blood pressure.

In the present invention excessive ST shift may be identified using only two occurrences of 6 out of 8 beats (or 5 out of 8 beats) provided that the ST shift was more than a second higher threshold. This second higher threshold could be preset or may be dynamic and based on some percentage (e.g. 120%) of the standard detection threshold. Such a sliding scale function that inversely weights two heart signal parameters, e.g. magnitude and duration, provides an advantage of more rapid and comprehensive abnormal event detection (while maintaining a similar level of specificity), since an acute change in amplitude of ST level can require less beats in order to trigger an alert, as long as these events are relatively more abnormal. As already described, the values of the thresholds or weighting factors may be altered based upon the onset characteristics of a cardiac feature. For example, if the amount of S-T shift has changed in its variance (i.e. become less stable), growth, or acceleration (i.e., change in growth over time), as may be assessed using the trend data 560, then the values of the thresholds or weighting factors can be adjusted to address the characteristics of this onset in a desired manner. This feature is important because the rapidity of the change of a feature such as the ST segment amplitude also provides information regarding the underlying causes change. For example, if an ST shift occurs very rapidly at a normal heart rate, then a likely cause of the shift is an acute occlusion of a coronary artery. There are different ways to incorporate this information into an ischemia score. According to one method, the rapidity of the shift, which may be derived from the trend data, may be added as an additional variable to the IS. For example, IS could be set equal to w1 p1+w2 p2+w3 p3, where the first two terms are the sliding scale terms, as above, and the last term weights a measure derived from the average rate of change of the ST shift p3 with a weighting parameter. This average rate of change will be an approximation in the case where electrogram segments (as opposed to a continuous electrogram) are used to compute the average, since ST changes may occur in the gaps between electrogram segments.

The rate of change of the ST shift could also be used to modulate weights or thresholds. For example, for the sliding scale IS=w1 p1+w2 p2, the weights w1 and w2 could be an increasing function of the rate of change of the ST shift. As yet another alternative, the rate of change of ST shift could be compared to its own associated threshold, with a negative test indicating that no acute occlusion is detected.

More generally, the conditional module 566 has the capability of computing a function that maps different heart signal parameters and function parameters to values that serve as a proxy for a patient's cardiac state. For example, a function value of 0 may correspond to normal while a function value of 1 may correspond to ischemic. One heart signal parameter may be the magnitude of ST segment shift while another heart signal parameter may be the duration of an ST segment shift. By applying programmable function parameters to heart signal parameters, for example by comparing a heart signal parameter with a programmable threshold (which is also a function parameter), the conditional module 566 can be used for patient specific diagnosis, alerting etc.

The present invention is in no way limited to analyzing ST segment changes. For example, because ischemia affects the QRS complex, as is well known, it may be desirable to compute a QRS related heart signal feature such as QRS width, the magnitude of any of the QRS waves, or the slope of any of the QRS waves and to decrease the duration required to send an alert signal as a function of the size of the abnormality of the feature. Additionally, the morphology of the QRS complex may be examined, and determined to be normal or abnormal depending on whether or not the QRS is fractionated. These QRS parameters may be stored over a plurality of beats, and an IS, or other cardiac measure, computed as a function of these parameters.

Rather than using single beats, average beats ("A-beats") can be computed from 2 or more beats and these can be compared to a criterion. A-beats can be computed by measuring 2 or more beats separately and then averaging these measurements together, or can be computed by averaging together 2 or more beats in the time or frequency domain and then measuring the average of this activity in each "a-beat" of an averaged electrogram.

A state module 568 can determine if the state of a patient has changed, for example, the patient has transitioned from an awake to sleeping state. The state module 568 can also respond to a button press of a patient, or can refer to the time of a clock and compare this time to time values which are stored in the control program 519 of FIG. 1B which indicate relevant time values. Such time values may be when the patient normally goes to bed or wakes up. The state module 568 can cause sensed data to be tagged with the current state, which can lead to a modification in how it is stored or compared to reference data. For example, if current data are indexed as being from a sleeping state, then it may be only compared to reference data of a similar state. As a further example, in step 459 (FIG. 8), the state module 568 can set the thresholds $H_1$ and $H_2$ according to whether the patient is awake or asleep. A control law module may also use the state module to compute a state, such as a diseased or normal cardiac state, but this is related primarily to cardiac activity itself and is computed differently than the patient state.

Patient-State Implementations

Figure 9A:
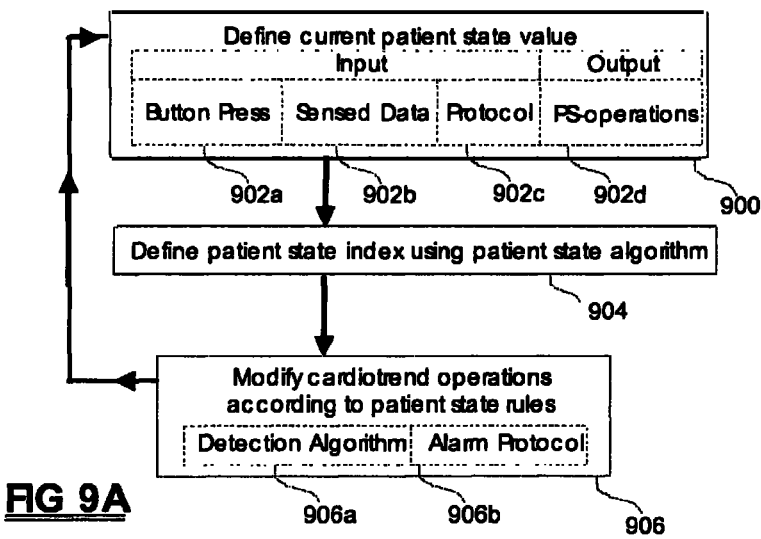
FIG. 9A shows a method by which a patient's state is used to adjust one or more of the cardiotrend operations by modifying the operation of the detection algorithm, or the operation of the modules of an alarm module, in order to adjust the detection of abnormal cardiac activity or the generation of alarms, respectively.

The CardioTrend system can utilize the patient's state to adjust the evaluation of cardiac activity, the detection of abnormal events, and the generation and selection of alert signals. FIG. 9A shows a method by which the patient's state is used to adjust cardiotrend operations such as the operation of the detection algorithm (as may be implemented by the comparison 564, and result 576 module of the diagnostic module 516), or the operation of the alarm module 522, in order to adjust the detection of abnormal cardiac activity or the generation of alerts, respectively. In the context of FIG. 9A, it is assumed that patient electrogram data has been acquired as previously described with reference to FIG. 8.

In FIG. 9A, a patient state value is first defined in step 900. For example, the patient state value can be computed based upon patient input, evaluation of sensed data, the pre-defined patient state values of a treatment protocol or other information. The current patient state value can be defined manually by a patient depressing a button 902a to indicate that an event such as "walking up stairs" is occurring. The button may be pressed by the patient at the beginning of the activity, at the bottom of the stairs, and then released (or pressed again) at the top of the stairs. The patient state value can also be defined automatically by evaluation of sensed data 902b that are sensed by sensor such as an EMG sensor or accelerometer. The sensed data are evaluated to determine the type of activity that a patient may be engaged in (e.g., sitting or walking up stairs). Additionally, a patient state value can be defined by a protocol 902c which may be programmed by a physician. Such a protocol can indicate periods and times in which the patient states are likely to have certain values (e.g., the protocol might state that from 11 p.m. to 7 a.m. the patient is usually in a sleeping state), or can be defined in relation to certain events (the patient may normally take medication at a certain time of day), and can include durations after which the patient's state is likely to change (the patient may usually exercise for 20 minutes and then stop).

Patient state values can refer to: an emotional state (upset or angry); and arousal state (anxious or relaxed); a comfort level (feeling good or experiencing chest pain, tingling, numbness, or heaviness); activity level (awake or asleep; resting or exercising; walking, or ascending or descending stairs); the administration of a drug as well as an amount. Patient state values may also reflect environmental variables such as "lift off" and "arrival" of a flight on which the patient is a passenger, altitude while traveling, and temperature. Defining the current patient state value 900 can include performing patient state operations 902d ("PS-operations"), which can include updating the current value of at least one patient state array (e.g., 920).

In step 904 the patient state index parameter is calculated and updated. The patient state index parameter reflects the functional patient state which is used to guide operation of the CardioTrend system. In step 904 the patient state index parameter can be defined according to patient state algorithms ("PS-algorithm"). For example, a "hold duration" PS-algorithm may be selected wherein the patient state index parameter is maintained based upon recent patient state values, and a current patient state value is ignored for a specified amount of time, after which the patient state index is set according to the most recent patient state value of the array.

Once the patient state index parameter is defined, cardiotrend operations are modified according to patient state rules (PS-rules) 906 and then the method returns to step 900. PS-rules determine how the patient state index parameter alters the operation of the cardiotrend system. For example, a PS-rule may dictate the adjustment of the detection algorithm 906a implemented by the diagnostic module 516 using a 'threshold PS-rule'. The threshold PS-rule can dictate that if patient state index is defined as exercising ("E") then the detection algorithm may be changed, so that criterion level required to detect abnormal ST deviation may be increased compared to that used when the patient is resting ("R"). By adjusting the level of ST deviation according to patient state (e.g., activity level), the threshold levels for detection of normal and abnormal cardiac activity may be sensibly adjusted (i.e., made physiologically appropriate and patient specific).

The patient state index parameter may also be used to adjust the alarm protocol 906b implemented by the alarm module 522 using a 'repeating-alarm PS-rule'. For example, if an alert signal has been triggered and the patient has turned the warning signal off then a subsequent alarm may not be issued, even if a subsequent abnormal event is detected, as long as the patient state index has remained constant. The repeating-alarm PS-Rule may dictate, in this example, that if the patient state index hasn't changed, then another alarm is not provided in response to subsequent detected abnormal events that fall within a specified time period (e.g., 2 minutes) unless these subsequent abnormal events exceed a secondary threshold. This feature deters the cardiotrend device from becoming a nuisance by issuing multiple alarms while the patient is still in the same state (e.g., exercising) as reflected by an unchanging patient state index and maintaining a level of ST deviation that is above a first specified threshold but below a second specified threshold. In a further embodiment, the patient state index values may also be stored in an array and used both in the calculation of the current index value as well as to determine any CTO, as indicated by block 906c in FIG. 9A. Module 906 will be further described below with respect to the segmentation embodiment corresponding to FIG. 12. In this manner, the method of FIG. 9A may be used to modify the segmentation and evaluation of cardiac data including detection of abnormal events, and the subsequent triggering of alarms according to a patient's state. The steps of the patient state method of FIG. 9A can be accomplished by the state module 568 of the diagnostic module 516 and related data such as the patient state arrays can be stored in memory by the storage module 526.

Figure 9B:
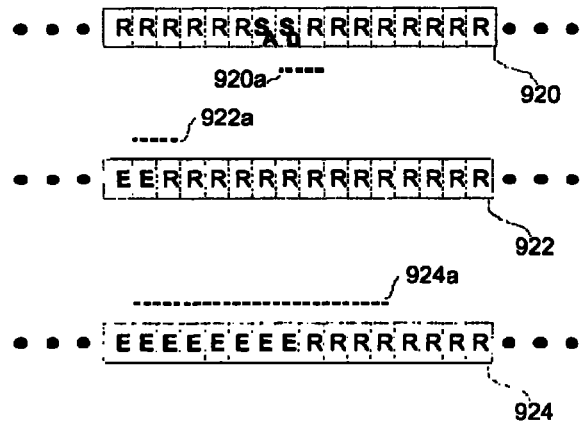
FIG. 9B shows several examples of patient state arrays applicable to the method shown in FIG. 9A.

FIG. 9B shows several examples of patient state arrays 920, 922, 924. A patient state array 920 comprises a series of recent patient state values. The first 6 values of the patient state array 920 show that the patient was resting (R), then two patient state values were defined as states where the patient was ascending stairs ($S_A$) and then descending stairs ($S_D$). Following this stair-related activity, the patient state values indicate that the patient returned to a resting state. In step 904 of FIG. 9A, the patient state index for this array could be calculated by a PS-algorithm, in this case a PS-window algorithm, which operates so that if a recent patient state was (S), then the patient state index is temporarily defined as S even if the current patient state value is R while R falls within the duration defined by the PS-window 920a. The PS-window 920a is shown graphically as a dotted line. In this example, the window duration is defined as a period equal to half the total number of S patient state values which consecutively occurred in the patient state array. In other words, $D_H=D_S*0.5$, where $D_H$ is the duration the window is held and Ds is the duration of the patient state S values (regardless if it is $S_A$ or $S_D$). Alternatively, $D_H=S_A*2$, defines a PS-window operation that would yield the same duration of the window 920a. In this latter case, $S_D$ is ignored (possibly because stair climbing affects ST deviation levels while stair descending does not).

The PS-window feature is useful in reducing false alarms. For example, even though the current patient state value may be defined as resting R, when a patient has recently finished climbing the stairs an ST-deviation may occur that is related to this recent stair-related activity. Although a particular ST deviation may be defined as abnormal for a resting patient, this deviation may be normal when the same patient is climbing, or has recently climbed, the stairs. In the prior art, although different ST-deviation thresholds may be set for different patient activity levels, this art does not address the issue of what may occur when the effects of a previous patient state alter the cardiac activity of the present patient state. Unlike the prior art, the use of PS-algorithms allow for the adjustment of the cardiotrend operations based upon a) the existence of prior patient states, b) the duration of prior patient states, c) the duration since prior patient states, and d) a combination of the current and past patient state values. The cardiotrend system thereby also can address the effects of hysteresis within the cardiac activity being measured.

In 922a a PS-window is again graphically represented. This PS window 992a will cause the patient state algorithm of step 904 (FIG. 9A) to define the patient state index as "exercising" rather than "resting" (E rather than R) and occurs using a PS-window algorithm which implements two PS-window algorithm rules. The first PS-window algorithm rule dictates that a PS-window is not incurred until the exercise state "E" spans at least 2 sequential patient state values of the patient state array. Accordingly, if the exercise session is brief, causing only one value of the patient state array to be labeled with "E", then the subsequent patient state value can become the functional patient state index used in step 906. This rule is illustrated graphically where the PS-window does not begin until the second "E" of the patient state array 922. The second PS-window algorithm rule is that $D_H=D_E*0.5$, so that the PS-window lasts half as long as the patient exercises. In 924a a PS-window algorithm is again graphically represented. Here, the PS-window duration is defined to be twice the duration spanned by consecutive patient state values calculated as exercise (E), and the duration does not start until the last of the exercise patient state values occurs.

Although FIG. 9B shows examples of patient state arrays corresponding to a single type of patient state value (i.e. patient activity level), in the preferred embodiment, a number of arrays will track a corresponding number of different types of patient state values. The patient state algorithm of step 904 (FIG. 9A) may define the patient state index based upon the values in all of these arrays. The different arrays are preferably organized in a parallel, time aligned fashion. In a further embodiment, one of the arrays includes time of day information to allow circadian rhythms to be taken into account, although sensed data may also be used to derive these rhythms. Although multiple arrays may be used, values from only one patient state array may be derived and then used to calculate a patient state index. Further, different types of patient state arrays can be selectively utilized in the calculation of the patient state index at different treatment periods.

FIG. 9B also shows an array of values for a selected heart signal feature ('F1') in parallel with patient state arrays 920, 922, and 924, so that each heart signal feature value is effectively tagged with at least one corresponding patient state value. This structure permits heart signal feature data to be analyzed according to patient state. More particularly, the self-norm data analysis described elsewhere in this specification may be performed by grouping together data according to patient state values, and separately analyzing the different groups. Thus, for example, self-norm data associated with exercising may be derived separately from self-norm data for resting.

The illustrative examples of FIG. 9B, which are used by the method of FIG. 9A, show specific embodiments which can be easily generalized and expanded. For example, the patient state arrays can contain various different alphanumeric symbols each of which can qualitatively indicate different patient state values, or which may even quantify these state values. "E1" can be gentle exercise, where "E6" may indicate demanding exercise. The patient state window algorithms can consider both current and past values of the patient state array in determining patient state index. For example, a transition from exercising to walking can incur a different PS-window algorithm than that used for a transition from exercising to resting. Since step 904 can occur in a regular, irregular, or event-related manner, each value of the patient state array may not represent an equivalent duration. The one or more values of the patient state array can be time-stamped or otherwise labeled as to its duration. Further, the values of the patient state array which are considered by step 904 in the determination of the patient state index parameter, do not have to strictly be based upon adjacent consecutive cells of the patient state array.

The patient state rules used to modify CTOs (step 906 of FIG. 9A) can realize a variety of functions and algorithms in order to provide novel benefits to the cardiotrend system 500. For example, instead of maintaining a threshold associated with exercising due to the existence of a PS-window, the step 906 can use a patient state rule which adjusts the critical threshold defined for ST-elevation as a decaying function. In other words, a PS-rule can be implemented in which when the patient state index changes from 'E' to 'R' the threshold criteria transitions from the level used during an 'exercise' patient state to that used during the 'resting' patient state as a decay function (rather than simply waiting until the end of the PS-window hold duration in order to alter the ST-deviation threshold level in a stepwise manner). In this particular embodiment, the threshold criteria change according to decay function which may be similar to that which would result using a moving average of a "sliding window", however, when the decay functions are complex, such a sliding window algorithm would not work well.

The use of the patient state array offers significant features over the implementation of a simple sliding-window based adjustment of threshold criteria values. For example, the method can serve to dynamically and automatically adjust the duration, the weights, and the lag or lead time of the sliding-window, according to the history of values of the patient state array. By way of illustration, both the duration and activity level of the exercise period, as reflected it the patient state values of the array, may serve to adjust the characteristics of a threshold decay function.

Figure 11:
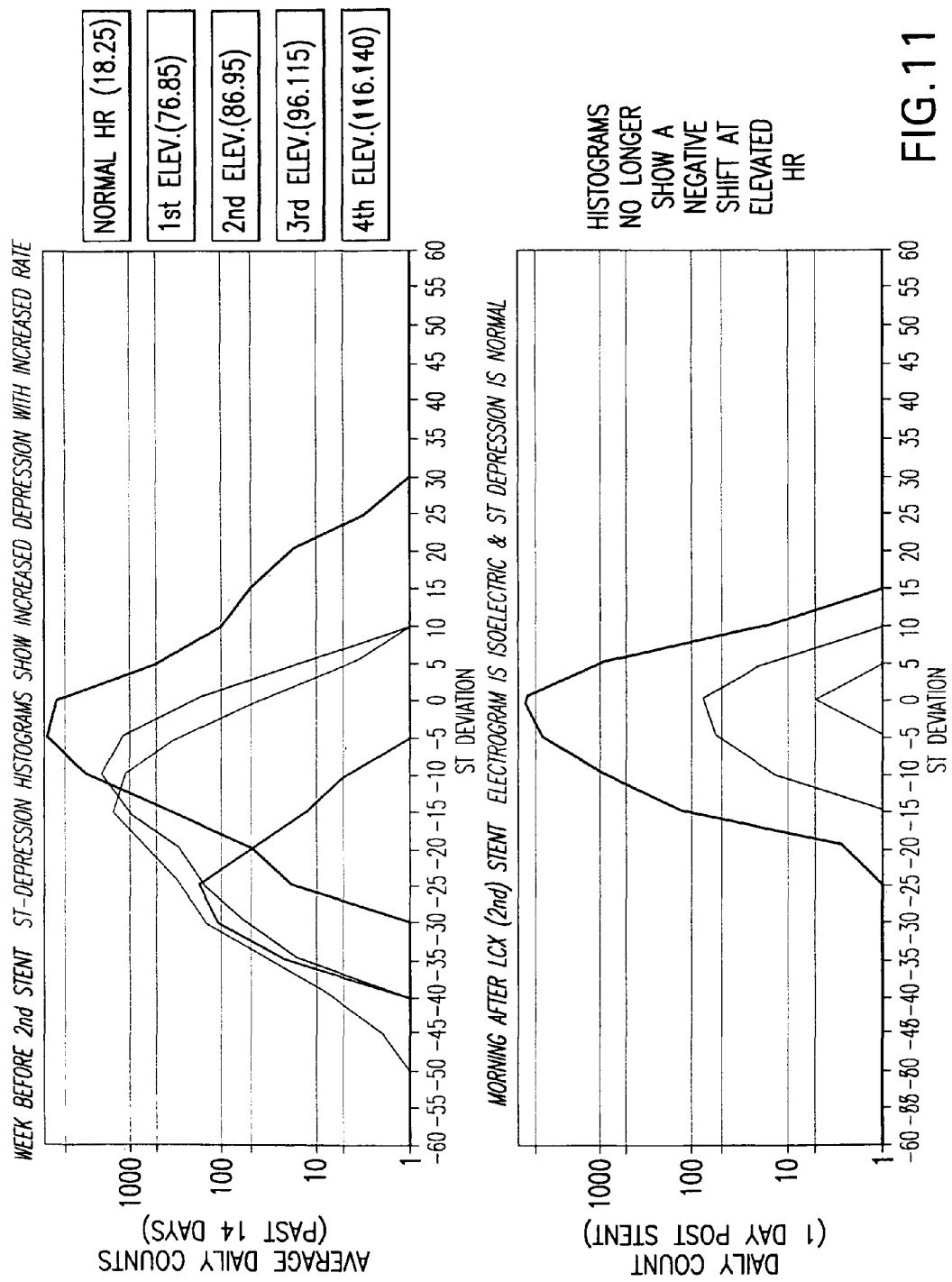
FIG. 11 shows exercise-induced ST deviation, as a function of heart-rate, computed from electrogram data from a patient before and after a therapeutic stent procedure.

In one preferred embodiment, a PS-rule can be implemented in which the current measure of ST deviation which occurs when the patient is sitting at rest is evaluated in relation to a faster heartbeat which existed during a recent exercise routine. In this example, the ST deviation data would be evaluated and/or stored by the cardiotrend system 500 using histogram data classified for the higher heartbeat range. This method deters unwarranted alerts. FIG. 11 shows exercise-induced ST deviation, as a function of heart-rate, computed from electrogram data from a patient before and after a therapeutic stent procedure. The upper graph shows that as heart-rate increases the amount of ST deviation moves from a mean value of about −10 to a mean value of −25. The x-axis is ST minus PQ voltage difference or 'ST-deviation' in pre-calibrated units used by the device. The y-axis is the number of counts or 'beats' that had an ST minus PQ (ST deviation) value of the x-axis bins (=/−2.5 due to a bin width of 5). There is a clear shift to the left as heart rate increases across the 5 heart-rate ranges.

After the stent procedure the exercise induced cardiac changes show a decrease both in the number of counts at the higher heart-rate ranges (the heart is being more efficient, although a direct comparison of the top figure with the bottom figure is complicated by the fact a relatively smaller amount of data were used to calculate the bottom figure) and also in magnitude of ST deviation which occurred within these higher ranges. The most common ST-deviation is now apparently near the zero level since the source of ischemia has been removed by the stenting procedure. The top figure shows a pretty sick individual and the bottom an individual who is now functioning at a normal level. In reality, patients will likely be somewhere between these two scenarios and while some ST deviation would be expected, and allowable, at higher heart-rate ranges, this same amount should cause an alarm when the patient is at rest, or showing only a slightly higher heart rate. In other words, in a patient with ischemia, various allowable amounts of ST-deviation may be expected at different heart rates. As per the figure, if the heart-rate is elevated at 76-85 BMP occasional ST-deviations of about −10 are expected, while 86-95 BMP would decrease this value closer to −20. Using the PS-Rule, although the present heart-rate may only be between 38 and 75, the permissible amount of ST deviation would be calculated based upon a threshold set for a heart-rate of 78-85 or 86-95 since exercise (or other legitimate cause of acute increase in heart rate) occurred in the recent past as reflected by a patient state array. The PS-Rule thereby allows current data to be evaluated as if it occurred with a different heart-rate than is present at a particular time. A recent heart rate, rather than the current heart rate, may be used to determine settings for evaluating current data. Indeed, storage of historical patient state data may allow the system to compensate for the different types of ST-deviation vs. heart rate hysteresis associated with healthy and chronically ischemic patients, respectively.

Figure 9C:
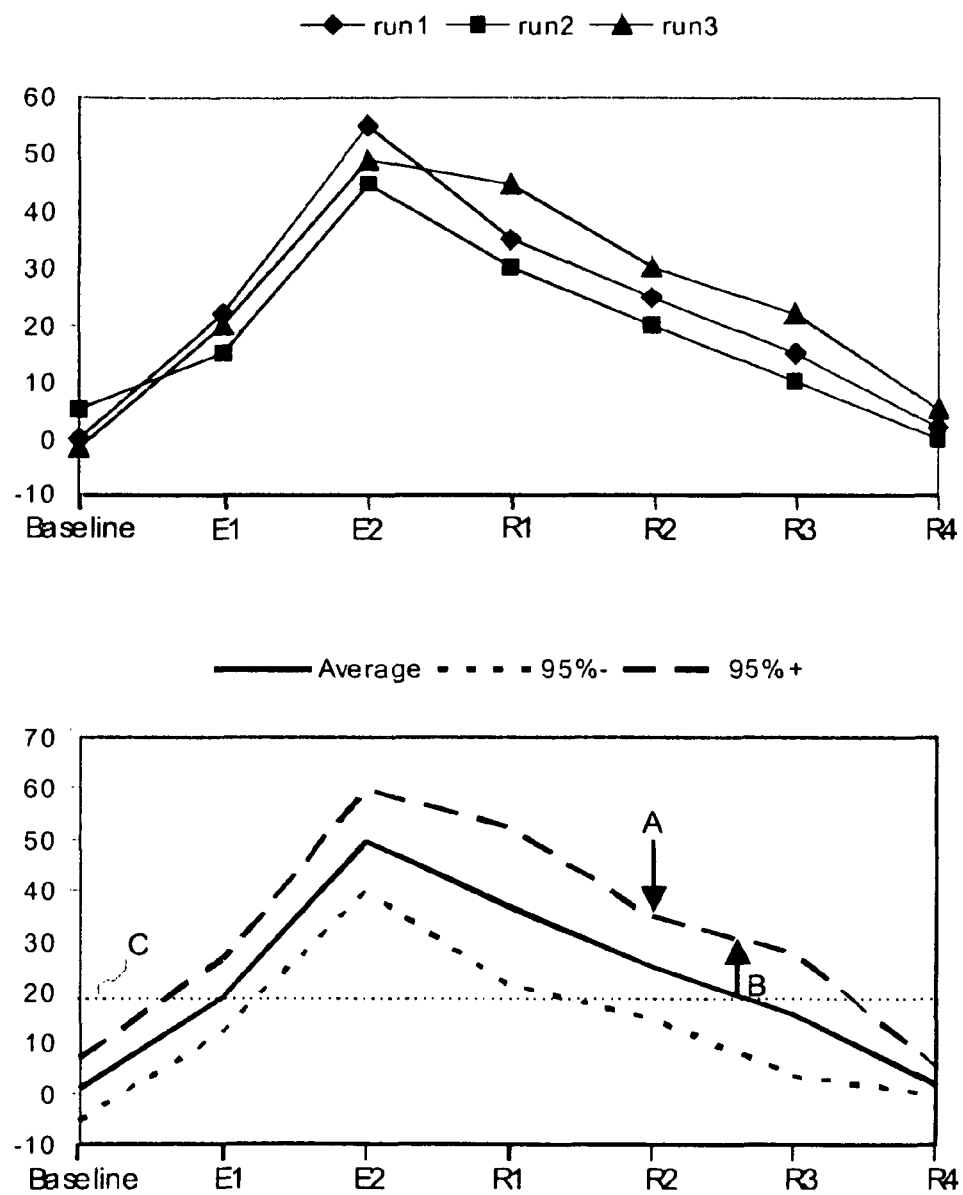
FIG. 9C shows hypothetical data applicable to the method shown in FIG. 9A.

When a patient transitions from exercising to resting, the PS-rule can dictate that the threshold level for detecting ST-deviation is changed over time according to a function which calculated using self- or population-normative data. Such a function is generated from hypothetical data of FIG. 9C. FIG. 9C has an upper graph which represents the level of ST-deviation for an individual across 3 repeated runs of a stress test. The x-axis comprises categorical items which represent different test conditions: a baseline measure of ST-deviation; two time-points acquired during exercise (E1 and E2) which may be times at 5 and 10 minutes through the activity; and, 4 time-points acquired during the recovery period (R1, R2, R3, R4) which may have occurred at approximately times 1, 2, 3, and 4 minutes after the termination of exercise. The y-axis is ST-deviation, and is in arbitrary units. The stress test may simply consist of the patient ascending several flights of stairs. This data may then be used to generate the mean functions for both exercise and recovery as well as confidence limits, such as the 95% (or 99%) confidence limits, as is shown in the lower graph of FIG. 9C. In this case the graph in the lower panel has been computed upon self-norm data from the upper panel, but it could just as easily have been computed from population normative data.

Using the patient state array, a PS-rule can change the threshold level for detecting ST-deviation over time according to an appropriate function, such as that of FIG. 9C. If the patient state array indicates that 2 resting patient states (R) have occurred since the end of the last exercise state (E), and patient state values are being computed once per minute, then the current measurement of ST-deviation can be compared to the ST-deviation function at 2 minutes (R2). More specifically, the function data includes the upper 95% confidence limits (long-dash curve of lower panel in FIG. 9C), and an abnormal cardiac event is detected if current ST-deviation exceeds the ST-deviation confidence limits at 2 minutes (i.e., a value of about 40, see arrow "A" in FIG. 9C). Current ST-deviation values for a patient can also be computed during exercise, as a function of time since the start of exercise. For example, at time-point E1, or about 5 minutes into the exercise routine, the ST-deviation should have a value of about no more than 25 (the upper 95% confidence limit). If the ST-deviation is closer to 50 at this point, then an alarm may be indicated. While a value of 50 is not abnormal 10 minutes into the exercise routine, this level of ST deviation normally does not emerge earlier in the activity period and the abnormal rate of increase during induction can be used to detect abnormality. Further, if cardiac activity does not change concurrent with, subsequently to, the initial period of exercise, then this may also indicate unhealthy cardiac status. In FIG. 9C, if a measure of the patient's cardiac activity (e.g. heart rate) was below the lower confidence interval (smaller dashed lines in FIG. 9) then this could indicate a failure of a normal cardiac induction response to increased demand due to initiation of exercise.

The historical record of patient state can be used to contextualize a given heart-rate. For example, although the heart rate may be around 130 beats per minute after 2 minutes of exercise, and also after 30 minutes of exercise, the heart may be in a very different mode at the end of the exercise period.

By automatically dividing the exercise period into intervals (e.g., into a first and second half) using the historical record of a activity of the patient state array, heart rate activity associated with either of these intervals, or with a peak exercise interval, may be differentially assessed. One or more measures of cardiac (e.g. heart rate) activity in each interval can be compared to each other or to reference threshold values, and each may be a different variable in a multivariate index of cardiac status. In other words, the historical record of patient state values enables the same cardiac measurement to serve as more than one variable in an equation, where each variable may represent that measurement at different intervals in relation to an event. A measure of heart rate, computed upon each ⅓ interval across a full exercise period, can be assessed as a separate variable or assessed in a different manner. This feature is well served by the patient state array which provides a historical record. Rather than automatic partitioning of activity, button presses may be provided by the patient to mark the patient state array with different values related to the start, peak, and end of an exercise regimen.

Although the patient may normally exercise about the same amount each day, this may vary on different days. The recovery function used to set a threshold value can be adjusted based upon the level and duration of activity, or a peak level of a measure, which occurs on a particular day. For example, looking at the lower panel of FIG. 9C, if the exercise duration only lasted until the first time-point (E1), then the slope of the recovery curve, and the upper 95% confidence limit (see arrow "B" in FIG. 9C), could be applied to the ST-deviation level which was present at the end of the exercise (level marked "C" in FIG. 9C).

Threshold functions can be based upon reference data that is collected during normal or abnormal cardiac states. Subsequent comparisons can then identify cardiac activity which is either statistically different than normal activity, or statistically similar to abnormal activity. If the graph in the lower panel of FIG. 9C, was computed upon data collected from post-stent patients who show normal or slightly abnormal ST-deviations, then the upper confidence limit function is used for the threshold function and current ST-deviations which exceed this function may be deemed abnormal resulting in an alarm warning. Alternatively, the graph can be computed upon data collected from pre-stent patients who show abnormal ST-deviation, and the lower confidence limit function may be used, wherein current ST-deviations which exceed this function may be deemed abnormal resulting in an alarm warning. Further, analysis of data collected during ischemic and non-ischemic periods can be combined to build threshold functions with desired characteristics, such as maximally discriminating between normal and abnormal cardiac activity (e.g., by considering the sizes, distributions, and types of changes which occurred between the two periods). The graphs of FIG. 9C may be computed for ST deviations (including both ST elevations or ST depressions) or other measurement of EKG activity.

Segmentation of Cardiac Data

Figure 12:
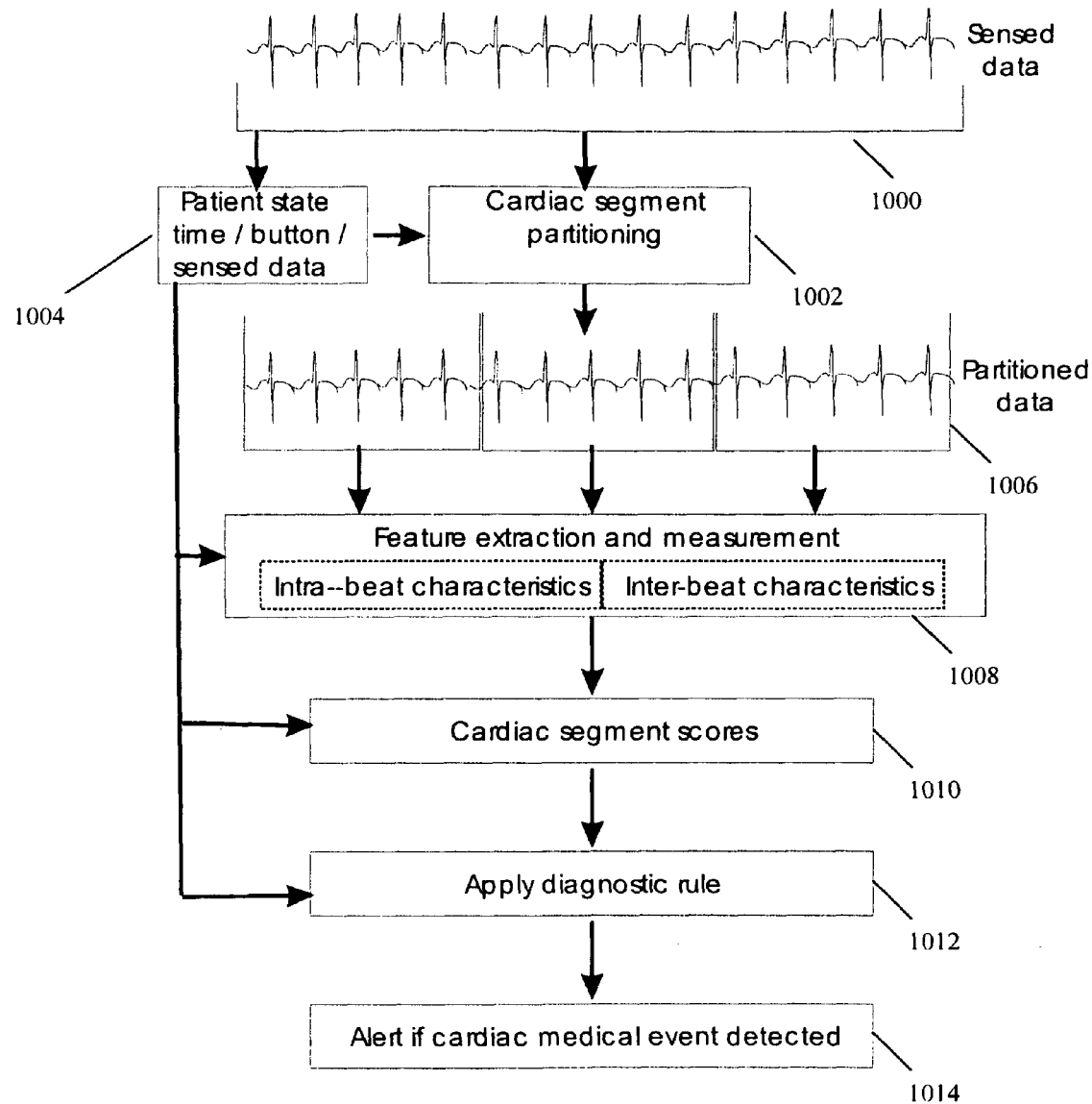
FIG. 12 shows the steps associated with a segmentation based cardiac event detection scheme that utilizes patient state information to perform various operations; and, FIGS. 13a, 13b and 13c each show a table that contains information regarding the segmentation based cardiac event detection scheme outlined in FIG. 12.

FIG. 12 is a flow chart that shows a detection scheme that may be implemented by the control module 518, sensing module 510 and diagnostic module 516, all of which are shown in FIG. 1B. The scheme shown in FIG. 12 provides a framework for interaction amongst these different modules. The scheme shown in FIG. 12 involves partitioning data into segments that may be time based or based on physiological events (heart beats, breaths etc.) Any type of data may be partitioned. For example, the data to be partitioned may be an electrocardiogram or may consist of mechanical data such as measures of left ventricular pressure, volume or strain. In the following discussion, for purposes of explanation, it will be assumed that that the data has the same periodicity as the cardiac cycle.

Segments are scored; these scores can be quantitative over a range (e.g., 0 to 10, or −10 to 10), where lower (or negative) scores may signify a lower amount or degree of abnormality, or may be binary (e.g., 0 or 1) indicating that a segment is classified as normal or abnormal. The detection of a medical event then occurs using at least one "diagnostic rule" which serves to evaluate the set of segment scores and detect/quantify a medical event that resides within the cardiac data. The segment score evaluation may involve the integration of scores associated with segments derived from multiple sensors, which in turn may be associated with different sensor modalities. A medical event can be the occurrence of abnormal cardiac activity, a worsening of cardiac activity, or any occurrence of a particular type of cardiac activity which has been defined as a medical event.

FIG. 13a is a table that shows various parameters associated with the segmentation scheme. The first, second, and third columns show the parameter class, the parameter, and the parameter value, respectively. The parameter class pertains to the relevant operation in the segmentation method. For example, in rows 1-2, the parameter class "Sensor" corresponds to a physical device such as an electrode. If there are two sensors, Sensor 1 and Sensor 2, each has a corresponding parameter in the second column, with a corresponding parameter value in the third column, 1 or 0 (on or off). Other parameter classes and parameters will be discussed further below.

Returning to FIG. 12, block 1000 depicts sensed electrogram data, which is assumed to already have been filtered and otherwise appropriately processed by the sensing module 510, as described with reference to FIG. 2. In step 1002 (FIG. 12), the sensed data is partitioned by the partitioning module 517 (FIG. 2). In some embodiments, the partitioning rules may be adjusted or selected based upon information the partitioning module 517 receives regarding the patient's state, as is indicated by the flow of information from block 1004 to block 1002.

The partitioning module 517 may partition the data using one of a set of partitioning rules, in order to produce cardiac data segments, each of which have a selected duration, or which contain a selected number of beats. Either of these types of partitioning rules may be selected, or adjusted, based upon specified heart-rate ranges. Further, the partitioning rule may dictate that segmentation of the data occurs in a manner that changes over time. For example, segment durations may change over time relative to the onset of an event such as the patient standing up, which will be reflected in the patient state data that is passed in block 1004 to block 1002. An event such as standing up may produce a transient set of changes in the patient which should be evaluated in differential manner to data obtained at other times since standing up produces cardiac changes related to the changes in blood pressure which accompany the transition from not-standing to standing.

In one instance, if an event occurs then the data which is partitioned subsequent to the event may comprise a set of cardiac data segments containing 3 segments each of which contain 3 beats, followed by 3 segments each of which contain 6 beats, followed by segments each of which contains 10 beats. This partitioning strategy emphasizes the data related to each beat that occurs immediately following an event because the segment score is computed upon less beats than in the segments that are more distal to the event occurrence. This strategy also serves to emphasize acute changes which may occur after the event. Because each patient may demonstrate different and distinct temporal patterns of activity tied to an event, the ability to adjust the segment size may allow the tailoring of the detection routines in relation to patterns previously found within a particular patient. Again, the event may be reflected in the patient state values and the partitioning rule is invoked based upon detection of this event.

As another example, the partitioning rules which are used immediately (e.g. for the first 10 minutes) after a patient exercises, may be different than those used during the remainder of the day. This may be done in order to emphasize or de-emphasize the cardiac phenomena which are acutely manifest in the post-exercise period. Partitioning rules can also dictate the amount of time which occurs between segments and the amount of segments collected per interval of time (e.g. two 10-second epochs per minute). Both segmentation rules and their parameter values and can be selected according to patient state or using an alternative fixed, programmable, responsive or other dynamic method. For example, more segments can be collected per interval of time, or the time between segments can be decreased, if the patient changes state or if such a change is anticipated (e.g. the monitoring program detects that the current time is associated with a time during which the patient normally goes for a morning walk).

Rows 3-7 in the table of FIG. 13*a* show exemplary parameters and associated parameter values that may govern the partitioning process of step 1002. Partitioning rules may cause these parameter values to change in relation to an event, such as a change in patient state. Partitioning rules can also cause parameter values to change sequentially such that partitioning occurs differently over several intervals that occur after an event.

Block 1006 shows exemplary data partitioned into three segments. After partitioning, these segments must then be evaluated. As indicated by block 1008, features relating to both intra-beat characteristics and inter-beat characteristics may be measured, as may occur using the feature extraction and measurement module 514 (FIG. 2) A first intra-beat feature can be the amount of ST-deviation which is calculated for each beat, a measure of QRS spectral-complexity, a measure derived as the ST-amplitude minus the preceding p-wave amplitude of the same beat, or a measure of the pressure which is exerted during a beat as measured from a pressure sensor. The inter-beat features may be comprised of statistics that are computed upon the intra-beat features such as mean value, range (e.g., maximum value-minimum value), or a measure of variance. Additionally, inter-beat features may include measures such as the R-R intervals for the beats of the cardiac segment, or statistics computed upon this measure including measures of the mean and variance of the R-R interval. As will be further described below, feature extraction and measurement is modulated by patient state information.

Rows 8-12 in the table shown in FIG. 13*a* shows exemplary parameters and associated parameter values that may govern the feature extraction process of step 1008. In this case, neither measures of QRS complexity nor the sum of the QRS voltages are calculated and the measured features are restricted to features related to the ST-segment.

After feature extraction, cardiac segments are scored based upon the extracted features as indicated by block 1010. This scoring by the result module 576 (FIG. 3) of the diagnostic module 516 and can be adjusted in relation to patient state information provided by module 568 by. A segment score rule can require a measure related to an event to be detected (e.g. surpass a threshold level) at more than one sensor in order to ensure a specified minimum spatial distribution of the event, or in order to ensure that the signal-to-noise ratio (SNR) of a particular sensor is sufficiently adequate and the detection is not spuriously due to noise energy. Additionally, inter-sensor delays may be specified in the segment score rules in order to decrease the risk of falsely detecting a medical event, wherein the measurements must be detected at two sensors with an expected range of delay that is intrinsic to the event being detected. The methods provide for classifying segments as normal or abnormal using any of these different criteria, wherein Na features from Nb sensors in Nc modalities can be evaluated using segment score rules to generate the segment score based upon multiple features of the data. Although segment scores can indicate if a segment is normal or abnormal, these scores need not be binary.

Rows 13-18 in the table shown in FIG. 13*a* provide exemplary parameters and associated parameter values that may govern the segment scoring process of step 1010. In this case the segment scores can assume values of 0 or 1, depending upon whether the features of the segment meets a threshold defined by the segment score parameter value. Cardiac segment score 5 is produces a value of false (0) or true (1) based upon whether scores 1 and 4 are both assessed as true.

The table of FIG. 13*b* shows exemplary segment scores rules associated score values for different segments (1, 2 and 3). As indicated in the table shown in FIG. 13*b*, segment score rules may be applied to data from particular sensors and both intra-beat and inter-beat features in order to generate one or more segment scores for a cardiac data segment. Intra-beat score rules are used to assess the features of each beat and may result in a beat score for each beat, which then contributes to the segment score. For example, a beat score can be computed for data related to each beat by comparing an intra-beat feature to a threshold value. The beat scores may then be individually utilized, or may be combined (e.g. summed or averaged), in order to obtain an intra-beat segment score. The inter-beat rules can likewise be used to evaluate the inter-beat features and produce an inter-beat segment score.

The cardiac segment summary scores can then be calculated using segment summary score rules (e.g. SSR1-SSR5). For example, rather than utilizing a single measure, such as ST-deviation, to detect abnormal cardiac activity, a segment score can be created using multiple segment score rules that are related to different features of the data. For instance a first score rule can be an intra-beat rule which assesses the amount of ST-deviation for each beat (e.g., ST-dev, for lead 1, segments 1 and 2 of the table shown in FIG. 13*b*). In this example, this results in a segment score of 3. A second score rule can be an inter-beat rule, which can assess the QRS variance of all the beats across the segment and assigns a score of 2 (e.g. QRS-complexity, for lead 1, segment 2 of the table shown in FIG. 13*b*). The segment summary score rule can then dictate how these score values are combined to produce at least one segment summary score. The table shows an example in which the intra-beat scores are summed to yield scores of 5 and 4 (e.g. SSR2 of segment 2 of the table shown in FIG. 13*b*). Segment scores can be used to create histogram data as is described in U.S. application Ser. No. 10/950,401 to Fischell et al.

Segment scores can be generated that are relevant for different types of cardiac conditions. For example, a first score rule can aim to detect the presence of ischemic cardiac abnormality, and would assign higher weights to beat scores related to ST-shift and QRS complexity, whereas a second score rule can be related to the detection of atrial flutter and would use a uni- or multi-various equation which would weight one or more beat scores more highly if these were related to atrial flutter.

After generation of segment scores control passes from block 1010 to block 1012, as shown in FIG. 12. In step 1012, a diagnostic rule is applied segment scores which may have been derived from both current and past segments. The diagnostic rule is applied by the diagnostic module 516 (FIG. 3), with particular reliance upon the results module 576 and comparison module 564. Diagnostic rules can use detection criteria, whereby if the detection criteria are exceeded then abnormal cardiac activity is detected and may lead to the triggering of an alert signal. For example, if a proportion of segments within of a set of segments (6 out of 8 consecutive segments) are classified as abnormal, and this proportion is greater than that the value specified by a detection criterion, then an abnormal medical event is detected. An abnormal medical event may be detected if any of several detection criteria are exceeded. Cumulative or mean segment scores across 1 or more sets of segments may be used as detection criteria, wherein a score of at least 8 across 2 segments or a score of at least 5 across 5 segments is defined by detection criteria as sufficient to detect abnormal cardiac activity.

Rows 19-21 in the table shown in FIG. 13a shows exemplary parameters and associated parameter values that may govern the application of a diagnostic rule and detection of an abnormal event as shown in step 1008 (FIG. 12). In one example, shown in row 19, if the cardiac segment score rule #1 remains true for 6 segments then an abnormal medical event worth of triggering an alarm has occurred. When segment scores are non-binary, rather than using a fixed threshold for number of segments, a sliding scale rule, as discussed in detail with reference to FIG. 8, may be used by the diagnostic rule criteria.

Interaction of Patient State and Partitioning Operations.

As described, patient state values can be used to adjust the steps 1002, 1008, 1010, 1012 and 1014 in FIG. 12, as indicated by the flow of information from block 1004 to these other blocks, and as was previously mentioned with respect to blocks 906 in FIG. 9A. If patient state data indicate that the patient recently lay down, then the cardiac segment partitioning module could increase the number of beats for each segment from 10 to 15 beats (i.e. from N=heart rate/6 to N=heart rate/4, where N is the number of beats in each segment). This type of adjustment based upon patient state can be useful in this case since when patient's lie down the number of premature ventricular contractions (PVCs) increases. By increasing the segment duration to enable a larger number of beats, the segment score will be affected less by in increased ratio of normal beats to beats with PVCs. This type of change can also occur if a patient pushes a button indicating an event such as a recent drinking of coffee.

The feature extraction and measurement step 1008 can also be adjusted by patient state. For example, if the patient data indicates that the patient recently lay down, the feature extraction module can be adjusted so that rather than extraction features related to an upright protocol, features related to a supine protocol are used. The upright protocol performs st-deviation analysis. If the patient state indicates a resting state, then the feature extraction and measurement module implements this ST-deviation as well as a u-wave detection and measurement algorithm. The patient state can be determined by a button press or can be defined based upon heart rate being below a selected level for a selected duration. In this example, the feature extraction and measurement module performs different operations for different heart-rates. In this case, more extensive analyses are performed at lower heart-rates. Additionally, the type of feature extraction algorithm which is used to detect a particular feature can be adjusted based upon patient state. For example, the shape of the T-wave is known to change with heart rate and so at higher heart rates, a different analysis window is used from the start of the t-wave compared to the window used at lower heart rates. Heart rate adjustment of ST measurement criteria is shown in U.S. Pat. No. 6,609,023 to Fischell et al. Further, the classification between QRS and T-wave complexes can be made contingent upon the interval between an upstroke and the subsequent downstroke. If the interval is longer than a threshold interval value (e.g. 80 msec) then the complex is identified as a T-wave rather than QRS. Alternatively, the complex could be discarded as not being either. This interval threshold value can be adjusted based upon patient state so that data supplied by this feature extraction operation is adjusted accordingly.

The cardiac segment scoring shown in step 1010 in FIG. 12 can also be adjusted according to patient state. For example, if patient state data indicates that the patient recently lay down, then the cardiac segment scoring algorithm could increase the threshold for detection of ST-deviation. Additionally, the cardiac segment score could increase the proportion of beats which must be detected as abnormal in order for the segment to be scored as abnormal, for example, a proportion threshold value of 60% could be increased to 80%.

Applying diagnostic rules 1012 in FIG. 12 can also be adjusted based on patient state. For example, if patient state data indicate the patient recently lay down, then the cardiac diagnostic score rule 1012 could increase the threshold for detection of a medically relevant event that is used by the score algorithm. For example, the event could be detected using a criterion wherein the threshold value, of abnormal segments which need to occur for an event to be detected, is increased from 3 to 6 segments.

Table 3 shown in FIG. 13C illustrates how a consideration of both cardiac features and heart rate can be used to guide the strategy implemented by the diagnostic score rules. The table shows that ST-elevation may be evaluated as a function of heart rate, such that when ST-elevation occurs at a lower heart-rate, very few cardiac segments must be scored as abnormal prior to an alarm being sent. In contrast, when ST-elevation occurs at a higher heart-rate, the abnormal segment criterion may be increased slightly. In this example, ST-elevation is defined with respect to a single lead that has a "can to tip" polarity. In the case of detection of ST-depression, the diagnostic rule may require that abnormal segment scores occur a specified number of times during a normal heart-rate. When this occurs at a higher heart-rate, activity from an EMG or other sensor is also be used to ensure that the patient state is not exercising. Since this type of change may be normally induced by exercising, it should not lead to the detection of a medical event when the patient state data indicate that this is true. The use of patient state for adjusting the detection of medically relevant events improves performance since adjusting detection based upon heart rate level, patient state, and the type of features which have been observed, should increase sensitivity and specificity of the device.

Generation and Utilization of Reference Data

In one preferred embodiment of the present invention cardiotrend system 500, abnormal categories can be selected, or formed, using abnormal data collected prior to or during clinical intervention. For example, reference data from periods when the patient's heart expressed 2 or 3 types of abnormal symptoms, or while the patient was in 1 or more states of arousal, can be used to create the abnormal data sets for the classification operations. Self-norm data obtained during a surgical procedure, such as angioplasty, where acute ischemic events can be induced, can provide abnormal data which serves as a customized template for the specific abnormalities which that patient may subsequently demonstrate during monitoring with the cardiotrend system. Self-norm data can also be data which is obtained during a stress test and which is indexed by heart-rate. When the self-norm is derived from an abnormal rather than normal state of the patient, the statistical comparison can be configured to detect a current state which is moving towards abnormal state, rather than deviating from a normal state, as is often done. This type of approach also tailors the detection of abnormal activity with respect to a particular abnormality for that patient, rather than some type of general abnormality. If a patient normally demonstrates a particular abnormality, and only certain changes are important, then this type of detection scheme may perform better than an approach which compares the cardiac activity to normal reference data. In one embodiment, the comparison of the current data to abnormal self-norm reference data would cause a decrease, rather than increase, in a clinical vector, and when this decrease was significant, an alarm would be triggered.

Diagnostic Methods Using Temporal and Spectral Features of Sensed Data.

Although the diagnostic module 516 can monitor and detect cardiac disorders using an assortment of methods, several specific embodiments should be discussed in order to provide illustrative examples of how spectral and temporal features of the data may be evaluated. Both spectral analysis and higher order spectral analysis, such as the bispectral index, can provide valuable measures related to the detection of cardiac disorders. In an embodiment of the medical monitoring of syncope, the cardiotrend system 500, can measure both heart rate and blood pressure variability using cross-spectral analysis, and can issue an alert signal prior to a syncope episode due to detection of a drop of the baroreflex coupling, as can occur immediately before syncope (e.g., Faes et al., 2006). Additionally, assessment of spectral measures can provide indices of phase decoupling, which are useful in detecting, quantifying, and classifying both atrial and ventricular arrhythmias. Ventricular arrhythmias, especially ventricular fibrillations, are the most common arrhythmic events found in patients suffering from sudden cardiac death. Prompt interventional therapy, upon detection of the presence or an increase of these abnormalities can deter this unwanted outcome (e.g., Khadra et al, 2005).

Spectral measures of heart-rate variability have also been shown to be useful in detecting and quantifying a number of cardiac abnormalities. Abnormal measures of heart rate variability (HRV) have been shown to be good predictors of outcome in acute myocardial infarction, stroke, head trauma, and risk of mortality in the elderly. Not only very low frequency, low frequency, and high frequency measures, but also ratios and composites (e.g., LF-to-HF ratio) have been shown to have diagnostic and prognostic value (e.g., Stein et al, 2005; Gujjar et al., 2004). Using the feature analysis module 554, these measures can be derived and used by the cardiotrend system to evaluate the value of therapy and the overall patient condition over time. For example, using trend analysis module 560 HRV measures can be evaluated over time. HRV can be measured in relation to different spectral bands. For example, the low-frequency (LF, 0.04-0.15 Hz) and high-frequency power (HF, 0.15-0.40 Hz), can be calculated and the LF-to-HF power ratio (LF/HF), or normalized powers (LF % and HF %) can be used. These measures can reflect augmented sympathetic and attenuated parasympathetic activity that is associated with different cardiac-related disorders, including those which can exist in head-injured patients.

Spectral and spectral-temporal features can also be utilized in order to determine when to immediately apply therapy such as defibrillation, when it may be better to slightly delay this intervention, and when other methods of cardiopulmonary resuscitation should be delivered prior to defibrillation attempts, in order to increase the success of this latter intervention (e.g., Brown et al, 1996; Strohmenger et al, 1996; Strohmenger et al, 1997; Noc et al, 1999; Eftestøl et al. 2000; Berg et al. 2002; Eftestol T et al., 2005). Based upon analysis, which may include automatic or patient assisted measurement and classification of spectral and spectral-temporal features, the cardiotrend system (including the medical officer of central station or physician who has obtained data sent by the system via telemetry) can provide alarm warnings and status messages which may be utilized by the paramedics who are treating a patient who has experienced an initial cardiac episode requiring intervention. These warning may include warnings to "wait prior to intervention", or to "deliver cardiopulmonary resuscitation" or to "deliver cardiopulmonary resuscitation prior to next defibrillation attempt" or to "delivery alternative therapy" where alternative therapy may include providing a particular drug and at a particular dose prior to, or instead of, defibrillation attempts.

A number of studies have found that spectral analysis measures can reflect circadian and diurnal patterns of cardiac activity (e.g., Bilan et al., 2005). Spectral analysis can be used by the Cardiotrend system in order to classify and organize stored data according to patient state. Spectral analysis can also be used to identify changes which are independent of these regular patterns of activity (e.g., by compensating or otherwise adjusting for the features of the cardiac data which are related to these biological rhythms). The state module 568 of the diagnostic module 516 may be programmed so as to be able to detect and measure these rhythms to define different patient states, and can incorporate this analysis into the classification of stored data and detection of abnormal activity. The state module and methods 568 can determine how to change the CTOs, when a change in patient state has been detected that is related to these diurnal patterns. Similar to more obvious rhythms (e.g., waking up) diurnal rhythms can be used to contextualize the manifestation a type of cardiac activity (e.g., the occurrence of a slight arrhythmia). Accordingly, the cardiotrend system can evaluate cardiac activity and provide medical alerts if normal diurnal patterns in cardiac activity do not occur, or occur outside of an expected range, for an abnormal duration, or in an otherwise abnormal manner. The trend module of the cardiotrend system is exceptionally well tailored to provide relevant data which would be used in providing an alert signal for this type of abnormality.

Cardiotrend Operations Related to Medication

A number of studies have examined the relationship between abnormal cardiac activity and subsequent response to anti-arrhythmic drug effects. Analysis of P-wave signals which are computed upon the averaged surface ECG during sinus rhythm can be combined with the spectral characterization of fibrillatory waves during atrial fibrillation, to predict response to atrial anti-arrhythmic drugs (e.g., flecainide, propafenone, dofetilide, amiodarone). By combining both temporal and spectral measures of cardiac activity, the cardiotrend system 500 is not limited only to the detection of abnormalities and can be used select drugs with increased likelihood of normalizing the activity (e.g., Husser et al., 2004). In one embodiment, the result module 576 of the diagnostic module 516 will produce an alarm and provide a preferred drug of treatment to the patient based upon a classification of the cardiac data. This can include providing the pills themselves, a text message to the patient by the device, a message sent via the central station to the paramedics, or by actual drug delivery via an implanted drug delivery system.

This type of prescriptive feature can occur in the cardiotrend system 500*a* of FIG. 1A itself or via the central station 505 based upon analysis of transmitted data from the programmer 501, EXD 502A or DTD 502B. The prescriptive feature can incorporate prescriptions made by a physician for that patient and in relation to certain types of activity, such as "if monitored data meet specified criteria then supply amount Z1 of drug X, while if the data meet a second set of criteria then supply amount Z2 of drug Y".

The evaluation of data with respect to pre-selected criteria can occur automatically by the cardiotrend system, but may further require the confirmation of a physician to whom an alert signal is sent, to realize the treatment which was prescribed by the physician. Whether occurring at the central station 505, or in the device itself (e.g. the implanted CTI 500A), the classification and prescription feature can utilize two or more prescriptions previously provided by a physician. For example, if the classification scheme determines that a particular abnormality is occurring one prescription previously defined by the physician can be suggested, whereas a different classification result can lead to the triggering of a provision of medication according to a different prescription.

The monitoring and detection abnormal cardiac activity by the cardiotrend system 500 can be adjusted according to medications used by the patient. For example, the system can adjust its analysis and storage operations based upon: medications provided to the patient; elapsed-time since these were provided; and, the amounts which were provided. When evaluating a drug response, the analysis can consider cardiac abnormalities which may have more of a chronic rather than acute duration and may evaluate the severity of a condition rather than simply detecting the emergence of a cardiac event. In other words, the heart of a patient may always be abnormal and cardiac events may therefore continuously be detected. In this situation alerts can be sent when the condition worsens or stops showing an improvement to drug treatment, rather then due to the transition from normal to abnormal cardiac state or the detection of an acute abnormal event.

The cardiotrend system 500 can assist in evaluating response to drug treatments since it can be chronically operated over many months. In the clinical setting it is sometimes difficult to directly evaluate the overall effects of anti-arrhythmic drugs on the individual patient's atrial electrophysiology and the currently utilized atrial fibrillation (AF) management guidelines do not usually provide treatment recommendations that take the various characteristics/patterns of AF into account when prescribing medications. By storing features of the data, and histograms and trend plots that are oriented towards evaluating a patient's response to medication, the efficacy of that medication can be evaluated. The cardiotrend system 500 and methods can quantify the AF disease state and guide AF management based upon automatic evaluation of trend graphs, or by professional evaluation of trend data that has been transmitted to the central station. The trend analysis module 560 of the cardiotrend diagnostic module 516 can be tailored to provide trend graphs that are reflective of a patient's response to medication over a period of days, weeks, or months.

In one embodiment the cardiotrend system 500 also uses the alarm module 522 of FIG. 1B to provide a "take your medicine" alarm that reminds the patient to take medication. The alarm module 522 may provide the "take your medicine" alarm according to a patient compliance module 574A which can trigger this alarm in response to sensed data or due to a time specified in a treatment program or even due to the failure of a patient to press a button and indicate that medication has been taken at a specified time (e.g., when the patient has been directed to press a specified event button when taking the medication). In other words, the alarm module 522 can be operated to improve the likelihood of patient compliance in successfully adhering to medication protocols prescribed by a physician. Compliance may be measured as taking medication within a specified window of a specified time, a can relate to other aspects of patient behavior such as exercising a specified amount by a certain time each day, or any other behavior which is prescribed with treatment. Compliance measures can be obtained by a patient pushing buttons on the cardiotrend system 500 to indicate events such as taking medication have occurred, or can be sensed by changes in the monitored data which occur in response to events occurring (e.g., taking medication can lead to an immediate and acute change in cardiac activity which could be detected automatically by the system). Sensed data can also include signals related to the presence of the drug itself when the drug contains a physical signature such as a microchip emitter in the medication capsule itself or a chemical, or physical, property which is sensed by the system 500. Repeated failure of a patient to adhere to a medication schedule could result in an alert signal being sent to a central station.

Furthermore, by monitoring signals sensed from the patient's heart, the cardiotrend system 500 can sense changes related to taking medication, and infer that the patient has taken a pill. The system 500 can then evaluate a patient's response to medication as compared to an expected response, such as a prior self-norm of a response to medication. The alarm module 522 provide an alert to increase/decrease the amount of medication to be taken based upon the relative cardiac response to the medication, compared to the prior responses of the patient.

Rather than taking medications regularly, the system 500 could provide, or help a physician provide, a schedule that is based upon the patient's cardiac activity. In this way the cardiotrend system 500 can help provide semi-automated closed loop drug monitoring and delivery. If connected to a drug pump, the cardiotrend system 500 could provide fully or semi-closed loop drug monitoring and delivery. The alarm module 522 can provide the "take your medicine" alarm according to a time specified in a treatment program which is programmed into the patient compliance module 574A in order to increase patient compliance. Additionally, the "take your medicine" alarm may only occur when a patient fails to press a button and indicate that medication has been taken only when a time range beyond a target time is exceeded.

The alarm module 522 can also provide the "take your medicine" alarm when sensed data suggest that additional medication is needed on an acute basis. For example if excessive ST elevation is detected indicating transmural ischemia (i.e. a heart attack) then the "take your medicine" alarm could alert the patient to chew an aspirin or place nitroglycerine under their tongue. The "take your medicine" alarm could be a special vibration mode of the internal alarm provided by the CTI 500A of FIG. 1A or an audio or visual external alarm provided by the EXD 502A and/or DTD 502B. Ideally in precarious situations both internal and external alarms are provided. It is envisioned that the external alarm could be a pre-recorded speech announcement that would verbally instruct the patient as to the type and amount of medicine to be taken.

Unlike monitoring of cardiac abnormalities related to decreased health of the heart, the cardiotrend system 500 can track changes in cardiac activity which are improvements using the medication evaluation module 574B. The patient's response to medication can be evaluated wherein monitoring of cardiac activity is configured for detecting a normalization of atrial fibrillation over time. This is useful for monitoring improvement over a number of weeks, and also to alert the patient or the physician if the trend for improvement reverses or plateaus so that a different drug can be supplemented or exchanged with the current drug prior to the patient experiencing a serious medical event. The normalization of atrial fibrillation can be measured using an index of fibrillation frequency, magnitude, duration, or type or a combination of these measures. In another example, the patient's response to medication can be monitored by detecting P-waves in the electrogram and/or a normalization (e.g., reduction) of R-R interval variability. By examining the changes which occur in different patients who eventually emerge as successful or non-successful outcomes, the important changes can be determined, and this can further be done with respect to particular medications. The monitoring of these specific changes can then be incorporated into the cardiotrend system 500. The diagnostic module 516 can include a medication evaluation module 574B which is specifically designed to monitor improvements related to taking specific medications, although this functionality can be generally realized utilizing the other modules of the diagnostic module 516 with appropriate modification of the treatment program. The patient compliance module 574A and medication evaluation module 574B, are part of the extra features module 574 which is a programmable module which can be used to supply extra features into the cardiotrend system 500 by creating customized modules that are tailored to individual patients.

Control Law Implementation

The control module 518 of FIG. 1B can use sensed signals from the sensing module 510 or monitoring results sent from the diagnostic module 516 in order to control the alarm module 522, and/or intervention module 524 to implement control laws. The control module 518 may utilize subroutines of the control law module 572 in order to realize control over cardiac state. It is understood that actions taken based upon alerts provided by the alarm module can act to control cardiac activity, albeit by a more indirect path (i.e. human intervention) than operations of the intervention module 524. The control law may be a proportional control law where the volume of the alarm is increased according to the size, severity, or type of abnormal event which is detected. In other words, the intervention provided by the physician or patient can vary in response to the severity of the alarms which serve as one type of feedback signal which is provided by the control system. The control program 519 of the control module 518 can implement control laws to provide cardiac stimulation and pacing signals in response to sensed data, in order to provide therapy, for example, in order to maintain cardiac activity within a normal range. Control laws may be selected, adjusted or implemented in a number of manners, for example, based upon the patient's state, and according to a range of a particular measurement such as heart-rate.

When relying upon control laws, the cardiotrend system can provide for cardiac modulation in the treatment of disease. When used in a control law implementation the components of system may include an input stage (A,B), a control-law processor stage (C,D), and an output stage (E,F,G) which may be realized as: A. a sensing module containing at least a signal conditioning module; B. at least one sensor, but preferably two sensors which send their signals to the sensing module; C. a signal conditioning module containing at least one signal processor which receives signals from the sensing module, and the signal processor performs cardiac state estimation; D. a control module having at least one control circuit governed by at least one control law which communicates with the signal processor to obtain its output; and at least one of E, F or G where E. is an intervention module having a generic device module which can provide control of stimulation provided by generic devices that are in communication with said control module; F. is a stimulation module, which can directly or indirectly provide stimulation via at least one stimulation conduit which provides stimulation according to the control commands of the control module; and G is an alert module which can provide an alert signal which has at least one characteristic which is modifiable based upon an characteristic of the input signal.

The control laws of the control module 518 can initiate, adjust, or terminate stimulation, or alarms, or other CTOs, in order to cause cardiac state to be controlled. Controlling cardiac state may include increasing the chances of, at least one of the following with respect to the cardiac state: to remain within a normal range; to remain within control range, for example, which may be abnormal but within a limited range selected by a physician; to remain outside of a borderline range, for example, which is defined as tending towards being abnormal without being large enough to trigger an alarm; to remain outside of a critical range, for example, where an alarm may be triggered, but the patient does not enter cardiac arrest; to prevent the occurrence of at least one of abnormal cardiac signs and symptoms, for example, an arrhythmia; to prevent the occurrence of precursors to at least one of signs and symptoms related to a cardiac disorder; to prevent the occurrence of EKG abnormalities; to control measures of cardiac chaos; to cause cardiac synchronization of chaos to be controlled; to cause cardiac synchronization to be controlled; to cause cardiac entrainment to be controlled; and to cause cardiac disentrainment to be controlled.

Alternative Embodiments

The cardiotrend system 500 as described herein may be primarily oriented towards monitoring of cardiac electrical activity. Other embodiments, however, are no less useful and may be preferred, instead of, or in addition to, sensed electrical activity in the monitoring of different disorders. For example, optical data can be obtained which is related to SAO2 levels, in order to detect ischemic status of different vessels supplying the heart. Abnormalities can be localized by computing difference between measures from different sensors, especially with respect to SAO2 levels or flow velocity. While cardiac electrical activity may reflect the functional perfusion of the heart, this measure is an indirect measure of the actual flow rates and oxygen saturation of the blood being supplied by arteries to the heart. When SAO2 levels are measured optically, for both arterial and venous passages, functional oxygen availability and usage (the difference in input and output oxygen levels) can be computed. Further, biochemical markers can be sensed by sensors and monitored by the system 500. For example, increased plasma fibrinogen levels and platelet proteins, are frequently encountered in significant multi- and single-vessel disease patients. The levels of these substances or the biochemical correlates of these levels (as well as biochemical pro- and anti-inflammatory markers, such as increased VEGF levels and decreased concentration of IL-10 levels), can provide an index of cardiac disease status. Additionally, flow rates, sonic, and mechanical measures of heart activity and blood flow can be obtained using flow, pressure, sonic, ultrasonic, and Doppler methods which can be accomplished by implanted or external devices which may be a part of, or which may communicate with, the cardiotrend system 500. The use of patient state can be implemented by a system which is being used to monitor (with or without responsive stimulation or alerting) neurological medical events, especially when these events relate to cardiac related disorders having neural correlates, and can also be utilized by implanted devices configured to treat various other disorders as well.

The presently described embodiments of the CardioTrend systems and methods offer advantages over prior art. Although modifications and changes may be suggested by those skilled in the art, it is the intention of the inventor to embody within the patent warranted herein all changes and modifications as reasonably and properly come within the scope of their contribution to the art. All prior art cited, including scientific references, are incorporated by reference herein as if recited fully. The titles, headings, and subheadings provided in this specification are provided for organizational purposes only and are not meant to restrict the invention in any way, nor to limit material described in one section from applying to another section as would be apparent to those skilled in the art.

REFERENCES

1. Berg R A, Hilwig R W, Kern K B, et al. Precountershock cardiopulmonary resuscitation improves ventricular fibrillation median frequency and myocardial readiness for successful defibrillation from prolonged ventricular fibrillation: a randomized, controlled swine study. Ann Emerg Med 2002; 40:563-71.
2. Bilan A, Witczak A, Palusinski R, Myslinski W, Hanzlik J. Circadian rhythm of spectral indices of heart rate variability in healthy subjects. J. Electrocardiol. 2005 July; 38(3): 239-43.
3. Brown C G, Dzwonczyk R. Signal analysis of the human electrocardiogram during ventricular fibrillation: frequency and amplitude parameters as predictors of successful shock. Ann Emerg Med 1996; 17:436-7.
4. Clifford G D, Tarassenko L. Quantifying errors in spectral estimates of HRV due to beat replacement and resampling. IEEE Trans Biomed Eng. 2005 April; 52(4):630-8.
5. Eftestol T, Losert H, Kramer-Johansen J, Wik L, Sterz F, Steen P A. Independent evaluation of a defibrillation outcome predictor for out-of-hospital cardiac arrested patients. Resuscitation. 2005 October; 67(1):55-61.
6. Eftestøl T, Sunde K, Aase S O, et al. Predicting outcome of defibrillation by spectral characterization and nonparametric classification of ventricular fibrillation in patients with out-of-hospital cardiac arrest. Circulation 2000; 102:1523-9.
7. Faes L, Widesott L, Del Greco M, Antolini R, Nollo G. Causal cross-spectral analysis of heart rate and blood pressure variability for describing the impairment of the cardiovascular control in neurally mediated syncope. IEEE Trans Biomed Eng. 2006 January; 53(1):65-73.
8. Gujjar A R, Sathyaprabha T N, Nagaraja D, Thennarasu K, Pradhan N. Heart rate variability and outcome in acute severe stroke: role of power spectral analysis. Neurocrit Care. 2004; 1(3):347-53.
9. Hoppe B L, Kahn A M, Feld G K, Hassankhani A, Narayan S M. Separating atrial flutter from atrial fibrillation with apparent electrocardiographic organization using dominant and narrow F-wave spectra. J Am Coll Cardiol. 2005 Dec. 6; 46(11):2079-87.
10. Husser D, Stridh M, Sornmo L, Platonov P, Olsson S B, Bollmann A. Analysis of the surface electrocardiogram for monitoring and predicting antiarrhythmic drug effects in atrial fibrillation. Cardiovasc Drugs Ther. 2004 September; 18(5):377-86. Review.
11. Khadra L, Al-Fahoum A S, Binajjaj S. A quantitative analysis approach for cardiac arrhythmia classification using higher order spectral techniques. IEEE Trans Biomed Eng. 2005 November; 52(11):1840-5. Kligfield P, Okin P M. Heart Rate Adjustment of ST Depression and Performance of the Exercise ECG", International Journal of Bioelectromagnetism, No. 1, Vol. 2, 2000.
12. Langley P, Bowers E J, Wild J, Drinnan M J, Allen J, Sims A, et al. An algorithm to distinguish ischaemic and non ischaemic ST changes in the Holter ECG. Computers in Cardiology 2003; 30: 239-42.
13. Lehtinen. Diagnostic and Prognostic Value of ST/HR Hysteresis. International Journal of Bioelectromagnetism, No. 1, Vol. 2, 2000.
14. Menown I B, Patterson R S, MacKenzie G, Adgey A A. Body-surface map models for early diagnosis of acute myocardial infarction J. Electrocardiol. 1998; 31 Suppl.: 180-8.
15. Minchole, A. Skarp, B. Jager, F. Laguna, P. Evaluation of a Root Mean Square Based Ischemia Detector on the Long-Term ST Database with Body Position Change Cancellation", Computers in Cardiology 2005; 32:853-856.
16. Noc M, Weill M H, Tang W, et al. Electrocardiographic prediction of the success of cardiac resuscitation. Crit Care Med 1999; 27(4):708-14. Papaloukas C, Fotiadis D I, Likas A, et al. Automated Methods for Ischemia Detection in Long-Duration ECGs" Cardiovasc Rev Rep 24(6):313-320, 2003.
17. Singh D, Vinod K, Saxena S C, Deepak K K. An improved windowing technique for heart rate variability power spectrum estimation. J Med Eng Technol. 2005 March-April; 29(2):95-101.
18. Stein P K, Domitrovich P P, Hui N, Rautaharju P, Gottdiener J. Sometimes higher heart rate variability is not better heart rate variability: results of graphical and nonlinear analyses. J Cardiovasc Electrophysiol. 2005 September; 16(9):954-9.
19. Strohmenger H U, Lindner K H, Brown C G. Analysis of the ventricular fibrillation ECG signal amplitude and frequency parameters as predictors of countershock success in humans. Chest 1997; 111:584-9.
20. Strohmenger H U, Lindnder K H, Lindner I M, et al. Spectral analysis of ventricular fibrillation and closed-chest cardiopulmonary resuscitation. Resuscitation 1996; 33(2): 155-61.
21. Xu W, Tse H F, Chan F H, Fung P C, Lee K L, Lau C P. New Bayesian discriminator for detection of atrial tachyarrhythmias. Circulation. 2002 Mar. 26; 105(12):1472-9. Zimmerman, M. W., Povinelli, R. J. On Improving the Classification of Myocardial Ischemia Using Holter ECG Data. Computers in Cardiology 2004; 31:377-380.

We claim:
1. An implantable device for tracking the cardiovascular condition of a human patient, the device including:
an electrode adapted for placement inside a human patient to sense the electrical signal from the patient's heart, the electrical signal being an electrogram which consists of a multiplicity of beats;
a digital processor configured to:
acquire the electrogram and compute from the electrogram a plurality of values of a heart signal feature;
compute both first and second aspects pertaining to the plurality of values of the heart signal feature within the acquired electrogram, wherein the first and second aspects are at least partially independent of one another and are defined as a magnitude of the heart signal feature and time duration over which said heart signal feature is computed, respectively; and detect a cardiovascular condition by applying a test to the plurality of values of the heart signal feature within the acquired electrogram, wherein the test is at least partially based on a sliding scale such that the first and second aspects of the plurality of values vary in accordance with one another.

2. The implantable device of claim 1 wherein the heart signal feature is ST segment shift.

3. The implantable device of claim 1 wherein the sliding scale is implemented by applying a threshold to the first aspect such that the value of the threshold depends on the value of the second aspect.

4. The implantable device of claim 1 wherein the sliding scale is implemented by forming a weighted sum of first and second cardiac state parameters, wherein each of the first and second cardiac state parameters is a function of the values of both the first and second aspects.

5. The implantable device of claim 4 wherein the first state parameter is equal to the number of heart beats that a heart signal feature value of the plurality of values of the heart signal feature exceeded a first threshold, and the second state parameter is equal to the number of heart beats that a heart signal feature value exceeded a second threshold.

6. The implantable device of claim 1 wherein the sliding scale is implemented by applying first and second thresholds to first and second cardiac state parameters, wherein each of the first and second cardiac state parameters is a function of the values of both the first and second aspects, and wherein the cardiac condition is detected if either of the first or second cardiac state parameter exceeds the corresponding first or second threshold.

7. The implantable device of claim 6 wherein the first state parameter is equal to the number of heart beats that a heart signal feature value of the plurality of values of the heart signal feature exceeded a first threshold, and the second state parameter is equal to the number of heart beats that a heart signal feature value exceeded a second threshold.

8. The implantable device of claim 6 wherein the sliding scale is implemented by applying third and fourth thresholds to first and second cardiac state parameters, wherein the third and fourth thresholds are smaller than the first and second thresholds, respectively, and wherein the cardiac condition is detected if both the first and second cardiac state parameters exceeded the third and fourth thresholds, respectively.

9. An implantable device for tracking the cardiovascular condition of a human patient, the device including:

an electrode adapted for placement inside a human patient to sense an electrical signal from the patient's heart, the electrical signal being an electrogram which consists of a multiplicity of beats, a digital processor configured to:

acquire the electrogram and to compute from the electrogram both a first plurality of values of a first heart signal feature and a second plurality of values of a second heart signal feature;

apply a test to the first plurality of values and the second plurality of values within the acquired electrogram, wherein the test is at least partially based on a sliding scale such that the first plurality of values and the second plurality of values vary in accordance with one another.

10. The implantable device of claim 9 wherein the first heart signal feature pertains to cardiac repolarization.

11. The implantable device of claim 10 wherein the first heart signal feature pertains to the ST segment.

12. The implantable device of claim 10 wherein the second heart signal feature pertains to cardiac activation.

13. The implantable device of claim 10 wherein the second heart signal feature pertains to cardiac repolarization, and wherein the first and second heart signal features pertain to different aspects of cardiac repolarization.

* * * * *